(12) United States Patent
Singaram et al.

(10) Patent No.: US 8,394,357 B2
(45) Date of Patent: *Mar. 12, 2013

(54) OPTICAL DETERMINATION OF GLUCOSE UTILIZING BORONIC ACID ADDUCTS

(75) Inventors: Bakthan Singaram, Santa Cruz, CA (US); Ritchie A. Wessling, Watsonville, CA (US)

(73) Assignee: The Regents of the University of California, Oakland, CA (US)

( * ) Notice: Subject to any disclaimer, the term of this patent is extended or adjusted under 35 U.S.C. 154(b) by 732 days.

This patent is subject to a terminal disclaimer.

(21) Appl. No.: 12/189,082

(22) Filed: Aug. 8, 2008

(65) Prior Publication Data

US 2009/0148344 A1    Jun. 11, 2009

Related U.S. Application Data

(63) Continuation of application No. 11/296,898, filed on Dec. 7, 2005, now Pat. No. 7,470,420, which is a continuation-in-part of application No. 10/456,895, filed on Jun. 5, 2003, now abandoned, which is a continuation-in-part of application No. 09/731,323, filed on Dec. 5, 2000, now Pat. No. 6,627,177.

(51) Int. Cl.
*A61B 5/00* (2006.01)
*A61B 8/00* (2006.01)
*A61B 10/00* (2006.01)

(52) U.S. Cl. ........ 424/9.6; 424/1.11; 424/1.65; 424/9.1; 514/741; 514/765

(58) Field of Classification Search .................. 424/1.11, 424/1.65, 1.81, 185, 9.1, 9.2, 9.6; 568/18, 568/300; 436/106, 131, 172; 514/741, 765
See application file for complete search history.

(56) References Cited

U.S. PATENT DOCUMENTS

| | | | |
|---|---|---|---|
| 4,844,841 A * | 7/1989 | Koller et al. | 562/55 |
| 6,627,177 B2 * | 9/2003 | Singaram et al. | 424/9.6 |
| 7,417,164 B2 * | 8/2008 | Suri | 562/31 |
| 7,470,420 B2 * | 12/2008 | Singaram et al. | 424/9.6 |

OTHER PUBLICATIONS

Kano et al, Chemistry Letters, 1980, vol. 8, pp. 1035-138.*
Robertson et al (Macromolecules, 1996, vol. 29, No. 15, pp. 5166-5171).*

* cited by examiner

*Primary Examiner* — D L Jones
(74) *Attorney, Agent, or Firm* — Sam K. Tahmasebi; TechLaw LLP

(57) ABSTRACT

The present invention concerns an improved optical method and optical sensing device for determining the levels of polyhydroxyl-substituted organic molecules in vitro and/or in vivo in aqueous media. The range of detection is between about 400 and 800 nm. In particular, a sensory devise is implemented in a mammal to determine sugar levels. Specifically, a dye is combined with a conjugated nitrogen-containing heterocyclic aromatic boronic acid-substituted bis-onium compound in the presence of a sugar, such as fructose or glucose. The viologens are preferred as the aromatic conjugated nitrogen-containing boronic acid substituted compounds. The method is useful to determine sugar levels in a human being.

15 Claims, 24 Drawing Sheets

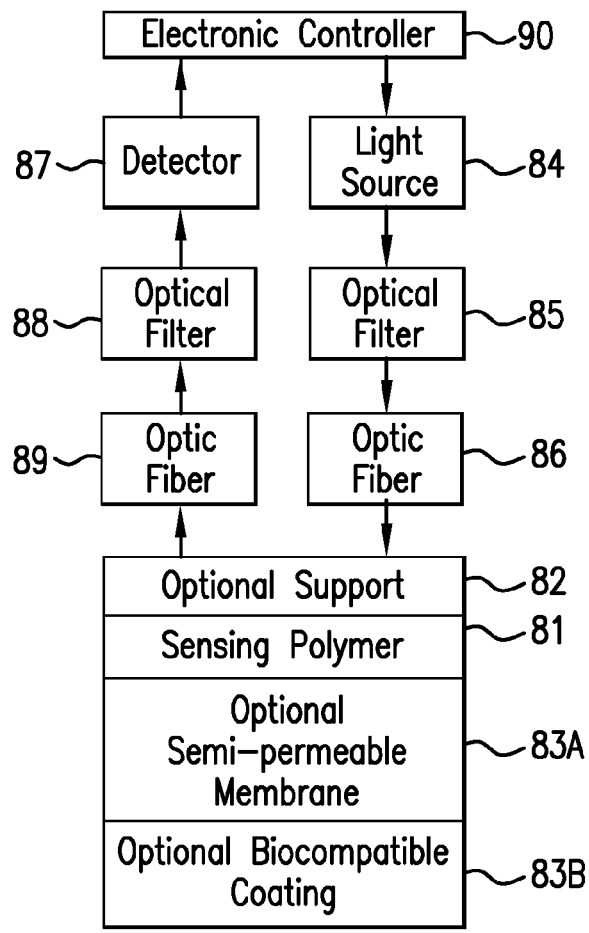
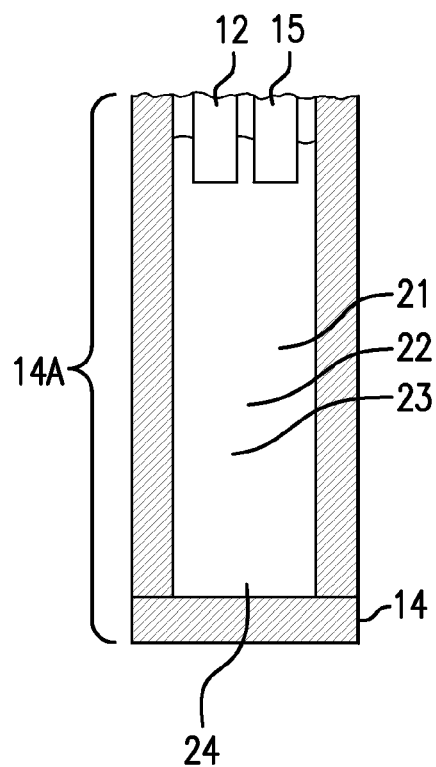
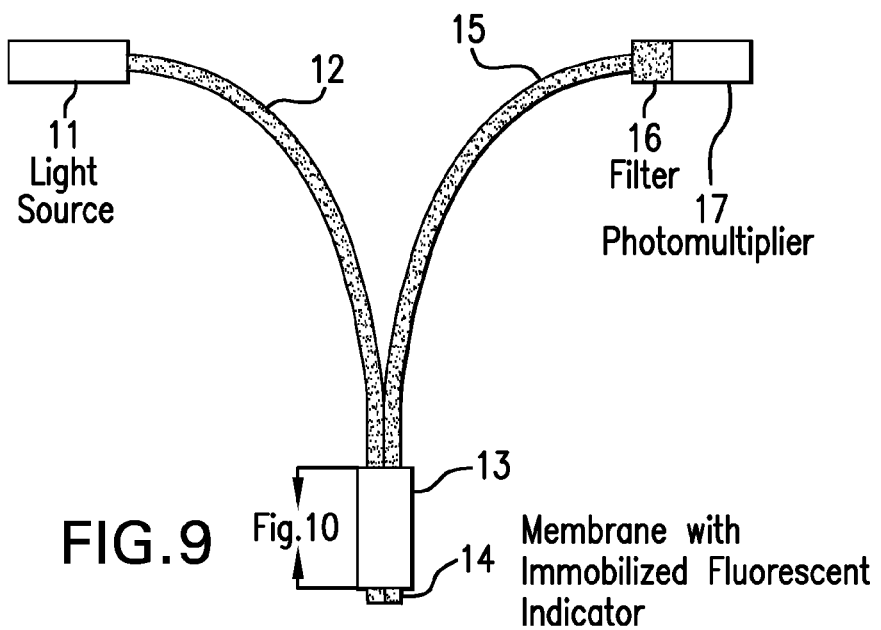
FIG. 8
FIG. 10
FIG. 9

Characteristic fluorescence response on addition of quencher to QD solution followed by addition of glucose to the quencher solution at pH 7.4. Final quencher:QD ($o$-BBV$^{2+}$:NH$_2$QD) ratio for this data: 50:1. Final glucose concentration: 100mM.

OPTICAL DETERMINATION OF GLUCOSE UTILIZING BORONIC ACID ADDUCTS

RELATED APPLICATIONS

This application is a continuation of U.S. patent application Ser. No. 11/296,898, filed Dec. 7, 2005 now U.S. Pat. No. 7,470,420, which in turn is a continuation-in-part of U.S. Ser. No. 10/456,895, filed Jun. 5, 2003 now abandoned, which is a continuation-in-part of prior U.S. application Ser. No. 09/731,323, filed Dec. 5, 2000, now U.S. Pat. No. 6,627,177, issued Sep. 30, 2003, which preceding applications are hereby incorporated by reference in their entirety.

BACKGROUND OF THE INVENTION

1. Field of the Invention

This invention relates to an improved optical method and/or sensor for polyhydroxy substituted organic molecules that measure the concentration of these molecules in aqueous or organic media. In one application, the method and sensor monitor the concentration of sugars, i.e. glucose or fructose, in aqueous solution in vitro. In particular, the method and sensor monitor the concentration of sugars, i.e. glucose or fructose, in aqueous solution in vivo. The determination of glucose in fluids in vivo and in vitro—is of importance. The in vivo sensing device is implanted in a human being. Some of the novel components of the optical method and device are also considered to be inventions in their own right.

2. Description of Related Art

There has been an ongoing effort over many years to use fluorescence techniques to measure polyhydroxyl compound (e.g. glucose) concentrations in body fluids. Although the term "glucose" is used herein below, it is to be understood that the concentration of most polyhydroxyl-containing organic compounds (carbohydrates, 1,2-diols, 1,3-diols and the like) in a solution are determined. But in spite of the intense effort, no practical system has been developed and commercialized for in vivo monitoring. Several attempts have been made to detect glucose by fluorescence using dyes to which a boronic acid group has been attached. Boronic acids are known to bind sugars reversibly. When the boronic acid functional dye binds to a sugar, the properties of the dye are affected. These changes have been used in the past to measure sugar concentration.

One use of this approach to a glucose sensor was reported by Russell, U.S. Pat. No. 5,137,833 (See also Russell & Zepp, U.S. Pat. No. 5,512,246) which disclosed the use of a boronic acid functionalized dye that binds to glucose and generates a signal dependent on glucose concentration. James et al U.S. Pat. No. 5,503,770 used the same principle but combined a fluorescent dye, an amine quenching functionality, and a boronic acid in a single complex moiety, the fluorescence emission from which varies with extent of glucose binding. Van Antwerp et al U.S. Pat. No. 6,002,954 and U.S. Pat. No. 6,011,984 combined features of the previously cited references and also taught fabrication of a device that is purported to be implantable. A. E. Colvin, Jr. in U.S. Pat. No. 6,304,766 disclosed optical-based sensing devices, especially for in-situ sensing in humans.

Patents of interest include but are not limited to:
Russell, U.S. Pat. No. 5,137,833 (1992)
James et al, U.S. Pat. No. 5,503,770 (1996)
Russell & Zepp, U.S. Pat. No. 5,512,246 (1996)
Van Antwerp et al, U.S. Pat. No. 6,002,954 (1999)
Van Antwerp and Mastrototaro, U.S. Pat. No. 6,011,984 (2000)

Related U.S. patents of interest include:
Wolfbeis et al, U.S. Pat. No. 4,586,518 (1986)
Gallop & Paz, U.S. Pat. No. 4,659,817 (1989)
Yafuso & Hui, U.S. Pat. No. 4,798,738 (1989)
Yafuso & Hui, U.S. Pat. No. 4,886,338 (1989)
Saaski et al, U.S. Pat. No. 5,039,491 (1991)
Lanier et al, U.S. Pat. No. 5,114,676 (1992)
Wolfbeis et al, U.S. Pat. No. 5,232,858 (1993)
Colvin, U.S. Pat. No. 5,517,313 (1996)
Sundrehagen et al, U.S. Pat. No. 5,631,364 (1997)
James et al, U.S. Pat. No. 5,763,238 (1998)
Siegmund et al, U.S. Pat. No. 5,711,915 (1998)
Bamard & Rouilly, U.S. Pat. No. 5,852,126 (1998)
Colvin, U.S. Pat. No. 5,894,351 (1999)
Alder et al, U.S. Pat. No. 5,922,612 (1999)
Arnold et al, U.S. Pat. No. 6,063,637 (2000)
Song et al, U.S. Pat. No. 6,046,312 (2000)
Kimball et al, U.S. Pat. No. 6,139,799 (2000)
Clark et al., U.S. Pat. No. 6,040,194 (2000)
Schultz, U.S. Pat. No. 6,256,522 (2001)
Walt, et al., U.S. Pat. No. 6,285,807 (2001)
Colvin U.S. Pat. No. 6,304,266 (2001)
Van Antwerp, et al., U.S. Pat. No. 6,319,540 (2001)
Related articles and publications of interest include:
Yoon & Czarnik, *J. Amer. Chem. Soc.* (1992) 114, 5874-5875
James, Linnane, & Shinkai, *Chem. Commun.* (1996), 281-288
Suenaga et al, *Tetrahedron Letters* (1995), 36, 4825-4828
Eggert et al, *J. Org. Chem.* (1999), 64, 3846-3852
Wolfbeis et al, *Analytica Chimica Acta* (1995), 304, 165-170
Wang et al, *Organic Letters* (1999), 1, 1209-1212
Chen et al, *Proc. Nat. Acad. Sci.* (1999), 96, 12287-12292
P. D. Hale et al, *Analytica Chimica Acta* (1999), 248, 155-161
A. E. Colvin, Jr. et al, *Johns Hopkins Technical Digest*, Vol. 12, #17, p. 378 (1996)
Cappucio, et al., J. Fluorescence, 2004, 14, 521-533.
Camara et al., Tetrahedron Letters, 2002, 43, 1139-141.
Suri, et al., Angewandte Chemie Int. Ed., 2003, 42, 5857-5859.
Suri, et al., *Langmuir,* 2003, 19, 5145-5152.
References of a general nature include:
A. W. Czarnik (ed), *Fluorescent Chemosensors for Ion and Molecule Recognition*, ACS Washington, D.C. 1992.
F. W. Scheller et al (eds), *Frontiers in Biosensorics I Fundamental Aspects*, Birkhauser Verlag, Basel 1997.
J. R. Lakowicz, *Principles of Fluorescence Spectroscopy.* 2nd ed. Kluwer Academics/Plenum Publishers, New York, N.Y. (1999).
Haugland, R. P. *Handbook of Fluorescent Probes and Research Chemicals* 6$^{th}$ ed. Molecular Probes Inc. Eugene, Oreg. (1996).
Gunter Wulff, et al., "Molecular Imprinting for the Preparation of Enzyme Analogous Polymers", pp. 10-28 in R. A. Bartsch and M. Maeda (eds) *Molecular and Ionic Recognition with Imprinted Polymers*. ACS Symposium 703 American Chemical Society 1998. Washington, D.C.
H. Murakami, et al, "Glucose Detection by Electrochemical Methods Using a Viologen Boronic Acid Derivative", *Chem. Letters* (Japan), (2000) (8) p. 940-1.
Some references concerning the technology of the quantum dots include:
D. Ishii, et al., *Nature* 2003, 423, 628-632.
D. Larson, et al., *Science* 2003, 300, 1434-1436.

W. C. Chan, et al., *Current Opinion in Biotechnology* 2002, 13, 40-46.

W. C. Chan, et al., *Science* 1998, 281, 2016-2018.

C. Niemeyer, *Angewandte Chemie-International Edition* 2001, 40, 4128-4158.

M. Bruchez, et al., *Science* 1998, 28 I, 2013-2016.

S. L. Dgunov, et al., *Journal of Physical Chemistry* A 1995, 102, 5652-5653.

Y. Nosabi, et al., *J Phys Chem* 1988, 92, 255-256.

D. Duonghong, *J. Am. Chem Soc,* 198 L 103, 4685-4690.

C. Landes, et al., *Journal of Physical Chemistry* 11 2001, 105. 29X!-29&6.

K. M. Gattas-Asfina et al., Immobilization of Quantum Dots in the Photo Crosslinked Poly(ethylene glycol)-based Hydrogel, *J. Phys. Chem.* B, 2003, 104, 10464-69.

All patents, articles, references, standards and the like cited in this application are incorporated herein by reference in their entirety.

All of these prior art sensors are deficient in one or more aspects, such as operability under physiological conditions, stability of operation, simplicity of design, reliability, implantability, and sensitivity. The present invention overcomes these deficiencies.

SUMMARY OF THE INVENTION

This present invention concerns an optical method and an optical device for determining the concentration of polyhydroxyl compounds in aqueous media, especially for determining in vivo, especially sugars such as glucose or fructose, in physiological media. These compounds, the analytes, are in a system with a fluorescence sensing device comprised of a light source, a detector, and the active components including a fluorophore D (fluorescent dye and the like), a quencher and an optional polymer matrix M. Some components are inventions in their own right. When excited by light of appropriate wave length, the fluorophore emits light (fluoresces). The intensity of the light is dependent on the extent of quenching. The fluorophore and quencher Q are preferably independent entities, optionally they are immobilized in or covalently attached to a polymeric matrix which is permeable to or in contact with the compounds of interest to be detected and quantified.

In one aspect, the present invention comprises a class of fluorescence quenching compounds that are responsive to the presence of polyhydroxyl compounds such as glucose in aqueous media at or near physiological pH. In other words, the quenching efficiency is controlled by the concentration of these compounds in the medium. The quencher is comprised of a viologen substituted with at least one boronic acid group wherein the adduct is immobilized in or covalently bonded to a polymer. The quencher, dye and polymer may also be covalently bonded to each other.

The combination of boronic acid and viologen, and the resultant effect on viologen properties are important embodiments of the present invention.

In another aspect, the present invention is a class of polymeric fluorescent dyes which are susceptible to quenching by the viologen/boronic acid adduct. Useful dyes include pyranine derivatives (e.g. hydroxypyrene trisulfonamide derivatives and the like) and derivatives of aminopyrene trisulfonic acid. (See FIGS. 1A, 1B, 1C and 17), In one embodiment, the dye is comprised of a hydroxypyrene trisulfonamide moiety bonded to a polymer. Converting sulfonic acid groups to sulfonamide groups shifts the pKa of pyranine into a range more suitable for measurement at physiological pH. This conversion also shifts the absorbance of the dye to longer wavelengths thereby allowing it to be more efficiently excited by light from a blue LED, which is a preferred light source for an implanted sensor. These derivatives are typically prepared by reacting a trisulfonyl chloride intermediate with 1) a polyamine, 2) an amine functional ethylenically unsaturated monomer, which adduct is subsequently polymerized, 3) or an amine functional polymer. In one embodiment, the dye is a fully substituted derivative having no residual free sulfonic acid groups on the pyrene ring.

In another aspect, the present invention is a composite water-compatible polymer matrix, preferably a hydrogel, which comprises the dye and quencher moieties. The matrix is a water-swellable copolymer, preferably crosslinked, to which the dye and quencher moieties are covalently bonded by a linking group L. In one embodiment, the matrix is an interpenetrating polymer network (IPN) with the dye incorporated in one polymer network and the quencher in the other polymer network. In another embodiment, the matrix is a semi-IPN wherein the dye component is a high molecular weight water-soluble or dispersible polymer trapped in a crosslinked network comprised of quencher monomer and suitable hydrophilic comonomers. Optionally, the quencher may be in the water-compatible or dispersible component and the dye within the network. Further both dye and quencher may be separately incorporated in water-soluble or dispersible polymers wherein dye and quencher are both trapped in an inert polymer matrix. Optionally, the components are separated from the analyte solution by a membrane which is impermeable to the components, but permeable to the analyte. Optionally, the matrix is molecularly imprinted to favor association between dye and quencher, and to enhance selectivity for specific sugars, e.g. glucose, over other polyhydroxy compounds. The preferred method for enhancing interaction between dye and quencher is to functionalize the dye moiety with negatively charged groups such as carboxylate, sulfonate, phosphonate, and phosphate.

In another aspect, the present invention concerns a device for measuring the concentration of glucose in vivo by means of an optical sensor. The specific device is comprised of a visible light source, preferably a blue LED light source, a photodetector, a light conduit (optical wave guide) such as an optical fiber assembly, and a water-insoluble polymer matrix comprised of a fluorophore susceptible to quenching by a viologen, a viologen/boronic acid quencher, and a glucose permeable polymer, wherein the matrix is in contact with said conduit and with the medium containing the analyte.

In another aspect, the present invention relates to a method for optically determining the concentration of an analyte in a sample, which method comprises:
  contacting the analyte sensor described herein with the sample;
  applying light to the sensor;
  detecting emitted light; and
  determining the concentration of the analyte.

In another embodiment, the present invention relates to a device for optically determining an analyte concentration, which device comprises:
  an analyte permeable component;
  a fluorophore associated with the analyte permeable component and configured to absorb light at a first wavelength and emit light at a second wavelength;
  a quencher associated with the analyte permeable component and configured to modify the light emitted by the fluorophore by an amount related to the analyte concentration, wherein the quencher comprises a boronic acid substituted viologen;
  a light source; and
  a detector. Preferably the fluorophore is capable of being quenched by viologen, and the fluorophore and quencher are in close proximity and each is associated with or immobilized by the analyte permeable component.

In another embodiment the present invention relates to an optical method for the in vivo detection of polyhydroxyl-substituted organic molecules as the analyte between about 400 and 800 nm, preferably 430 to 800 nm detection, which method comprises:

A. obtaining a fluorophore dye D, which is compatible with the analyte solution, wherein D is selected from:
(a) $D^1$ which is a fluorophore dye having the properties of
i. A fluorophore,
ii. An excitation in the range greater than 400 nm and less than 800 nm,
iii. Resistant to photobleaching under the conditions of analysis,
iv. A Stokes shift of about or greater than 30 nm,
v. Compatibility with said analyte solution, and wherein said
vi. Dye $D^1$ is quenched by methyl viologen to produce an experimentally determined apparent Stern-Volmer quenching constant (Ksv) greater than or equal to 50,
wherein the fluorophore dye $D^1$ which is neutral or negatively charged is:
(i) a discrete compound having a molecular weight of 1,000 daltons or greater, with the proviso that if the dye is substituted with negatively charged groups the molecular weight is 500 daltons or greater;
(ii) a pendant group or chain unit in a water-soluble or dispersible polymer having a molecular weight greater than about 10,000 daltons, and
optionally said polymer is non-covalently associated with a water-insoluble polymer matrix $M^1$ and is physically immobilized within said polymer matrix $M^1$ wherein said polymer matrix $M^1$ is permeable to or in contact with said analyte solution; and
optionally where $D^1$ is negatively charged and the polymer is immobilized as a complex with a cationic water-soluble polymer, said complex formed is permeable to or in contact with said analyte solution;
(b) $D^2$ is a fluorophore dye having the properties of
i. A fluorophore,
ii. An excitation in the range greater than 400 nm and less than 800,
iii. A Stokes shift of about or greater than 30 nm,
iv. Resistant to photobleaching under the conditions of analyses,
v. Compatibility in the analyte solution, and wherein
vi. Said Dye $D^1$ is quenched by methyl viologen to produce an apparent Stern-Volmer quenching constant (Ksv) greater than or equal to 50, wherein D1 is covalently bonded to an insoluble polymer matrix $M^1$ wherein said polymer matrix $M^1$ is permeable to or in contact with said analyte; wherein said fluorophore dye $D^1$ is a part of the structure: $M^1$-$L^1$-$D^2$ with the proviso that $D^2$ which is polyfunctional is bonded to matrix $M^1$ at one, two or three sites;
$L^1$ is a hydrolytically stable covalent linking group selected from the group consisting of a direct bond, lower alkylene having 1 to 8 carbon atoms optionally ten-ninated with or including one or more divalent connecting groups selected from sulfonamide, amide, ester, ether, sulfide, sulfone, phenylene, urethane, urea, and amine, and
B. Combining with a boronic acid-containing quencher moiety Q, wherein Q is comprised of a conjugated nitrogen-containing heterocyclic, aromatic bis-onium salt having the properties of compatibility in said analyte solution and produces a detectable change in the emission of the dye in the presence of said analyte, selected from:
(i) quencher $Q^1$ which is a discrete compound having a molecular weight of about 400 daltons or greater or is a pendant group or a chain unit in a water-soluble or water-dispersible polymer having a molecular weight greater than 10,000 daltons and said polymer optionally is non-covalently associated with the optional polymer matrix $M^1$ when present, and is physically immobilized in said polymer matrix, or optionally said polymer is immobilized as a complex with a negatively charged water-soluble polymer, or
(ii) quencher $Q^2$ which is covalently bonded by linking group $L^2$ to $M^1$ or to a second water insoluble polymer matrix $M^2$ producing $M^2$-$L^2$-$Q^2$ wherein $L^2$ is selected from the group consisting of a direct bond, a lower alkylene having 1 to 8 carbon atoms optionally terminated with or including one or more divalent connecting groups selected from sulfonamide, amide, quaternary ammonium, pyridinium, ester, ether, sulfide, sulfone, phenylene, urea, thiourea, and urethane, or amine, wherein said quencher $Q^1$ or $Q^2$ is mixed at a molecular level with said fluorophore dye $D^1$ or $D^2$, and with the proviso that $Q^2$ when polyfunctional is linked to the matrix $M^2$ at one or two sites,
C. contacting a physiological fluid which contains analyte, a dye and a quenched in vivo with an excitation light source coupled with a detector;
D. producing a detectable and quantifiable signal in the range of about 400 to 800 nm; and
E. determining the concentration of said polyhydroxyl-substituted analyte in said physiological fluid.

In another embodiment, the invention is a device which incorporates the components listed above which work together to determine the analyte.

In the present invention, the term "polymer" to which $D^1$ and $D^2$ are attached excludes those polymers which react or combine with dihydroxy compounds. The useful polymers may be anionic, cationic or non-ionic, and are hydrolytically stable and compatible with in vivo fluid.

In one aspect, this invention is a class of fluorescence quenching compounds that are responsive to the presence of poly hydroxy compounds such as glucose in aqueous media; i.e., the quenching efficiency is controlled by the concentration of said compounds in the medium. The fluorophore may be fluorescent organic dye, a fluorescent organometallic compound or metal chelate, a fluorescent conjugated polymer, a fluorescent quantum dot or nanoparticle or combinations. When said quenchers are combined with a fluorophore, they are useful for measuring the concentration of glucose in physiological fluid, such as blood. The quencher is comprised of a viologen substituted with two or more boronic acid groups. In one embodiment, the quencher is comprised of a viologen derived from 3,3'-dipyridyl substituted on the nitrogens with ortho benzyl boronic acid groups, said adduct optionally containing one or more additional cationic groups, said adduct preferably being covalently bonded to a polymer. The receptor that provides glucose recognition is an aromatic boronic acid. The boronic acid of this invention is bonded to a viologen and reacts reversibly with glucose in blood or other body fluids, in the pH range of about 6.8 to 7.8 and at body temperature to form boronate esters, the extent of reaction being related to glucose concentration in the medium, over the concentration range from about 50 to greater than 400 mg/dl. Preferably, two or more boronic acid groups are attached to the viologen molecule and spaced to allow cooperative binding to glucose. The fluorophore and quencher are incorporated into a hydrogel or are confined by a membrane sufficiently permeable to glucose to allow equilibrium to be established in less than 10 minutes. The viologen-boronic acid moiety can be a unit in the polymer backbone or a pendant group on the polymer chain. Optionally, it can be attached to a surface; e.g. as a self-assembled monolayer or multilayer. In another aspect, this invention is a polymer matrix, preferably a hydrogel, which comprises the fluorophore and quencher moieties. The matrix is a water soluble or swellable copolymer, preferably crosslinked, to which the fluorophore and quencher moieties are covalently bonded; more preferably the matrix is an interpenetrating polymer network (IPN) with the fluorophore incorporated in one polymer network and the quencher in the other. Optionally, the matrix is molecularly imprinted to favor association between fluorophore and quencher, and to enhance selectivity for glucose over other poly hydroxy compounds. Monomers useful for making said matrix include hydroxyethyl methacrylate, hydroxy ethyl acrylate, acrylamide, and N,N-dimethyl acrylamide, and the like. A typical synthesis of the viologen and the sensing polymer and a demonstration of glucose sensing is provided herein.

In another aspect, this invention is a device for measuring the concentration of glucose in blood in vivo, said device being comprised of an LED light source, a photodetector, a light conduit such as an optical fiber, and a polymer matrix comprised of a fluorophore susceptible to quenching by a viologen, an ortho benzyl boronic acid substituted viologen quencher, and a glucose permeable polymer, said matrix being in contact with said conduit and with the medium containing the analyte. Typically said sensor is incorporated into a catheter for insertion into a blood vessel.

In another aspect of the method, the Dye $D^1$ is selected from a discrete molecule or polymer of pyranine derivatives having the structure of:

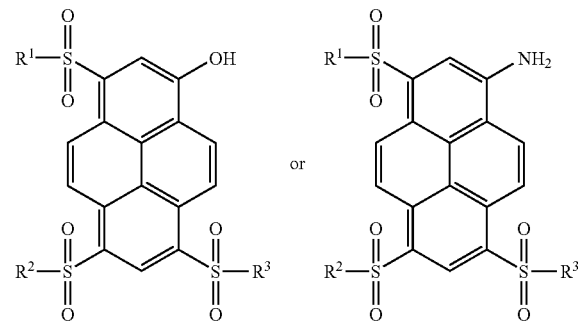

where $R^1$, $R^2$ and $R^3$ are each —NH—CH$_2$—CH$_2$(—O—CH$_2$—CH$_2$)$_n$—X$^1$;
wherein $X^1$ is selected from —CH$_2$—OCH$_3$, —CO$_2$H, —CONH$_2$, —SO$_3$H, or —NH$_2$;
and n is between about 70 and 10,000, and preferably between 100 and 1,000.

In another aspect of the method, the Dye $D^1$ or $D^2$ is prepared from pyranine derivatives having the structure of:

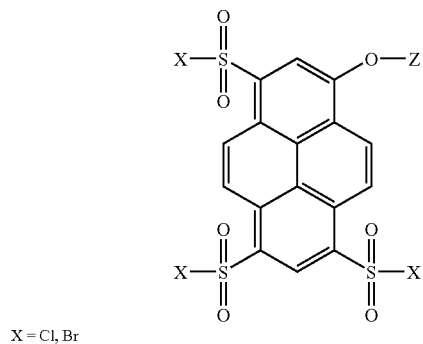

X = Cl, Br or from a dye monomer selected from the group consisting of:

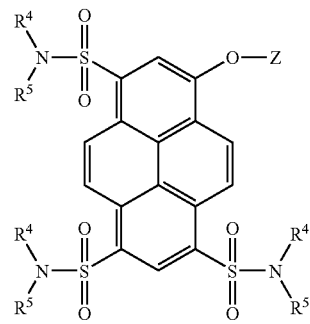

where $R^4$=—H, and
$R^5$ is selected from: —R$^6$—NH—(C=O)—(C=CH$_2$)—R$^7$, —R$^6$—O—(C=O)—(C=CH$_2$)—R$^7$, —CH$_2$—C$_6$H$_4$—CH=CH$_2$— or —CH$_2$—CH=CH$_2$—
where in $R^6$ is a lower alkylene of 2 to 6 carbons and $R^7$=—H, or —CH$_3$
where Z is a blocking group that is removed by hydrolysis selected from:

—(C=O)—R$^8$—Y where $R^1$ is a lower alkylene of 1 to 4 carbon atoms and
Y is selected from —H, —OH, —CO$_2$H, —SO$_3$H, —(C=O)—NH—R$^9$, or —CO$_2$—R$^9$ where
$R^9$ is a lower alkylene of 1 to 4 carbon atoms.

Preferably a dye moiety $D^1$ as a discrete compound or a pendant group is selected from:

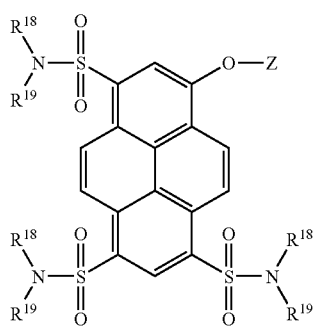

where $R^{18}$ is —H or L$^3$-A where L$^3$ is selected from L$^2$ above and A is selected from —COOH and —SO$_3$H; and
$R^{19}$ is —H or is selected from R$^5$ above with the proviso that when the dye is $D^2$ at least one of $R^{18}$ or $R^{19}$ is a polymerizable group and each sulfonamide group is substituted with one —H.

In another aspect, $Q^1$ is a discrete compound with a molecular weight (MW) at least twice the MW of the analyte which is water soluble or dispersible having at least one boronic acid substituent wherein said compound is isolated from the body by a semi-permeable membrane. Preferably $Q^1$ as a discrete compound contains two boronic acid substituents.

In another aspect the quencher $Q^1$ is selected from:

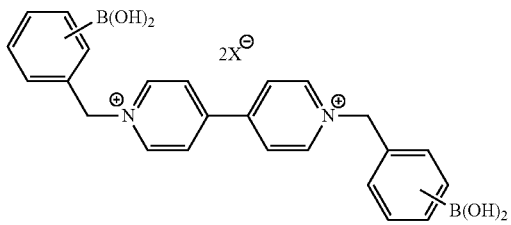

with the proviso that for above structure no ortho derivatives are included,
and from:

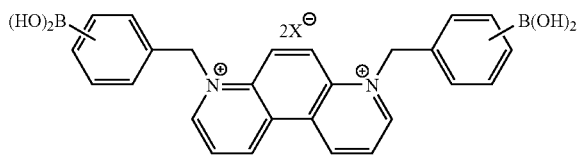

wherein the boronic acid groups are in the meta- or para-positions.

In another aspect of the method, the quencher $Q^1$ or $Q^2$ is prepared from a quencher precursor selected from the group consisting of o-, m-, and p-boronic acids:

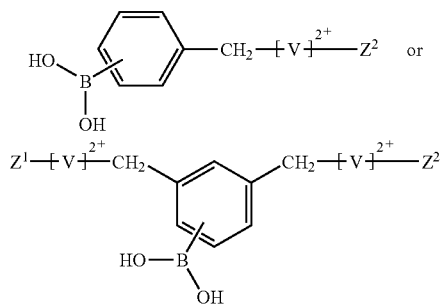

where $(V)^{2+}$ is a nitrogen containing conjugated heterocyclic aromatic group selected from isomers of dipyridyls, dipyridyl ethylenes, dipyridyl phenylenes, phenanthrolines, or diazafluorenes; wherein the two nitrogen atoms are each in a different aromatic ring and the nitrogens are in all positions capable of forming an onium salt and where $Z^1$ or $Z^2$ is a substituent on nitrogen and is either a polymerizable ethylenically unsaturated group selected from:

(i) $-R^{10}-CO_2-C(R^{11})=CH_2$, $-R^{10}-NH-(C=O)-C(R^2)=CH_2$, or $-CH_2-C_6H_4-CH=CH_2$, here $R^{10}$ is a lower alkylene or hydroxyalkylene of 2 to 6 carbon atoms and where $R^{11}=-H$ or $-CH_3$; or (ii) a coupling group selected from: $-R^{12}-Z^3$
where $R^{12}$ is $-CH_2C_6H_4-$ or alkylene of 2 to 6 carbon atoms and
$Z^3$ is $-OH$, $-SH$, $-CO_2H$, or $-NH_2$.

$Q^1$ is a discrete compound or a pendant group or a chain unit (linear or branched) of a water-soluble or dispersible polymer. The insoluble polymer matrix $M^1-L^2-Q^2$ is preferably a crosslinked network polymer.

In another aspect, $Q^1$ or $Q^2$ is prepared from a precursor selected from:

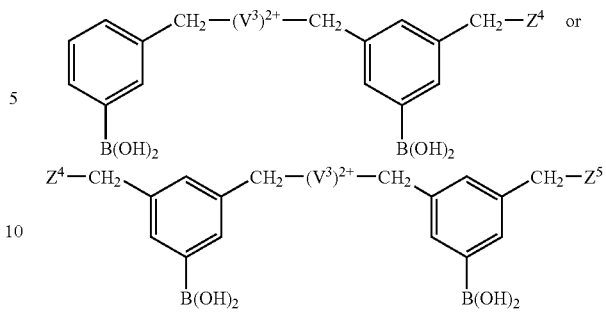

where $V^3$ and $Z^4$ or $Z^5$ are 2, 3 or 4-(CH=$CH_2$)-pyridinium; $-N-(CH_2)_w-O(C=O)C(CH_3)=CH_2$); $-O-(CH_2)_w$, $-O-CH_2-(CH=CH_2)$; $-O-(CH_2)_w-O-(C=O)CH$ (=$CH_2$); and $-O-(CH_2)_w-O-(C=O)C(CH_3)=CH_2$; and w is a integer from 2 to 6, or $Z^4$ and $Z^5$ have the same definitions as above for $Z^1$ and $Z^2$.

For the dye D, note that $D^1$ and $D^2$ are defined with the proviso that the dye $D^1$ and $D^2$ do not include a diazo linkage $-N=N-$.

For the quencher Q, $Q^1$ and $Q^2$ are defined with the proviso that the quencher $Q^1$ and $Q^2$ do not include a diazo linkage $-N=N-$.

For the in vivo applications, described herein, the ortho-benzylboronic acid derivatives of 4,4'-dipyridyl in the presence of a polymer are excluded.

BRIEF DESCRIPTION OF THE FIGURES

FIG. 2A is trans-1,2-bis(4,4'-N,N'-(benzyl-4-boronic acid)-pyridinium)ethylene dibromide;

FIG. 2B is 1,7-N,N'-bis(benzyl-3-boronic acid)-phenanthrolinium dibromide;

FIG. 2C is benzyl viologen (BV)-a comparative quencher;

FIG. 2D is 4,4'-N,N'-bis-(benzyl-2-boronic acid)-dipyridinium dibromide (oBBV);

FIG. 2E is 4,4'-N,N'-bis-(benzyl-3-boronic acid)-dipyridinium dibromide (mBBV);

FIG. 2F is 4,4'-N,N'-bis-(benzyl-4-boronic acid)-dipyridinium dibromide (pBBV);

FIG. 2G is N,N'-bis(benzyl-(2, 3, or 4)-boronic acid-4,7-phenantholinium halide (4,7-phen-o, m, or p-BBV);

FIG. 3A is 4-N-(benzyl-2-boronic acid)-4'-N'-(benzyl)-dipyridinium bromide chloride;

FIG. 3B is 4-N-(benzyl-3-boronic acid)-4'-N'-(benzyl-4-ethenyl)-dipyridinium bromide chloride (m-SBBV);

FIG. 3C is 4-N-(benzyl-2-boronic acid)-4'-N'-(benzyl-4-ethenyl)-dipyridinium bromide chloride (o-SBBV); and FIG. 3D is 4-N-(benzyl-4-boronic acid)-4'-N'-(benzyl-4-ethenyl)-dipyridinium bromide chloride (p-SBBV).

FIG. 3E is trans-1,2-bis-4-N-(benzyl-4-boronic acid)-4'-N'-(benzyl-4-ethenyl)dipyridinium-4-ethylene dibromide;

FIG. 3F is 4-N-(benzyl-3-boronic acid)-4'-N'-(benzyl-3-ethenyl)-3 phenanthrolinium dibromide;

FIG. 3G is 4,4'-N,N-bis-[benzyl-(3-methylene-4-vinyl-pyridinium bromide)-5-(boronic acid)]-dipyridinium dibromide) (m-BBVBP);

FIG. 3H is 4-N-(benzyl-3-(boronic acid)-7-n-[benzyl-3-(methylene-(1-oxy-3-(oxybenzylvinyl)-propane))-5-boronic acid]-4,7-phenanthrolinium dibromide;

FIG. 3I is 4,4'-N,N-bis-[benzyl-(3-methylene-4-vinylpyridiniumbromide)-5-(boronic acid)]-4,7-phenanthrolinium dibromide;

FIG. 8 is a schematic representation of one embodiment of the in vitro probe as it would be used in a process stream and is also an embodiment illustrating the use of the sensing polymer assembly.

FIG. 9 is a schematic representation of a second embodiment of the in vitro probe as it would be used in a process stream to monitor for polyhydroxyl organic compounds, e.g. glucose or fructose.

FIG. 10 is a schematic cross-sectional representation of the in vitro probe of FIG. 9. It is also a representation of the in vivo sensing polymer assembly of FIG. 9.

DETAILED DESCRIPTION OF THE INVENTION AND PREFERRED EMBODIMENTS

Definitions

Figure 1A:
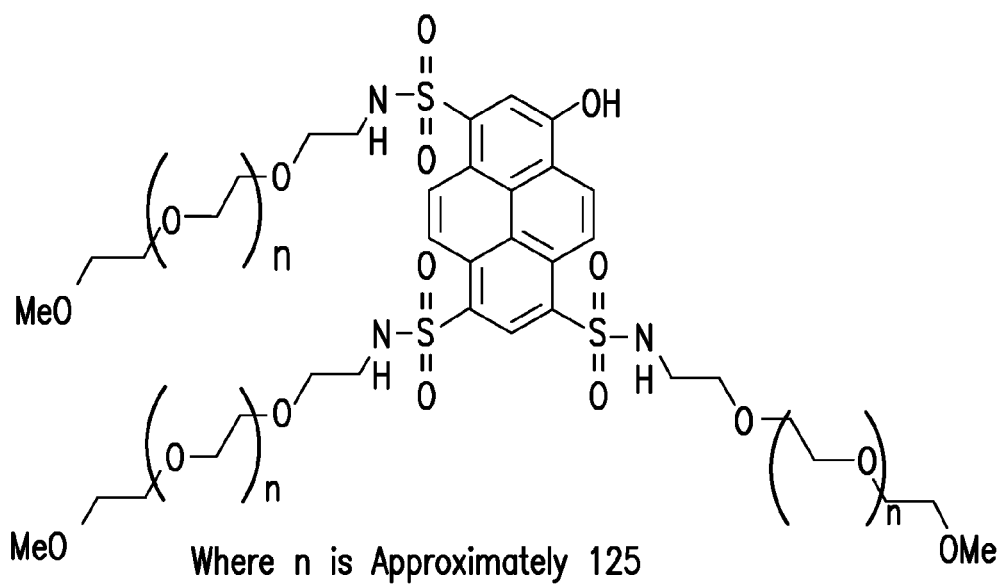
FIG. 1A is the structural formula of (8-hydroxypyrene-1,3,6-N,N',N"-tris-(methoxypolyethoxyethyl (n~125) sulfonamide) (HPTS-PEG).

As used herein:

"Boronic acid" refers to a structure —$B(OH)_2$. It is recognized by those skilled in the art that a boronic acid may be present as a boronate ester at various stages in the synthesis of the quenchers of this invention. Boronic acid is meant to include such esters.

"Detector" refers to a device for monitoring light intensity such as a photo diode.

"Fluorophore" refers to a substance that when illuminated by light at a particular wavelength emits light at a longer wavelength; i.e. it fluoresces. Fluorophores include organic dyes, organometallic compounds, metal chelates, fluorescent conjugated polymers, quantum dots or nanoparticles and combinations of the above. Fluorophores may be discrete moieties or substituents attached to a polymer. "Fluorescent dye" or "dye" is selected from a discrete compound or a reactive intermediate which is convertible to a second discrete compound, or to a polymerizable compound; or D is pendant group or chain unit in a polymer prepared from said reactive intermediate or polymerizable compound, which polymer is water-soluble or water-dispersible or is a water-insoluble polymer, said polymer which is optionally crosslinked.

"Fluorescent conjugated polymers" refers to a polymer in which the structure as a whole behaves as a fluorophore A typical example is polyphenylene vinylene, i.e., a conjugated carbon-carbon double bond is present and conjugation is sufficient for the polymer to have fluorescent properties.

"HEMA" refers to 2-hydroxyethylmethacrylate.

"Light source" or "excitation light source" refers to a device that emits electromagnetic radiation such as a xenon lamp, medium pressure mercury lamp, a light emitting diode (LED) all of which are commercially available.

"Linking group" refers to L, $L^1$ or $L^2$ which are divalent moieties, that covalently connect the sensing moiety to the polymer or matrix. Examples of L, $L^1$ or $L^2$ include those which are each independently selected from a direct bond or, a lower alkylene having 1 to 8 carbon atoms, optionally terminated with or interrupted by one or more divalent connecting groups selected from sulfonamide (—$SO_2NH$—), amide —(C=O)N—, ester —(C=O)—O—, ether.O—, sulfide —S—, sulfone (—$SO_2$—), phenylene —$C_6H_4$—, urethane —NH(C=O)—O—, urea —NH(C=O)NH—, thiourea —NH(C=S)—NH, amide —(C=O)NH—, amine-NR— (where R is defined as alkyl having 1 to 6 carbon atoms) and the like.

"Quencher" refers to a compound that reduces the emission of a fluorophore when in its presence. Quencher Q is selected from a discrete compound, a reactive intermediate which is convertible to a second discrete compound or to a polymerizable compound or Q is a pendant group or chain unit in a polymer prepared from said reactive intermediate or polymerizable compound, which polymer is water-soluble or dispersible or is an insoluble polymer, said polymer is optionally crosslinked.

"Quantum dots" refers to when electrons and holes in material are confined to ultra-small regions of space (typically 1-25 nm), the material structure enters the regime of size quantization, wherein the electronic energy levels of the system become discrete rather than quasi-continuous, and the optical and electronic properties of the materials become strongly size-dependent. Such structures are termed quantum dots or nanocrystals, quantum rods, or quantum wells depending upon their shape and dimensionality of the quantum confinement. They include semiconductor crystals with a diameter of a few nanometers typically surface treated with functional groups to make them water-dispersible.

"In vivo" refers to analysis in a living mammal, preferably a human being. In vivo measurements take place under physiological conditions of temperature, pressure, medium, analyte concentration and pH as found in a human body.

"IPN" or "interpenetrating polymer network" refers to a combination of two or more network polymers synthesized in juxtaposition (see L. H. Sperling, Interpenetrating Polymer Networks, ACS Advances in Chemistry Series 239, 1994, from Aug. 25-30, 1991 New York ACS Meeting).

"Pyridinium" refers to structures (linking groups or pendant groups comprised of units, i.e. pyridine rings substituted on the nitrogen and optionally on carbons in other positions on the ring. Substituents on carbon include vinyl groups and substituents on nitrogen include the methylene group of a benzyl boronic acid.

"Semi-IPN" or semi-interpenetrating polymer network" refers to a combination of polymers in which one component is soluble and the other polymer is a network (see Sperling above).

"Onium" refers to a heteroaromatic ionic compound having a formal positive charge on the heteroatom, which in the case of viologen is a nitrogen.

"PEG" or "polyethylene glycol" refers to polymer or chain segments, which contain oxyethylene (—$OCH_2$—$CH_2$—) repeating units.

"PEGDMA" refers to polyethylene glycol terminated with two methacrylate groups.

"PEGMA" refers to polyethylene glycol terminated with one methacrylate group.

"Physiological pH" refers to the pH range of 7.3-7.5 normally existing in the blood of a healthy living human being. In critically ill patients, a physiological pH between about 6.8 to 7.8 is often observed.

"Visible light range" refers to light in the spectrum between about 400 and 800 nm.

"Viologen" refers generally to compounds having the basic structure of a nitrogen containing conjugated N-substituted heterocyclic aromatic bis-onium. salt, such as 2,2'-, 3,3'- or 4,4'-N,N' bis-(benzyl) bipyridium dihalide (i.e., dichloride, bromide chloride), etc. Viologen also includes the substituted phenanthroline compounds.

The present invention concerns a number of important advances. These include but are not limited to a method and an in vivo device for determining carbohydrate, 1,2-diol or 1,3-diol levels in liquids selected from aqueous or organic liquids or combinations thereof or in a physiological fluid, respectively. A series of fluorophore dyes, a series of boronic acid substituted quenchers, and combinations of interacting water-compatible and water-soluble and organic solvent-compatible and organic solvent-soluble organic polymers are used. These aspects are discussed in more detail below. The components are discussed first, and their combination to produce the method and the device follows.

Quencher

The moiety that provides glucose recognition in the present invention is an aromatic boronic acid. More specifically, the boronic acid of this invention is covalently bonded to a conjugated nitrogen-containing heterocyclic aromatic bis-onium structure, e.g. a viologen, (see for example FIGS. 3A to 3I) in which the boronic acid has a pKa less than about 8, preferably less than about 7, and reacts reversibly with glucose in aqueous media to form boronate esters. The extent of reaction is related to glucose concentration in the medium.

Bis-onium salts of this invention are prepared from conjugated heterocyclic aromatic dinitrogen compounds. The conjugated heterocyclic aromatic dinitrogen compounds are selected from dipyridyls, dipyridyl ethylenes, dipyridyl phenylenes, phenanthrolines, and diazafluorenes, wherein the nitrogen atoms are in a different aromatic ring and are able to form an onium salt. It is understood that all isomers of said conjugated heterocyclic aromatic dinitrogen compounds in which both nitrogens can be substituted are useful in this invention. Bis-onium salts derived from 4,4'-dipyridyl and 4,7-phenanthrolines are included. The viologen boronic acid adducts are discrete compounds or are water-compatible pendant groups or units in a chain of a water-soluble or water-dispersible polymer with a molecular weight greater than 10,000 or are bonded to an insoluble polymer matrix. One or more boronic acid groups are attached to the viologen moieties.

For the polymeric quencher precursors, multiple options are available for the boronic acid moiety to be attached to two different nitrogens in the heteroaromatic centrally located group. These are:

a) a polymerizable group on a first aromatic moiety is attached to one nitrogen and a second aromatic group containing at least one —$B(OH)_2$ group is attached to the second nitrogen;

b) one or more boronic acid groups are attached to a first aromatic moiety which is attached to one nitrogen and one boronic acid and a polymerizable group are attached to a second aromatic group which second aromatic group is attached to the second nitrogen;

c) one boronic acid group and a polymerizable group are attached to a first aromatic moiety which first aromatic group is attached to one nitrogen, and a boronic acid group and a polymerizable group are attached to a second aromatic moiety which is attached to the a second nitrogen; and d) one boronic acid is attached to each nitrogen and a polymerizable or coupling groups is attached to the heteroaromatic ring. Preferred embodiments have two boronic acid moieties and one polymerizable group or coupling group.

Representative viologens with one boronic acid group include the following:
1. boronic acid substituted viologen of the structure:

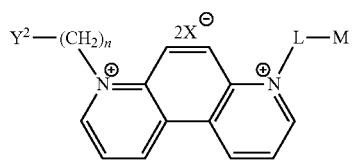

where n=0-3, preferably n is 1, and where L is a linking group, i.e. $L^1$ or $L^2$ as defined herein and M is a polymer matrix as defined herein, and where $Y^2$ is phenyl boronic acid (m- and p-isomers) or naphthyl boronic acid, preferably a phenyl boronic acid, and 2. a substituent on the heterocyclic ring of a viologen.

The viologen is contemplated to include combinations of the above. The precursor from which the viologen/boronic acid is derived is an unsymmetrically substituted viologen, such as with a boronic acid functional group on one end and a polymerizable group, such as a vinyl group, on the other (see FIGS. 3A-3I). The viologen/boronic acid moiety is a pendant group or a chain unit in a water soluble or dispersible polymer, or a unit in a crosslinked, hydrophilic polymer or hydrogel sufficiently permeable to glucose to allow equilibrium to be established. In a preferred embodiments, greater intensities of signals are observed when the viologen comprises two or more boronic acid moieties.

Preferred quenchers $Q^2$ are prepared from precursors comprising viologens derived from 3.3'-dipyridyl substituted on the nitrogens with benzylboronic acid groups and at other positions on the dipyridyl rings with a polymerizable group or a coupling group. Representative viologens include:

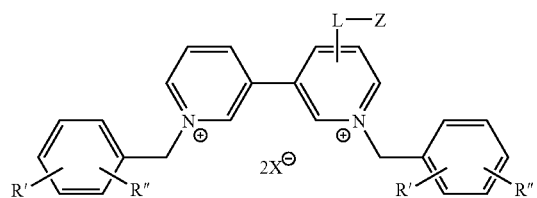

Where L is independently selected from L, $L^1$ or $L^2$ as defined herein, Z is independently selected from $Z^1$, $Z^2$, $Z^3$, $Z^4$ or $Z^5$ as defined herein and R' is —B(OH)$_2$ and R" is a coupling group as is defined herein.

Other examples of novel quencher precursors include:

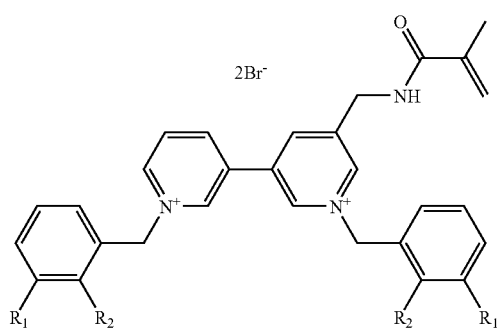

3,3'-oBBV; $R_1$ = H, $R_2$ = B(OH)$_2$
3,3'-mBBV; $R_1$ = B(OH)$_2$, $R_2$ = H

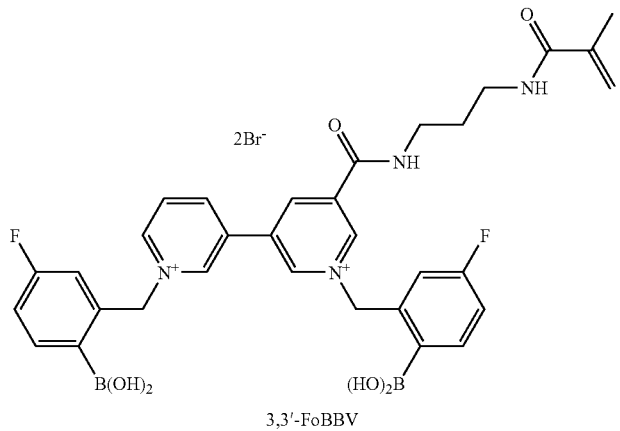

3,3'-FoBBV

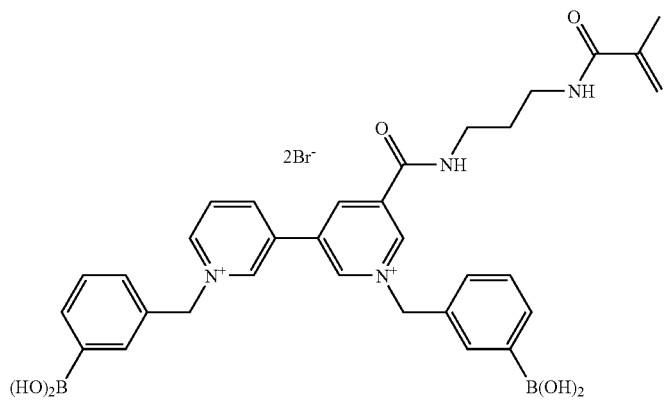

3,3'-mBBV

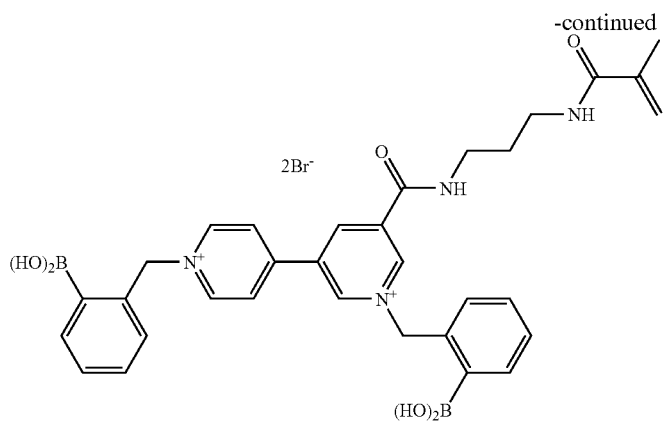
4,3-oBBV

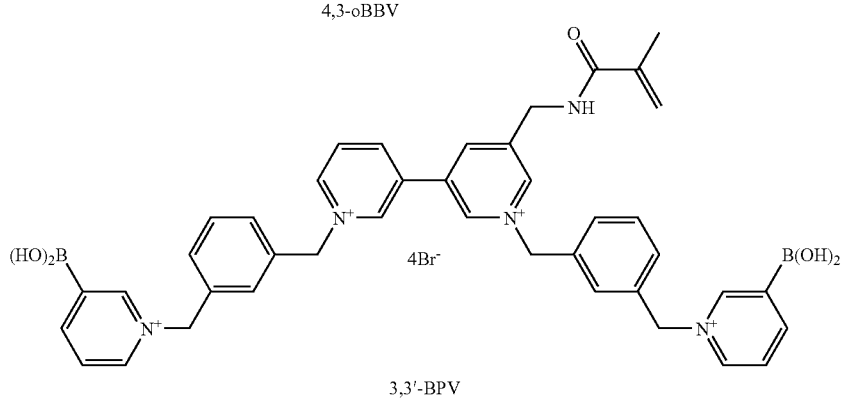
3,3'-BPV

Fluorophore Dye

Figure 1B:
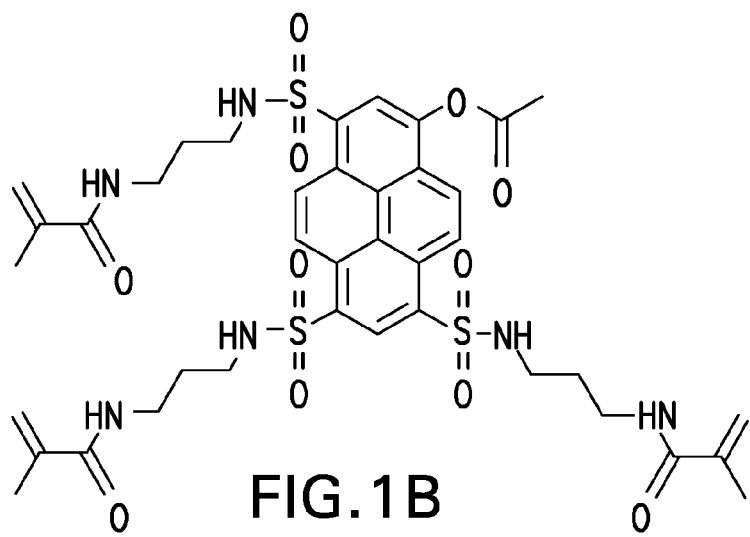
FIG. 1B is the structural formula of 8-acetoxypyrene-1,3,6-N,N',N"-tris-(methacrylpropylamidosulfonamide) (acetoxy-HPTS-MA).
Figure 1C:
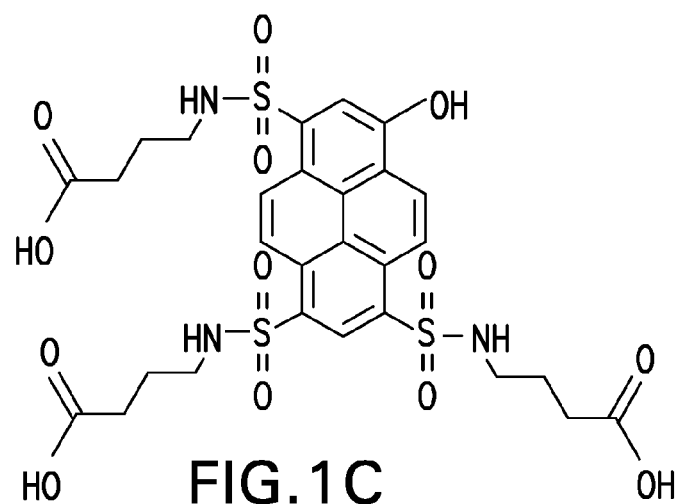
FIG. 1C is the structural formula of 8-hydroxypyrene-1,3,6-N,N',N"-tris(carboxypropylsulfonamide) (HPTS-$CO_2$).
Figure 2A:
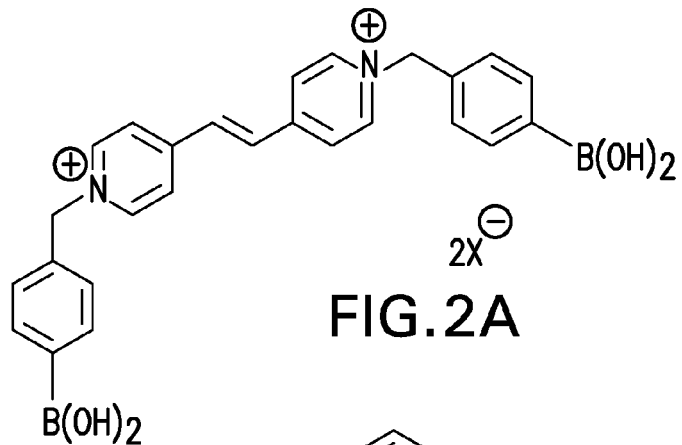
FIGS. 2A to 2G are schematic representations of structures of quenchers $Q^1$ as the dihalide salts.
Figure 2B:
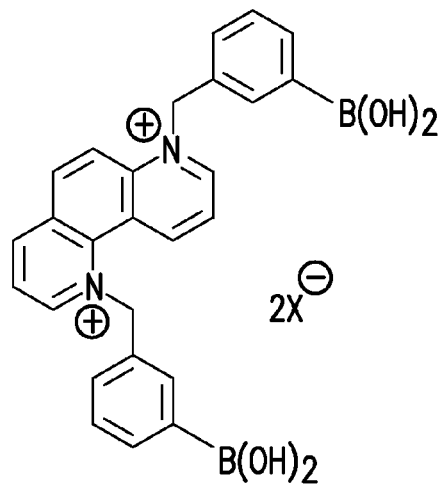
Figure 2C:
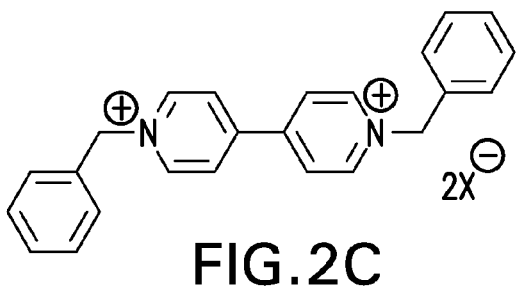
Figure 2D:
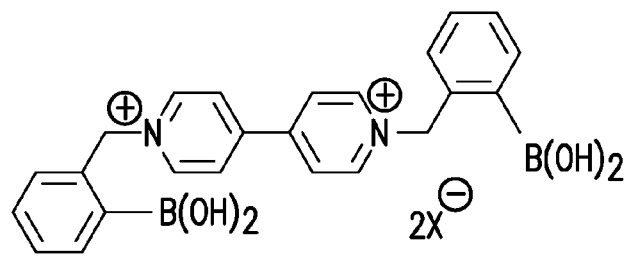
Figure 2E:
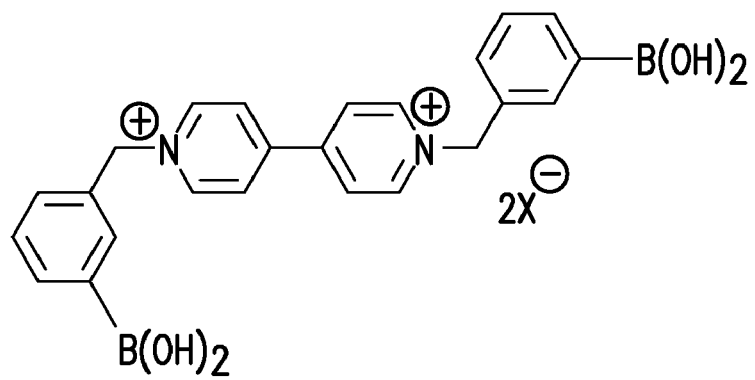
Figure 2F:
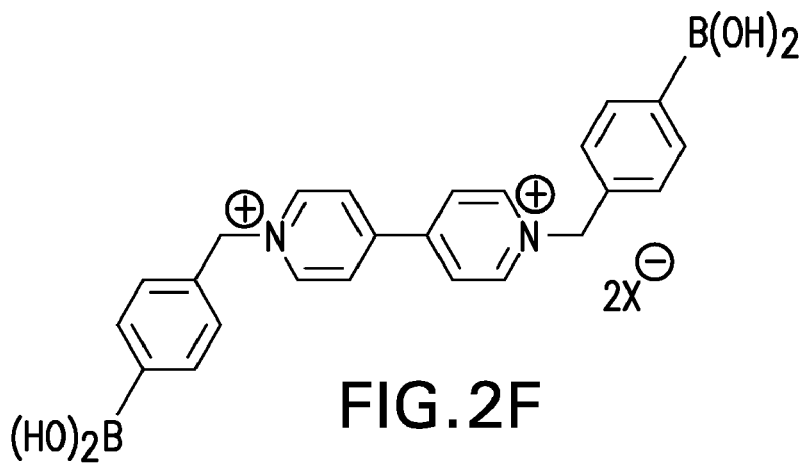
Figure 2G:
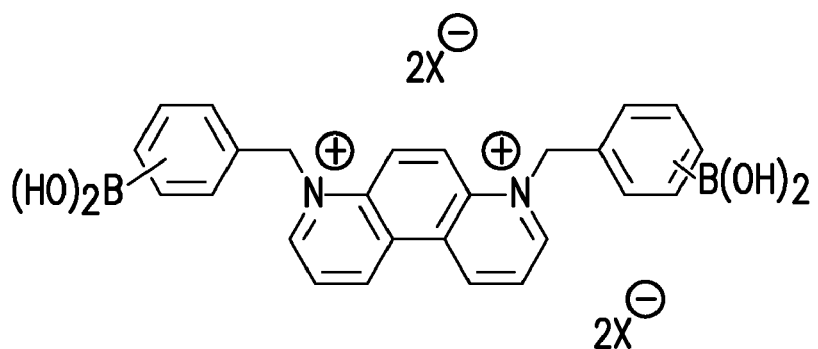
Figure 3A:
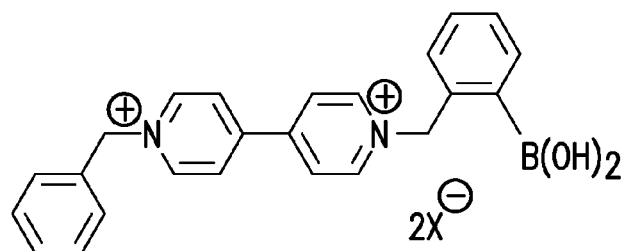
FIG. 3A is an unsymmetrical glucose responsive viologen.
Figure 3B:
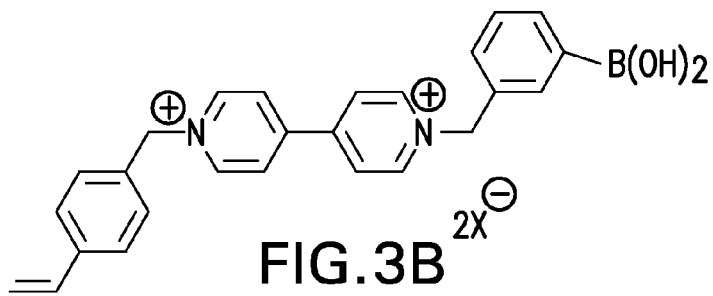
FIGS. 3B to 3I are schematic representations of structures of quencher precursors.
Figure 3C:
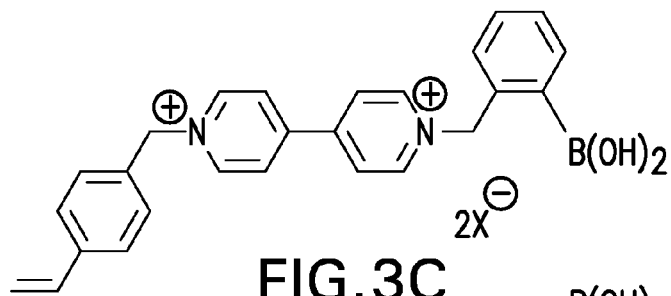
Figure 3D:
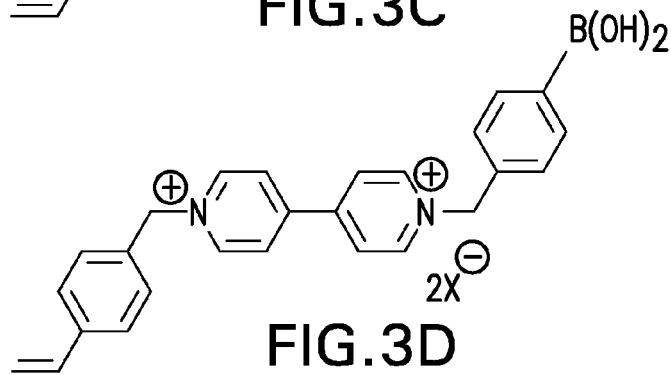
Figure 3E:
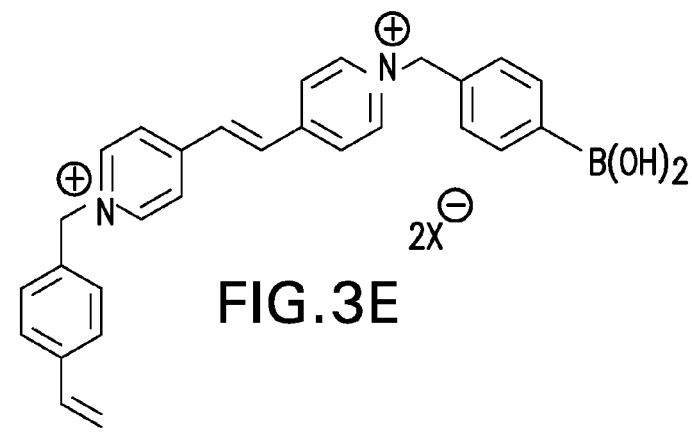
Figure 3F:
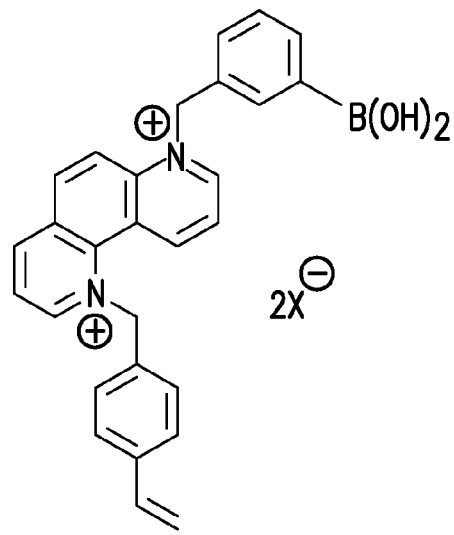
Figure 3G:
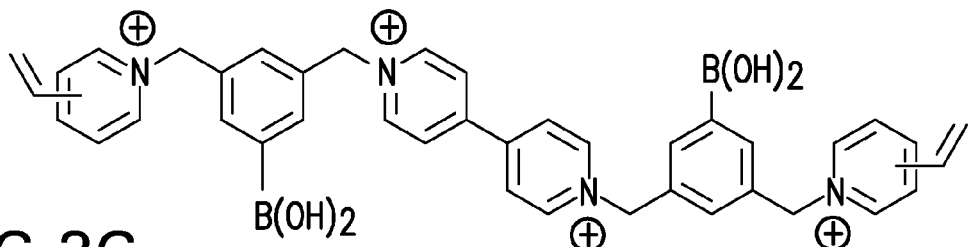
Figure 3H:
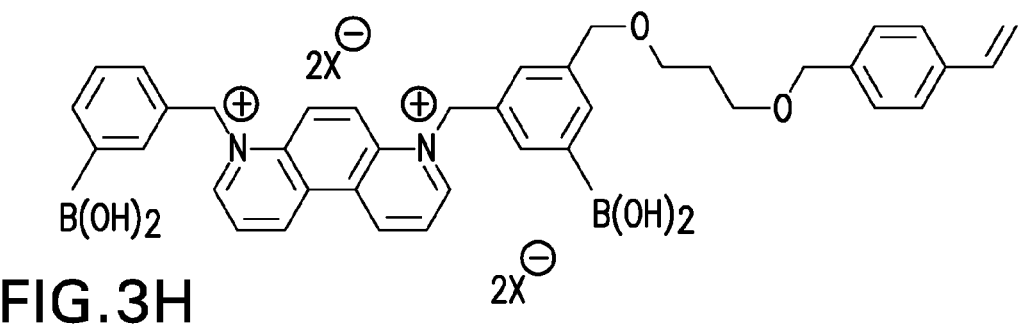
Figure 3I:
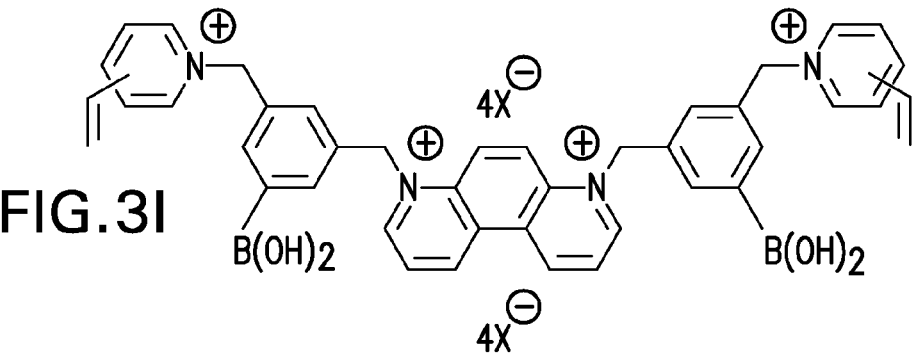

Dyes useful in this invention (See FIGS. 1A, 1B and 1C) are excited by light of wavelength about or greater than 400 nm (preferably 430 nm), with a Stokes shift large enough that the excitation and emission wavelengths are separable, being at least 10 nm, and preferably greater than or equal to about 30 nm. These dyes are susceptible to quenching by electron acceptor molecules, such as viologens, are resistant to photobleaching, and are stable against photo-oxidation, hydrolysis, and biodegradation. Dyes useful in the present invention have an apparent Stem-Volmer quenching constant when tested with methyl viologen of about 50 or greater and preferably greater than 100. A general description of the Stem-Volmer test is found below in Preparation A. Preferred dyes include polymeric derivatives of hydroxypyrene trisulfonic acid and aminopyrene trisulfonic acid. In some cases, the dye is bonded to a polymer through the sulfonamide functional groups. The polymeric dyes are water-soluble, water-insoluble but swellable or dispersible in water or may be crosslinked. A preferred dye as a polymer is for example, a water soluble PEG adduct of 8-hydroxypyrene-1,3,6-N,N', N''-tris(methoxypolyethoxy)ethyl (n~125) sulfonamide) (formed by reaction of acetoxypyrene trisulfonyl chloride with aminoethyl PEG monomethyl ether. The resulting dye polymer has a molecular weight of at least about 10,000 such that, when it is trapped in a hydrogel or network polymer matrix, it is incapable of diffusing out of the matrix into the surrounding aqueous medium.

Representative dyes as discrete compounds are the tris adducts formed by reacting 8-acetoxypyrene-1,3,6-trisulfonylchloride (HPTS-Cl) with an amino acid, such as amino butyric acid. Hydroxypyrene trisulfonamide dyes bonded to a polymer and bearing one or more anionic groups are most preferred, such as copolymers of 8-hydroxypyrene-1-N-(methacrylamidopropylsulfonamido)-N',N''-3,6-bis(carboxypropylsulfonamide) HPTS-$CO_2$-MA with HEMA, PEGMA, etc.

Other examples include soluble copolymers of 8-acetoxypyrene-1,3,6-N,N',N''-tris(methacrylamidopropylsulfonamide) with HEMA, PEGMA, or other hydrophilic comonomers. The phenolic substituent in the dye is protected during polymerization by a blocking group that can be removed by hydrolysis after completion of polymerization. Such blocking groups, which are suitable for example acetoxy, trifluoroacetoxy, and the like are well known in the art. Other preferred dyes include polymeric derivatives of aminopyrene trisulfonic acid [APTS] in which the dye is bonded to the polymer as a pendant group or a unit in the polymer chain. The dye is bonded to the polymer through a sulfonamide linkage or preferably through an amine linking group. Some polymerizable APTS derivatives include:

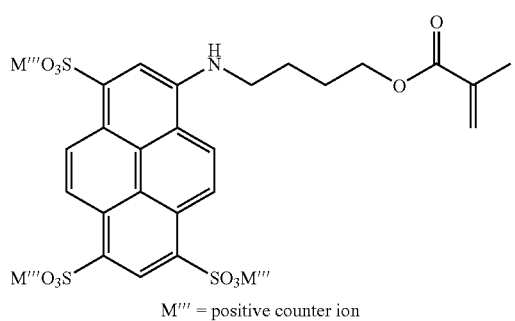
M''' = positive counter ion

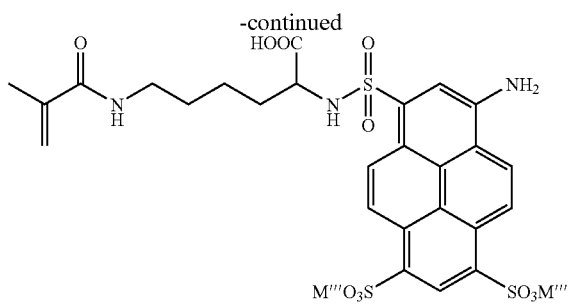

It is essential that, for sensing to occur, the sensing moieties (analyte, dye, quencher) must be in close physical proximity to allow interaction, i.e. mixed on a molecular level and in equilibrium with the species to be detected. While not bound by any theory or mechanism, in most cases the molecules may have to collide or the molecule centers are less than 10 angstroms apart for quenching to occur. However the distance dependent quenching falls of rapidly if the molecules are further apart. It appears that the intensity of the fluorescence emitted by the dye is attenuated by photo-induced intermolecular electron transfer from dye to viologen when viologen/boronic acid adduct and the dye are in close proximity. When glucose binds to the boronic acid, the boronate ester interacts with the viologen thereby altering its quenching efficacy according to the extent of glucose binding. The specific nature of this interaction is not yet established, but it may involve electron transfer from boronate to viologen or boronate formation may shift the reduction potential of the viologen. The reduction potential is an indicator of the ability of a quencher to accept an electron.

Quantum Dot Embodiments

Fluorescent quantum dot semiconductor nanoparticles have found increasing use as replacements for traditional organic fluorophores in such applications as biomolecule tagging, tissue imaging and ion sensing. (Ref. 1-5) Interest in fluorescent quantum dots (QDs) derives from their broad absorption, narrow emission, intense brightness, and good photostability relative to organic dyes. (6) Surprisingly, though, despite the large and diverse set of fluorescence-based sensing systems for glucose, no methods for glucose detection utilizing inherently fluorescent QDs have yet been reported. (7. The two-component approach to glucose sensing described herein allows for considerable flexibility in choosing the quencher/receptor and fluorophore components depending on the particular requirements of the sensing application. For example, fluorophore components are selected to provide any in a range of desired excitation or emission wavelengths while a particular quencher/receptor may be chosen for reasons of its monosaccharide binding selectivity. Some of the advantages of QDs are realized in the two-component system to sense changes in glucose concentration in aqueous solution.

Figure 21:
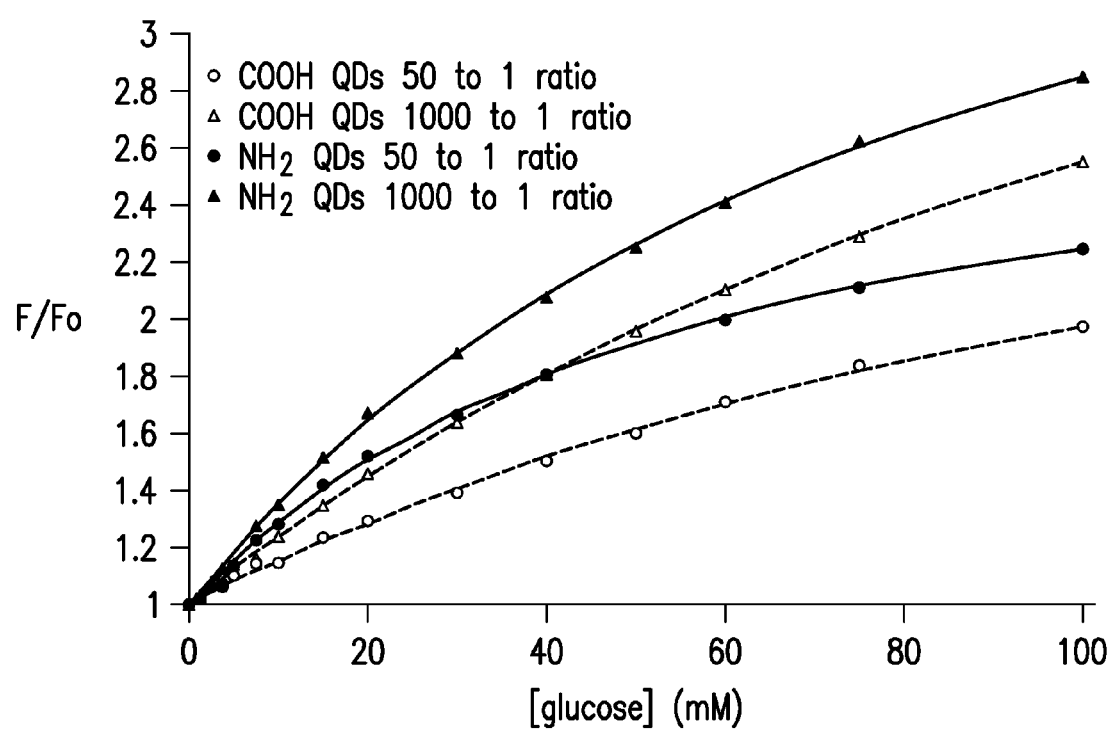
FIG. 21 is a graphic representation of glucose response cures obtained by using o-BBV$^{2+}$ quenching the fluorescence amine and carboxyl substituted quantum dots at pH 7.4.

Fluorescent QDs are constructed of inorganic semiconductor core materials such as CdTe and CdSec, coated with an insulating shell material such as ZnS and further treated to provide desired surface chemistry. For the preparation of water-soluble core shell QDs, surface functionalization with phosphonate, carboxyl, or amine groups is often employed. The particular surface chemistry allows for the QDs to bind to molecules of interest such as proteins and also determines their solubility, aggregation behavior and sensitivity to quenching processes. Several groups have observed quenching of QD fluorescence using methyl viologen ($MV^{2+}$). (1, 13-15) The process is believed to occur through excited state electron transfer from the QD to the viologen resulting in reduction of the viologen to $MV^{\bullet+}$. Previous studies had shown that viologens were extremely efficient in statically quenching the fluorescence of many organic dyes considerable degree of recovery of the initial, unquenched quantum dot fluorescence after addition of 100 nM glucose (FIG. 21).

Results using quantum dots in a hydrogel in two component sensing systems for the detection of sugars are in Example 56.

Polymer Matrix for Sensors

For in vivo applications, the sensor is used in a moving stream of physiological fluid which contains one or more polyhydroxyl organic compounds or is implanted in tissue such as muscle which contains said compounds. Therefore, it is essential that none of the sensing moieties escape from the sensor assembly. Thus, for use in vivo, the sensing components are part of an organic polymer sensing assembly. Soluble dyes and quenchers can be confined by a semi-permeable membrane that allows passage of the analyte but blocks passage of the sensing moieties. This can be realized by using as sensing moieties soluble molecules that are substantially larger than the analyte molecules (molecular weight of at least twice that of the analyte or greater than 1000 preferably greater than 5000); and employing a selective semipermeable membrane such as a dialysis or an ultrafiltration membrane with a specific molecular weight cutoff between the two so that the sensing moieties are quantitatively retained.

Preferably the sensing moieties are immobilized in an insoluble polymer matrix, which is freely permeable to glucose, see FIG. 8. The polymer matrix is comprised of organic, inorganic or combinations of polymers thereof. The matrix may be composed of biocompatible materials. Alternatively, the matrix is coated with a second biocompatible polymer that is permeable to the analytes of interest.

The function of the polymer matrix is to hold together and immobilize the fluorophore and quencher moieties while at the same time allowing contact with the analyte, and binding of the analyte to the boronic acid. To achieve this effect, the matrix must be insoluble in the medium, and in close association with it by establishing a high surface area interface between matrix and analyte solution. For example, an ultra-thin film or microporous support matrix is used. Alternatively, the matrix is swellable in the analyte solution, e.g. a hydrogel matrix is used for aqueous systems. In some instances, the sensing polymers are bonded to a surface such as the surface of a light conduit, or impregnated in a microporous membrane. In all cases, the matrix must not interfere with transport of the analyte to the binding sites so that equilibrium can be established between the two phases. Techniques for preparing ultra-thin films, microporous polymers, microporous sol-gels, and hydrogels are established in the art. All useful matrices are defined as being analyte permeable.

Hydrogel polymers are preferred for this invention. The term, hydrogel, as used herein refers to a polymer that swells substantially, but does not dissolve in water. Such hydrogels may be linear, branched, or network polymers, or polyelectrolyte complexes, with the proviso that they contain no soluble or leachable fractions. Typically, hydrogel networks are prepared by a crosslinking step, which is performed on water-soluble polymers so that they swell but do not dissolve in aqueous media. Alternatively, the hydrogel polymers are prepared by copolymerizing a mixture of hydrophilic and crosslinking monomers to obtain a water swellable network polymer. Such polymers are formed either by addition or condensation polymerization, or by combination process. In these cases, the sensing moieties are incorporated into the polymer by copolymerization using monomeric derivatives in combination with network-forming monomers. Alternatively, reactive moieties are coupled to an already prepared matrix using a post polymerization reaction. Said sensing moieties are units in the polymer chain or pendant groups attached to the chain.

The hydrogels useful in this invention are also monolithic polymers, such as a single network to which both dye and quencher are covalently bonded, or multi-component hydrogels. Multi-component hydrogels include interpenetrating networks, polyelectrolyte complexes, and various other blends of two or more polymers to obtain a water swellable composite, which includes dispersions of a second polymer in a hydrogel matrix and alternating microlayer assemblies.

Monolithic hydrogels are typically formed by free radical copolymerization of a mixture of hydrophilic monomers, including but not limited to HEMA, PEGMA, methacrylic acid, hydroxyethyl acrylate, N-vinyl pyrrolidone, acrylamide, N,N'-dimethyl acrylamide, and the like; ionic monomers include methacryloylaminopropyl trimethylammonium chloride, diallyl dimethyl ammonium. chloride, vinyl benzyl trimethyl ammonium chloride, sodium sulfopropyl methacrylate, and the like; crosslinkers include ethylene dimethacrylate, PEGDMA, trimethylolpropane triacrylate, and the like. The ratios of monomers are chosen to optimize network properties including permeability, swelling index, and gel strength using principles well established in the art. In one embodiment, the dye moiety is derived from an ethylenically unsaturated derivative of a dye molecule, such as 8-acetoxypyrene-1,3,6-N,N',N'''-tris(methacrylamidopropylsulfonamide), the quencher moiety is derived from an ethylenically unsaturated viologen such as 4-N-(benzyl-3-boronic acid)-4'-N'-(benzyl-4ethenyl)-dipyridinium dihalide (m-SBBV) and the matrix is made from HEMA and PEGDMA. The concentration of dye is chosen to optimize emission intensity. The ratio of quencher to dye is adjusted to provide sufficient quenching to produce the desired measurable signal.

Alternatively, a monolithic hydrogel is formed by a condensation polymerization. For example, acetoxy pyrene trisulfonyl chloride is reacted with an excess of PEG diamine to obtain a tris-(amino PEG) adduct dissolved in the unreacted diamine. A solution of excess trimesoyl chloride and an acid acceptor is reacted with 4-N-(benzyl-3-boronic acid)-4'-N'-(2hydroxyethyl) bipyridinium dihalide to obtain an acid chloride functional ester of the viologen. The two reactive mixtures are brought into contact with each other and allowed to react to form the hydrogel, e.g. by casting a thin film of one mixture and dipping it into the other.

Polymers that are capable of reacting with boronic acids to form boronate esters under the conditions of this method are not useful as matrix polymers. Such polymers have 1,2- or 1,3-dihydroxy substituents, including but not limited to cellulosic polymers, polysaccharides, polyvinyl alcohol and its copolymers and the like.

Multi-component hydrogels wherein the dye is incorporated in one component and the quencher in another are preferred for making the sensor of this invention. Further, these systems are optionally molecularly imprinted to enhance interaction between components and to provide selectivity for glucose over other polyhydroxy analytes. Preferably, the multicomponent system is an interpenetrating polymer network (IPN) or a semi-interpenetrating polymer network (semi-IPN).

The IPN polymers are typically made by sequential polymerization. First, a network comprising the quencher is formed. The network is then swollen with a mixture of monomers including the dye monomer and a second polymerization is carried out to obtain the IPN hydrogel.

The semi-IPN hydrogel is formed by dissolving a soluble polymer containing dye moieties in a mixture of monomers including a quencher monomer and through complex formation with the fluorophore. The fluorescence of core shell quantum dots bearing polar surface groups such as carboxyl and amine is similarly quenched through complex formation with the boronic acid-substituted viologen quenchers.

Figure 18:
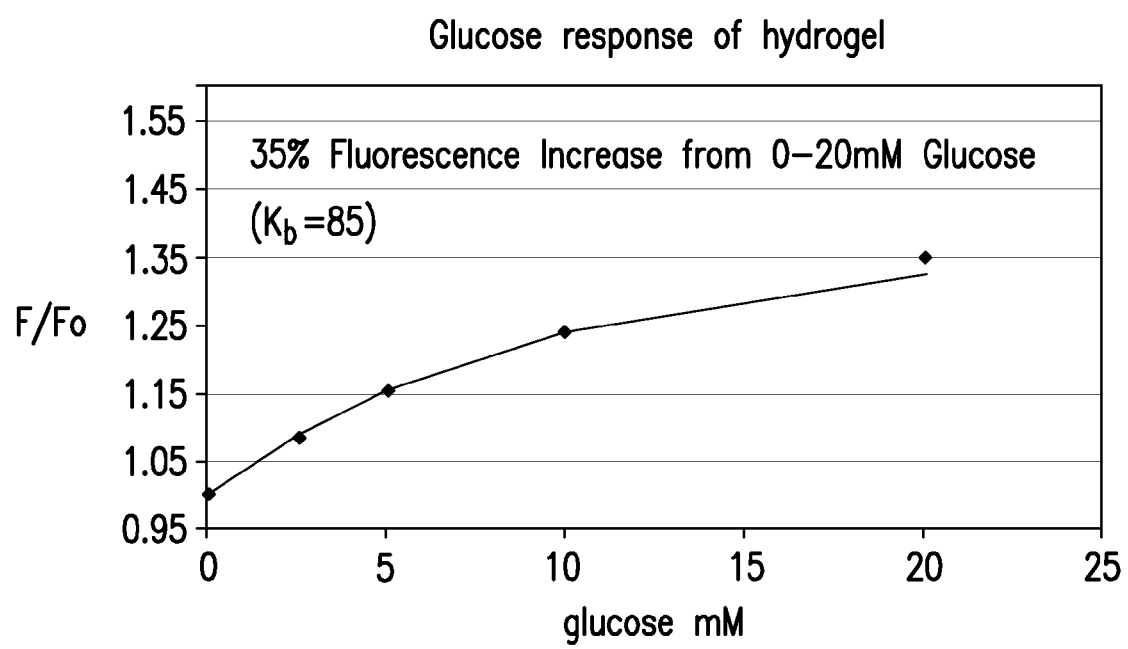
FIG. 18 is a graphic representation of the glucose response of hydrogel.
Figure 19:
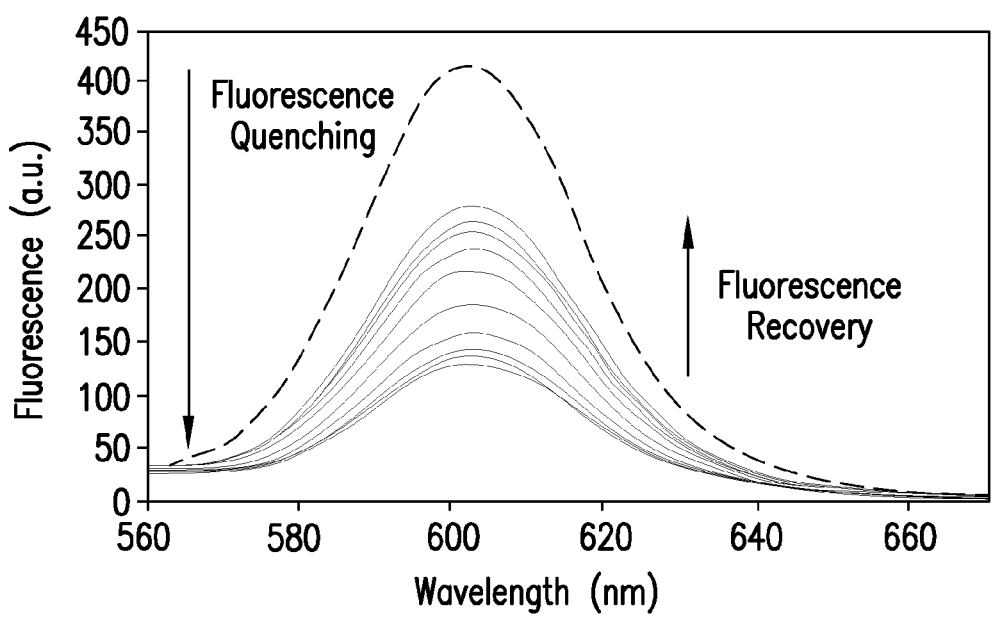
FIG. 19 is a graphic representation of the characteristic fluorescence response in addition of a quantum dot solution followed by addition of glucose to the quencher solution at pH 7.4.

Two sets of commercially available core shell CdSc quantum dots were identically prepared except for their surface fictionalization: one set was prepared with carboxyl groups on the surface, the other with amine groups. (16) Both sets had a fairly narrow fluorescence emission centered at 604 nm. These QDs indeed functioned in this system in a manner similar to that of organic dyes: showing a decrease in fluorescence upon addition of viologen quencher. Robust fluorescence was observed recovery upon addition of glucose to the quenched QD solutions (FIG. 18).

Figure 20:
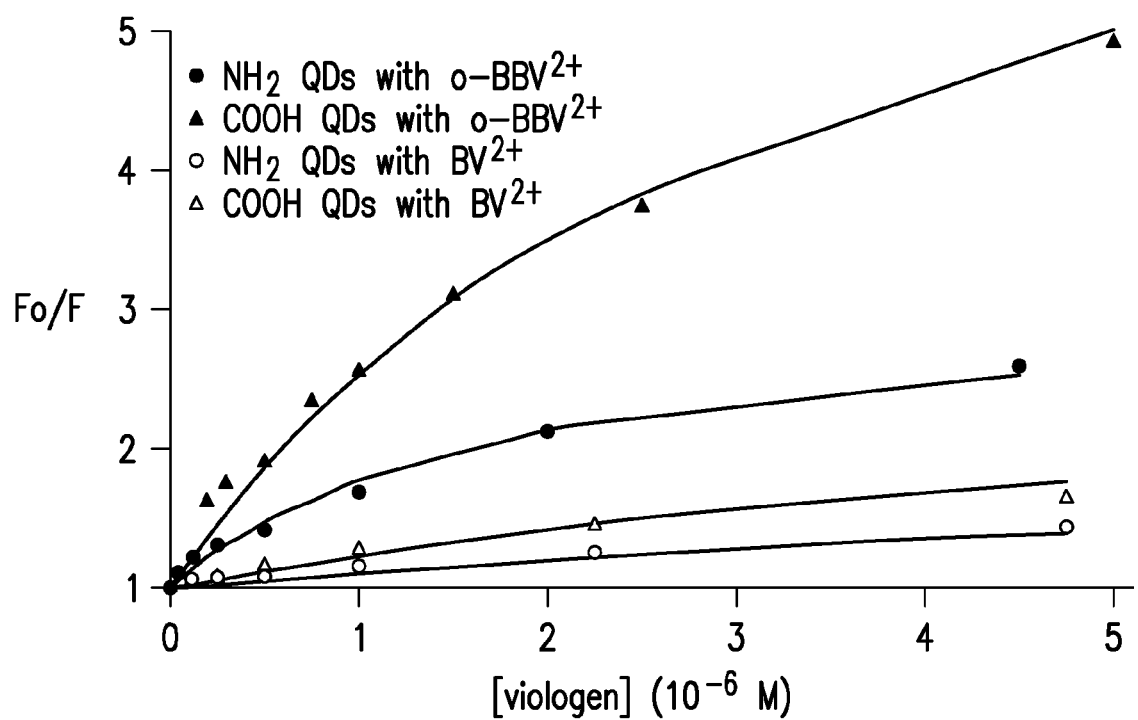
FIG. 20 is a graphic representation of a Stern Volmer Plot of 0-BVV$^{2+}$ and BV$^{2+}$ quenching the fluorescence of amine and carboxyl substituted quantum dots ($2 \times 10^{-7}$) M at pH 7.4.

The sensitivity of both quantum dot sets fluorescence quenching by the boronic acid substituted viologen o-BBV$^{2+}$ was determined in pH 7.4 aqueous solution (FIG. 20). The fluorescence of both the carboxyl and amine substituted QDs were sensitive to quenching by o-BBV$^{2+}$, with the carboxyl substituted quantum dots showing a stronger sensitivity to quenching than the amine substituted dots. Fluorescence of both sets of QDs was also similarly quenched by simple unsubstituted benzyl viologen (BV$^{2+}$) (17) though to a lesser degree than with boronic acid substituted viologen. Significantly, while the degree of ionization of the surface group was not determined, the carboxyl substituted dots are expected to exist primarily in their anionic form at pH 7.4 whereas the amine dots would most likely be neutral. The enhanced sensitivity of the carboxyl substituted QDs may be due to electrostatic attraction between the cationic viologen quencher and the anionic surface groups on the QD.

Previous studies had shown that choice of an appropriate ratio of quencher to fluorophore was critical for a strong and linear signal response across the physiological glucose range. When experimenting with several different quencher-to-quantum dot ratios generally the same behavior was observed as with traditional organic dyes where higher ratios tended to give larger, more linear fluorescence signals in response to addition of glucose (FIG. 3).

Both sets of QDs were screened for glucose response at quencher: QD ratios of 50, 200, 500, and 1000 to 1. For both the amine and carboxyl substituted QDs, we obtained our optimal results using the 1000:1 quencher-to-quantum dot ratio. Significantly, the use of quantum dots allows for a large signal response and a polymerizing. Alternatively, a soluble quencher polymer is dissolved in a monomer mixture containing the dye monomer and the mixture polymerized. In either case, the molecular weight of the soluble component must be sufficiently high (about or greater than 10,000) that it cannot diffuse out of the network, i.e. it becomes physically bound in or trapped by the matrix.

Figure 4A:
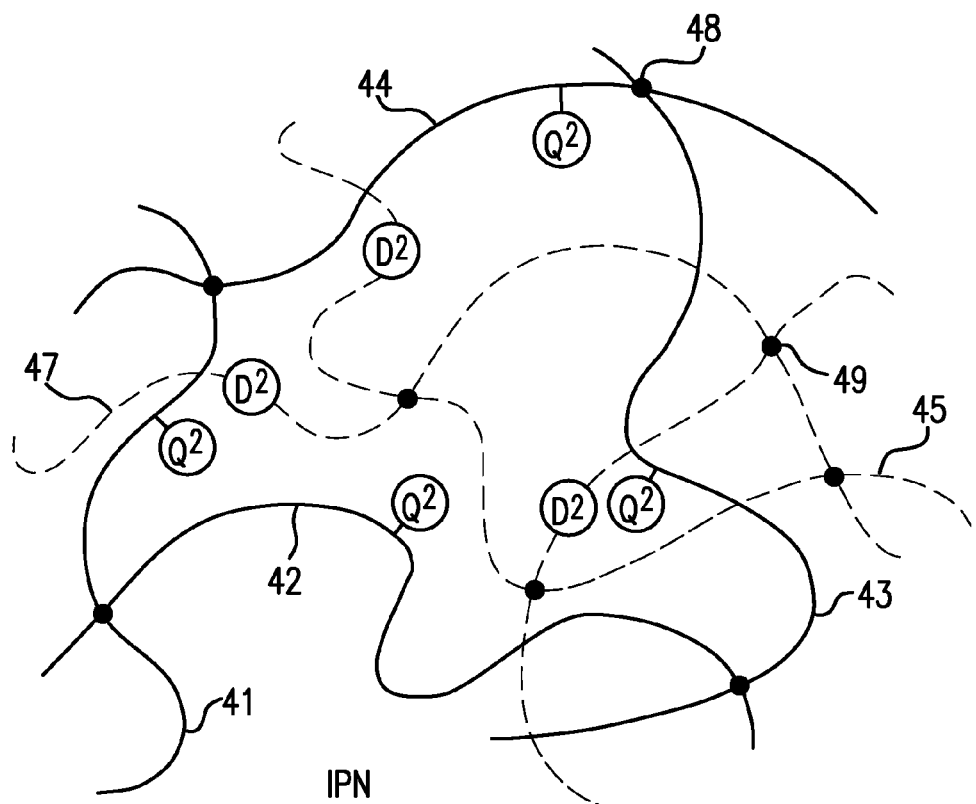
FIGS. 4A and 4B are schematic representations of the structures of the interpenetrating polymer network (IPN) polymers and semi-IPN polymers respectively of the invention.
Figure 4B:
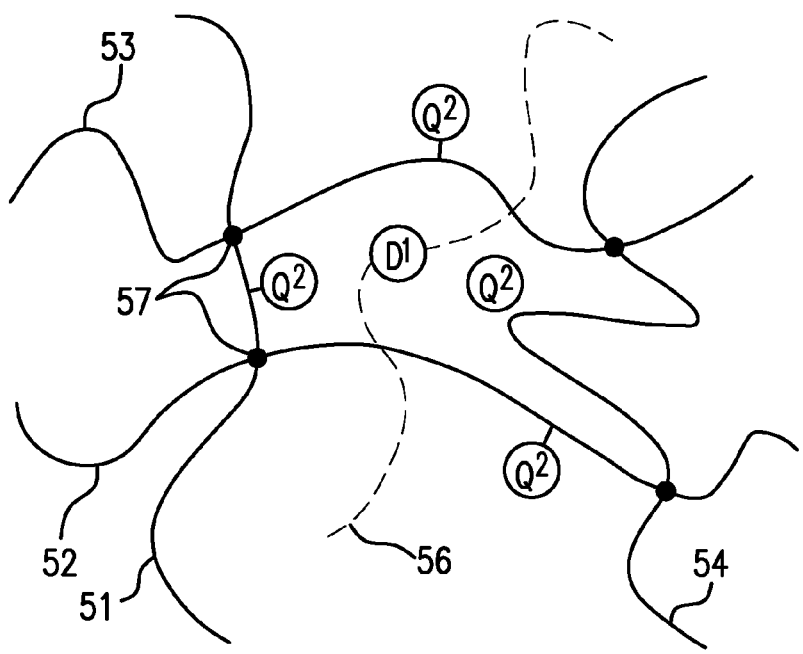

In FIG. 4A, one group of polymer chains 41, 42, 43 and 44 contain the quencher, for example quencher Q$^2$. A second group of polymer chains 45, 46 and 47 containing the dye, for example, dye D$^2$, is formed at about the same time or sequentially. The points of crosslinking of the polymers are designated as 48 and 49. In FIG. 4B, one group of polymer chains 51, 52, 53 and 54 contain the quencher, for example, quencher Q$^2$. Dye D$^1$ is to a pendant group on a second polymer 56. Crosslinking points 57 are designated.

Molecular Imprinting—Optionally, the polymers of this invention are molecularly imprinted. In one embodiment, an organic salt is formed from a monomeric quencher cation and a monomeric dye anion. The organic salt is then copolymerized, under conditions such that the ion pairs remain at least partially associated, to form a monolithic hydrogel matrix. Alternatively, the quencher monomer is polymerized to form a first polymer, which is then ion exchanged to obtain a polyelectrolyte with anionic dye countering. The latter is then copolymerized with suitable monomers to form an interpenetrating dye polymer, which is associated through ionic bonding with the quencher polymer. The combination is either an IPN polymer or a semi-IPN polymer. In another embodiment, the polymers of this invention are molecularly imprinted to enhance selectivity for glucose over other polyhydroxyl compounds, such as fructose, by first forming a bis boronate ester of glucose with a polymerizable viologen boronic acid. This ester is then copolymerized and hydrolyzed to obtain a glucose-imprinted polymer. This polymer is subsequently used to form an IPN with a dye polymer.

In one aspect, m-SBBV is mixed with glucose in about a 2:1 molar ratio in aqueous organic solvent, e.g. water/dioxane. The product bis-boronate ester is recovered by distilling off the solvents under vacuum. The product is next copolymerized with HEMA and PEGDMA to obtain a first hydrogel following the procedures described in Example 14. Glucose is then leached from the hydrogel by conditioning in dilute hydrochloric acid. After conditioning in deionized water, the hydrogel is contacted with the dye monomer of Example 28 to form a complex between the anionic dye and the cationic quencher polymer. A second stage polymerization with more HEMA and PEGDMA is then carried out to form a molecularly imprinted IPN hydrogel.

The individual components in a multi-component hydrogel are made by the same or a different polymerization scheme. For example, in an IPN polymer, a first network is formed by free radical polymerization, the second by condensation polymerization. Likewise, in a semi-IPN polymer, the soluble component is formed by condensation polymerization and the network by free radical polymerization. For example, a quencher polymer, such as poly 4,4'-N,N'-bis(1,3-xylylene-5-boronic acid) bipyridinium dihalide is formed by condensing 4,4'-dipyridyl with 3,5-bis-bromomethyl phenylboronic acid. The quencher polymer is dissolved in a reaction mixture containing 8-acetoxypyrene-1,3,6-N,N',N'''-tris(methacrylamidopropylsulfonamide) as described above, and the solution is polymerized to obtain the semi-IPN hydrogel.

The combination of components described herein produces a device for the determination of polyhydroxy substituted organic molecules in physiological fluids.

In a specific embodiment, a high molecular weight water-soluble dye is prepared by condensing acetoxypyrene trisulfonyl chloride with aminoethyl PEG monomethyl ether to obtain the 8-hydroxypyrene-1,3,6-N,N',N''-tris-(methoxypolyethoxyethyl (n~125) sulfonamide). The PEG dye polymer is dissolved in a mixture comprised of HEMA, PEGDMA, 4-N-(benzyl-3-boronic acid)-4'-N'-(benzyl-4-ethenyl)-dipyridinium dihalide (m-SBBV), aqueous alcohol and free radical initiator and polymerized to obtain a semi-IPN hydrogel. After hydrolysis with dilute base and leaching with deionized water, the hydrogel is affixed to a bifurcated optical fiber light conduit such that it can be exposed to and equilibrate with the body fluid. The light conduit together with appropriate filters is connected to a blue light emitting diode (LED) light source and a silicon photodetector together with an electronic controller and associated measurement instrumentation. The sensor is placed in the tip of a catheter, which is inserted in the body in the desired location. The sensor is excited by light of about 475 nm and the fluorescence intensity monitored at about 520 nm. The level of glucose in the body fluid is determined from the intensity of the emission.

A Single Component Viologen Sensor

In another embodiment the invention is a boronic acid substituted viologen covalently bonded to a fluorophore. An example of a single component viologen sensor as a discrete compound is shown as Example 39. Preferably, the adduct is a polymerizable compound or is a unit in a polymer. One such adduct is prepared by first forming an unsymmetrical viologen from 4,4'-dipyridyl by attaching a benzyl-3-boronic acid group to one nitrogen and an aminoethyl group to the other. The viologen is condensed sequentially first with 8-acetoxypyrene-1,3,6-trisulfonyl chloride in a 1:1 mole ratio followed by reaction with excess PEG diamine to obtain a prepolymer mixture. An acid acceptor is included in both steps to scavenge the byproduct acid. The prepolymer mixture is crosslinked by reaction with a polyisocyanate to obtain a hydrogel. The product is treated with base to remove the blocking group. Incomplete reaction products and unreacted starting materials are leached out of the hydrogel by exhaustive extraction with deionized water before further use. The product is responsive to glucose when used as the sensing component as described herein.

Alternatively, said adducts are ethylenically unsaturated monomers for example dimethyl bis-bromomethyl benzene boronate is reacted with excess 4,4-dipyridyl to form a half viologen adduct. After removing the excess dipyridyl, the adduct is further reacted with an excess of bromoethylamine hydrochloride to form the bis-viologen adduct. This adduct is coupled to a pyranine dye by reaction with 8-acetoxypyrene trisulfonyl chloride in a 1:1 mole ratio in the presence of an acid acceptor followed by reaction with excess aminopropylmethacrylamide. Finally, any residual amino groups are reacted with methacrylol chloride. After purification the dye/viologen monomer is copolymerized with HEMA and PEGDMA to obtain a hydrogel.

The advantage of this group of viologens is that dye and quencher are held in close proximity by covalent bonds, which could lead to increased sensitivity. The disadvantage is that making these adducts is a formidable synthetic challenge and changes in composition are difficult to implement. Characterization and purification of the product is equally difficult. Therefore, the embodiments in which dye and quencher are separate entities are preferred.

Batch Optical Method of Analysis for Glucose

Measurements are carried out in a conventional luminescence spectrometer. A solution containing a dye and quencher of this invention buffered to pH=7.4 is prepared and loaded into a cuvet. The sample is excited by light of wavelength suitable for the dye being used and the fluorescence intensity measured. A fixed amount of the unknown glucose containing solution is added to the solution and the measurement is repeated. The change in intensity is used to calculate glucose concentration by reference to a calibration curve determined separately by measuring a standard series of glucose solutions and plotting the results as intensity change as a function of concentration. In this method, the sensing components need to be stable only for the time of the test, and the reaction with glucose need not be reversible.

Optical Method of Process Stream Analysis

A flow-through cell is fabricated for the luminescence spectrometer. A sensing polymer is mounted in the cell such that it is exposed on one surface to the excitation light and on the other to the process stream. A baseline is established by passing the process stream free of glucose through the cell and measuring the steady state fluorescence. The process stream is then passed through the cell and the fluorescence intensity monitored as a function of time. Glucose concentration is determined by reference to a calibration curve as described above. In this method, the sensor must be stable over time of operation and the reaction with glucose must be reversible. Further, the sensing moieties must be immobilized and not leach out into the process stream.

Device Configuration

FIG. 8 is a schematic representation of the device as used for one time or continuous monitoring for sugar, i.e. glucose. The sensing polymer 81 which contains the dye and quenched may be attached to an optional support 82. For some embodiments an optional semi-permeable polymer membrane 83A is present. For other applications it may be useful to have an optimal biocompatible coating 83B covering the assembly. The light source 84 is connected to an optical filter 85 to an optical fiber 86 to the sensing polymer 81. Detector 87 is connected to an optical filter 88 to an optical fiber 89 which connects to sensing polymer 81. Light source 84 and detector 87 are both connected to electronic controller 90. Thus the system can detect changes in the sensing polymer based on the glucose content of the physiological fluid. The device useful in a process stream and for in vivo implanting and monitoring is shown in FIGS. 9 and 10. FIG. 9 shows the optical device. FIG. 10 is the cross sectional representation of the probe. For FIG. 9, light source 11 (visible) is connected by optical fiber 12 to active cell 13. Semipermeable membrane 14 allows the analyte to enter and exit freely from cell 13. Optical fiber 15 conveys the altered light to filter 16, and optional photomultiplier to 17 to produce the analyte spectrum for analysis.

As shown in FIGS. 9 and 10, cell 13 includes the selectively permeable membrane such that the mixture of polymer 21, dye 22, and quenched 23 are retained in cell 13 under the conditions of analysis. The light enters cell 14 via optical fiber 12. Within the active portion of 14A of cell 14, the polymer 21, dye 22 and quenched 33, contact analyte 24, which has selectively entered the cell causing a quantitative and reproducible change in the spectrum. This modified light signal travels optical fiber 15 to photomultiplier 17 to be analyzed. One skilled in the art will recognize that the serving moieties of this invention can be used in other implantable fluorescence sensing devices known in the art. The components for the quencher, fluorophore and analyte permeable component (aka, matrix) are described herein and in the claims. All are incorporated by reference in this specification.

Experimental

Reagents and solvents are used as received from commercial supplier unless otherwise noted. (See *Chem Sources* USA which is published annually.)

The following examples are provided to be descriptive and exemplary only. They not to be construed to limiting in any manner or fashion.

Procedure A

Fluorescence Spectroscopy Analysis of the Apparent Stern-Volmer Quenching Constant of Methyl Viologen with a Fluorescent Dye The apparent Stern-Volmer quenching constant is derived from the slope of a SternVolmer plot of relative fluorescence intensity ($F_o/F$) versus concentration of quenched (M). See J. R. Lakowicz, (1999) *Principles of Fluorescence Spectroscopy Second Edition*, Kluwer Academic/Plenum Publishers, New York, pp. 237-289. One skilled in the art is in general able to perform this analysis for any fluorescent dye/ quenched pair in a particular solvent of interest. This general Stern-Volmer analysis is used in determining the Stern-Volmer quenching constants in 0.1 ionic strength pH 7.4 phosphate buffer.

In order to avoid concentration quenching effects, the concentration of the dye is generally adjusted so that the optical density of the dye, at excitation $\lambda_{max} \leq 0.5$ absorption units. Once the desired dye concentration is determined, a stock dye solution is prepared in which the concentration is 5 times greater than that desired in the final measurements. For example, a dye for which the desired final concentration, which gives an optical density of excitation $\lambda_{max} \leq 0.5$ absorption units, is $1 \times 10^{-5}$ M, would require a stock solution in which the concentration is $5 \times 10^{-5}$ M.

Once determined, as is described above, 10 mL of dye stock solution of the appropriate concentration is made by weighing out the appropriate mass of dye and placing the solid into a 10 mL volumetric flask. The flask is then filled to the 10 mL mark with 0.1 ionic strength pH 7.4 phosphate buffer.

A stock solution of methyl viologen (25 mL, 0.0025 M) was prepared in a 10-mL volumetric flask with pH 7.4 phosphate buffer (0.1 ionic strength). Seven different solutions containing methyl viologen were then prepared in pH 7.4 phosphate buffer as described below in

TABLE 1

| Volume dye standard (mL) | Volume quencher standard (mL) | Volume buffer (mL) | Final (dye) (M) | Final (Quenched) (M) |
|---|---|---|---|---|
| 1 | 0.00 | 4.00 | 1.00E−05 | 0.00E+00 |
| 1 | 0.20 | 3.80 | 1.00E−05 | 1.00E−04 |
| 1 | 0.30 | 3.70 | 1.00E−05 | 1.50E−04 |
| 1 | 0.40 | 3.50 | 1.00E−05 | 2.50E−04 |
| 1 | 0.50 | 3.00 | 1.00E−05 | 5.00E−04 |
| 1 | 1.50 | 2.50 | 1.00E−05 | 7.50E−04 |
| 1 | 2.00 | 2.00 | 1.00E−05 | 1.00E−03 |

Each sample is then in-turn analyzed in a luminescence spectrometer set at the appropriate excitation wavelength and the appropriate emission wavelength range for the corresponding dye. The instrumental settings (slit widths, scan speed, optical filters, excitation wavelength, emission wavelength range) are held constant throughout the analysis of the series of samples). The emission fluorescence intensity is then determined as the integration of the fluorescence intensity over the emission wavelength range by the trapezoidal rule approximation method. The integrated values are plotted on the y-axis and the quenched concentrations are plotted on the x-axis and the slope of the resulting line is calculated by linear regression as the Stern-Volmer quenching constant. One skilled in the art will realize that based on quenching mechanism the Stern-Volmer plot may not result in a linear relationship. However through the use of the appropriate mathematical relationships, which is known and understood by one skilled in the art, the apparent Stern-Volmer quenching constant is calculated and used for comparison.

Preparation A

Synthesis of Dimethyl-(4-Bromomethyl)-Benzeneboronate

An oven-dried, 100-mL round bottom flask was cooled under argon, fitted with a magnetic stirring bar, and charged with (4-bromomethyl)-benzeneboronic acid (12.49 mmols, 2.684 g). The flask was sealed with a septum and charged with pentane (55 mL). The suspension was stirred at room temperature and upon addition of freshly distilled $CH_3OH$ (3.16 g, 4 mL, 97 mmols) the solution instantly clarified. After stirring for 20 minutes, the solution was dried over $MgSO_4$, then over $CaCl_2$ (to remove excess $CH_3OH$). The supernatant was cannulated, under argon, through a glass-fritted funnel (medium), and the pentane subsequently removed in vacuo. The remaining yellow oil was further dried under reduced pressure (0.1 torr, 1 hr). Yield: 1.6 g, 6.59 mmols (56%). $^1$H-NMR ($CD_3OD$, ppm): 4.5 (s, 2H), 7.4 (d, 2H), 7.55 (d, 2H). $^{11}$B-NMR ($CH_3OH$, ppm): 29 (s). Similar procedures were used to prepare the corresponding 2- and 3-isomers. The products were used to make the boronic acid-viologen compounds of Examples 1-3, 5 and 6.

Preparation B

Synthesis of 8-Acetoxy-Pyrene-1,3,6-Trisulfonyl Chloride

Trisodium-8-acetoxy-pyrene-1,3,6-trisulfonate (acetoxy-HPTS, 11.33 g, 20 mmol) was suspended in 30 mL of thionyl chloride to which 5 drops of dimethylformamide was added. The suspension was refluxed for 3 hr., during which time it became a brown solution. The solution was then cooled to 25° C. under an argon atmosphere. Thionyl chloride was then distilled off under vacuum (2 Torr) leaving a yellow residue. The yellow residue was transferred to three separate centrifuge tubes along with 60 mL of dichloromethane. The suspensions were then centrifuged and the supernatant solutions transferred to a dry round bottom flask. The residue remaining in the centrifuge tubes was washed an additional four times each with 10 mL portions of dichloromethane. The supernatant solutions were combined and left overnight under an argon atmosphere and some precipitation was observed. The dichloromethane solution was added to 250 mL of pentane causing precipitation of a large amount of yellow solid. The supernatant was removed by a double-ended needle and the yellow solid was dried on high vacuum (0.2 Torr). Yield: 8.62 g, 15.5 mmol (78%), $^1$H-NMR (500 MHz, $CDCl_3$, ppm): 2.682 (s, 3H), 8.833, (d, J=10 Hz, 1H), 8.915 (s, 1H), 9.458 (d, J=10 Hz, 1H), 9.509 (d, J=10 Hz, 1H), 9.630 (s, 1H), 9.685 (d, J=10 Hz, 1H). This product was used in Examples 7, 9, 13, 14 and 15.

Preparation C

Synthesis of 4-(4-Pyridyl)-N-(Benzyl-4-Ethenyl)-Pyridinium Chloride

An oven-dried, 100-mL round bottom flask was cooled under argon, fitted with a magnetic stirring bar, and charged with 4,4'-dipyridyl (12.50 g, 80 mmols). The flask was sealed with a septum and charged with $CH_3OH$ (20 mL). The homogenous solution was stirred at room temperature while 4-(chloromethyl)styrene (2.82 mL, 20 mmols) was added dropwise via syringe. After stirring the solution at room temp for 48 hours, the solvent was removed in vacuo. Dry tetrahydrofuran (50 mL) was added to the reaction flask via cannula and the mixture stiffed for three days, at which point the stirring was stopped, the solids allowed to settle, and the solvent was removed as much as possible via cannula. This process was repeated two more times, in each case reducing the mixing time to 24 hours. After the third trituration the mixture was filtered under nitrogen and washed with dry diethyl ether (200 mL) via cannula. The cake was dried by passing dry nitrogen through it under pressure for 1 hour, and finally by applying vacuum (0.1 Torr, 1 h). Yield: 5.56 g, 18 mmols (90%), $^1$HNMR ($D_2O$, ppm); 9.12 (d, 2H), 8.86, (d, 2H), 8.48 (d, 2H), 7.98 (d, 2H), 7.67 (d, 2H), 7.57 (d, 2H), 6.87 (dd, 1H), 5.92 (s, 2H), 5.45 (d, 1H). This compound was used in Examples 5 and 6.

Preparation D

Synthesis of N-Benzyl-4-Ethenyl-4,7-Phenanthrolinium Chloride (4,7-Phen SV)

A flame dried, side armed 100-mL round bottom flask, equipped with a magnetic stirring bar, was cooled under argon and charged with 4,7-phenanthroline (2.14 g, 11.86 mmols). The flask was equipped with a reflux condenser attached to an argon (g) line and charged with 4-(chloromethyl)styrene (0.905 g, 0.836 mL, 5.93 mmols) and anhydrous $CH_3CN$ (20 mL) through the side arm. The solution was heated to reflux under argon (g) for 17 h, then cooled to room temperature and precipitated with diethyl ether (30 mL). The suspension was allowed to settle and the supernatant removed via cannula. The remaining residue along with 15 mL of solvent was cannulated into a centrifuge tube, triturated with acetone (20 mL), and centrifuged (process repeated 4 times). The brownish/pink solid was triturated with diethyl ether (3×20 mL) and dried under reduced pressure. Yield: 0.376 g, 1.13 mmols (19%). $^1$H NMR (250 MHz, $CD_3OD$, ppm): 5.266 (d, 1H, 11 Hz), 5.80 (d, 1H, J=17.75 Hz), 6.482 (s, 2H), 6.708 (dd, 1H, $J_1$=1 Hz, $J_2$=17.75 Hz), 7.374 (d, 1H, J=8 Hz), 7.496 (d, 1H, J=8 Hz) 8.00, (dd, 1H, $J_1$=4 Hz, $J_2$=8.5 Hz), 8.453 (dd, 1H, $J_1$=6 Hz, $J_2$=8.5 Hz), 8.60 (d, 1H, J=10 Hz), 8.697 (d, 1H, J=10 Hz), 9.20 (d, 1H, J=4 Hz), 9.50 (d, 1H, J=8.25 Hz), 9.65 (d, 1H, J=5.75 Hz), 10.188 (d, 1H, J=8.5 Hz). $^{13}$C NMR (62.5 MHz, $CD_3OD$); 62.40, 121.344, 124.899, 126.023, 128.454, 129.031, 130.778, 132.161, 133.893, 134.242, 137.205, 139.848, 140.410, 140.699, 144.041, 147.976, 149.541, 154.661.

This compound was used in Examples 25.

EXAMPLE 1

Synthesis of 4,4'-N,N'-Bis-(Benzyl-3-Boronic Acid) Dipyridinium Dibromide

An oven-dried, 50-mL centrifuge tube was cooled under argon, fitted with a magnetic stirring bar, and charged with 4,4'-bipyridyl (0.469 g, 3 mmols). The tube was sealed with a septum and charged with $CH_3OH$ (7 mL). The homogenous solution was stirred at room temperature while freshly prepared dimethyl-(3-bromomethyl)-benzeneboronate (1.82 g, 7.5 mmols) was added via syringe. After stirring the solution for 15 hours, the reaction vessel was centrifuged (4 min at 3200 RPM) and the $CH_3OH$ cannulated to a separate flask. The remaining yellow solid was triturated with acetone:water (24:1, V/V, 25 mL), stirred vigorously on a vortex mixer and centrifuged. The acetone solution was removed by cannula and the trituration process repeated two more times. The solid was then triturated with diethyl ether using the same process. The pale yellow solid, in the centrifuge tube, was then dried on the high vacuum (0.6 torr, 2 hr). Yield: 0.956 g, 1.63 mmols (54%). MP: decomposition >230° C. $^1$H-NMR ($D_2O$, ppm): 6.093 (s, 4H), 7.715, (dd, 2H, $J_1$=7.5 Hz, $J_2$=7.5 Hz), 7.788 (d, 1H, J=7.5 Hz), 7.984 (s, 1H), 8.002 (d, 1H, J=7.5 Hz), 8.662 (d, 4H, J=7 Hz), 9.293 (d, 4H, J=7 Hz). $^{11}$B-NMR ($CH_3OH$, ppm): 29 (s).

This compound was used in Examples 16-18 and FIG. 6 below.

EXAMPLE 2

Synthesis of 4,4'-N,N'-Bis-(Benzyl-4-Boronic Acid) Dipyridinium Dibromide

Figure 6:
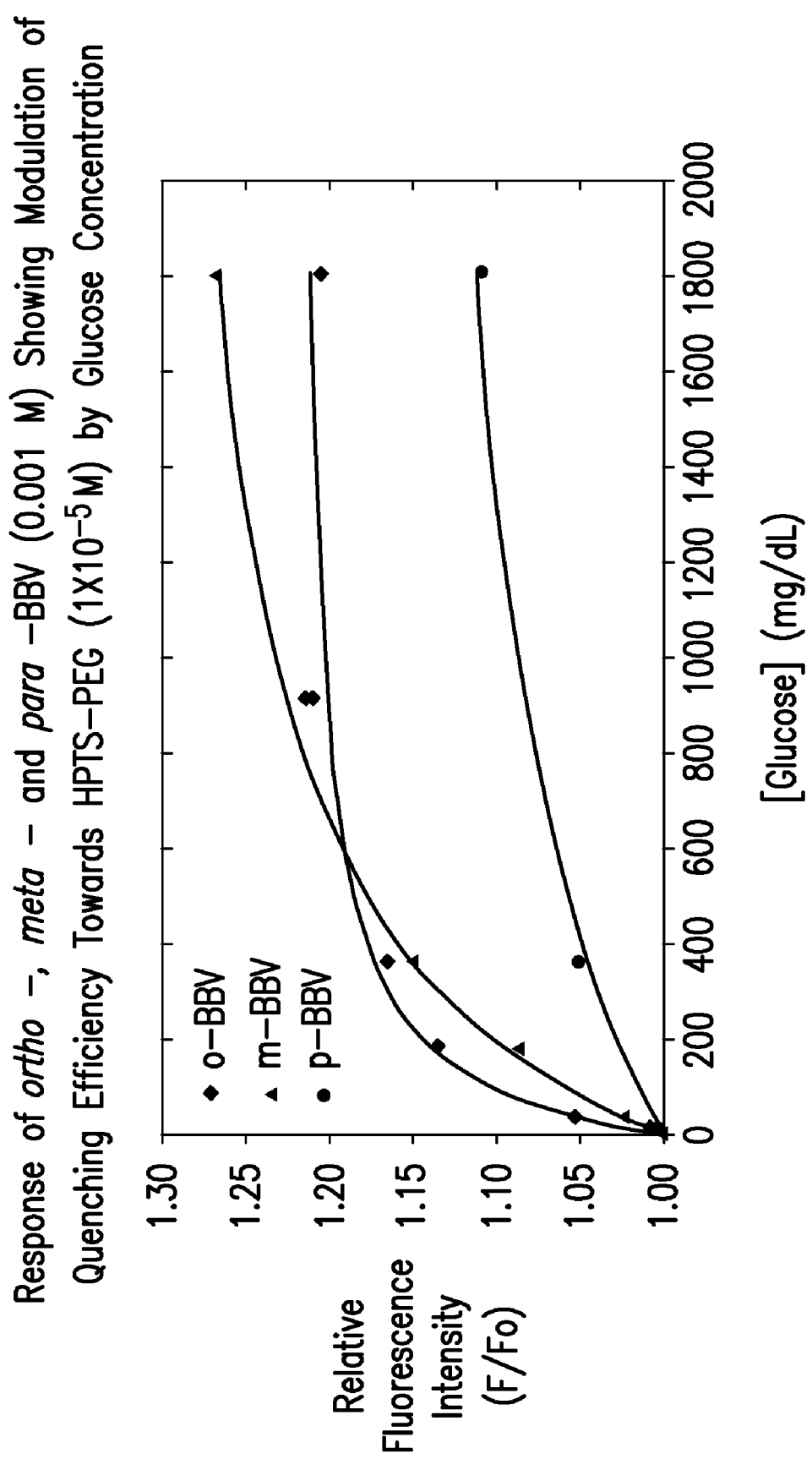
FIG. 6 is a graphic representation of the response of ortho-, meta-, and parabenzyl boronic acid viologen (BBV) (0.001M) showing modulation of quenching efficiencies to HPTS-PEG ($1 \times 10^{-5}$-M) as a function of glucose concentration.

An oven-dried, 50-mL centrifuge tube was cooled under argon, fitted with a magnetic stirring bar, and charged with 4,4'-dipyridyl (0.234 g, 1.5 mmols). The tube was sealed with a septum and charged with anhydrous $CH_3OH$ (7 mL). The homogenous solution was stirred at room temperature while freshly prepared dimethyl-(4-bromomethyl)-benzeneboronate (1.09 g, 4.5 mmols) was added via syringe. After stirring the solution for 15 hours, the reaction vessel was centrifuged (4 min at 3200 RPM) and the $CH_3OH$ cannulated to a separate flask. The remaining yellow solid was triturated with acetone:water (24:1, V/V, 25 mL), stirred vigorously on a vortex mixer, and centrifuged. The acetone solution was removed by cannula and the trituration process repeated two more times. The solid was then triturated with diethyl ether using the same process. The pale yellow solid, in the centrifuge tube, was then dried under reduced pressure (0.6 torr, 2 hr). Yield: 0.723 g, 1.63 mmols (82%). MP: decomposition greater than 230° C. $^1$H-NMR ($D_2O$ ppm): 6.116 (s, 4H), 7.670 (d, 4H, J=8.25 Hz), 8.017 (d, 4H, J=8.25 Hz), 8.698 (d, 4H, J=6.5 Hz), 9.325 (d, 4H, J=6.5 Hz). $^{11}$B-NMR ($CH_3OH$, ppm): 29 (s). See Examples 17 and 18 and FIG. 6.

EXAMPLE 3

Synthesis of 4,4'-N,N'-Bis-(Benzyl-2-Boronic Acid) Dipyridinium Dibromide (a) An oven-dried, 50-mL centrifuge tube was cooled under argon and fitted with a magnetic stirring bar. 4,4'-Bipyridyl (1.5 mmol, 0.234 g) was weighed out into the tube which was then sealed with a septum and charged with $CH_3OH$ (7 mL). The homogenous solution was stirred at room temperature while mixing. Freshly prepared dimethyl-(2-bromomethyl)benzeneboronate (4.5 mmols, 1.2 mL, 1.09 g) was added via syringe to the reaction tube and the resulting brown/orange solution was stirred at room temperature (ambient) for 15 hrs. The reaction vessel was then centrifuged (4 min at 3200 RPM) and the $CH_3OH$ cannulated to a separate flask. The remaining yellow solid was triturated with diethyl ether (25 mL), stirred vigorously using a vortex mixer, and centrifuged. The ether solution was removed by cannula and the trituration process repeated three more times. The pale yellow solid, in the centrifuge tube, was then dried under reduced pressure (0.6 torr, 2 hr). The yield was 70%. $^1$HNMR ($D_2O$, ppm): 6.21 (s, 2H), 7.72, (m, 3H), 7.91 (d, 1H), 8.60 (d, 2H), 9.18 (d, 2H). $^{11}$BNMR ($CH_3OH$, ppm) 30.2 (broad s).

This compound was found to quench the fluorescence of the dye of Example 8 and to respond to glucose. See Example 17.

EXAMPLE 4

Synthesis of 1,7-N,N'-Bis(Benzyl-3-Boronic Acid)-Phenanthrolinium Dibromide

An oven-dried, 50-mL centrifuge tube was cooled under argon, fitted with a magnetic stirring bar, and charged with 1,7-phenanthroline (0.288 g, 1.6 mmols). The tube was then sealed with a septum, charged with $CH_3OH$ (4 mL), and freshly prepared dimethyl-(3bromomethyl)-benzeneboronate (0.972 g, 4 mmols) was added via syringe. The homogenous solution was stirred at room temperature for 15 hrs, and then refluxed for 2 hrs. The reaction mixture was cooled to room temperature under argon and the $CH_3OH$ was removed in vacuo. The yellow/orange solid was triturated overnight with acetone:water (40 mL, 24:1, V/V), then with diethyl ether (2×40 mL). The suspension was filtered through a glass-fritted funnel (medium), and the solid isolated under argon. Yield: 0.495 g, 0.812 mmols (51%). MP: >230° C. $^1$H-NMR ($D_2O$, ppm): 6.504 (1H), 7.638 (1H), 8.025 (m, 2H), 8.2505 (d, 1H, 8.5 Hz), 8.483 (m, 6H) 8.738 (d, 1H, J=8.5 Hz), 9.315 (d, 1H, J=5.75 Hz), 9.605 (d, 1H, J=5.75 Hz), 10.098 (d, 1H, J=8.5 Hz) 10.269 (d, 111, J=8.5 Hz). $^{11}$B-NMR ($CH_3OH$, ppm): 28 (s).

This compound was found to quench the fluorescence of the dye of Example 8 and respond to glucose.

EXAMPLE 5

Synthesis of 4-N-(Benzyl-4-Boronic Acid)-4'-N'-(Benzyl-4-Ethenyl)Dipyridinium Bromide Chloride (P-SBBV)

An oven-dried, 50-mL centrifuge tube was cooled under argon, fitted with a magnetic stirring bar, and charged with 4-(4-pyridyl)-N-(benzyl-4-ethenyl)-pyridinium chloride (0.463 g, 1.5 mmols). The tube was sealed with a septum and charged with acetonitrile (6 mL). The resulting pink/orange suspension was stirred at room temperature while freshly prepared dimethyl-(4-bromomethyl)-benzeneboronate (0.486 g, 2 mmols) was added via syringe. After stirring the suspension for 23 hrs the reaction vessel was centrifuged (4 min at 3200 RPM) and the acetonitrile cannulated to a separate flask. The remaining yellow solid was triturated with acetone:water (25 mL, 24:1, V/V), stirred vigorously on a vortex mixer, and centrifuged. The acetone solution was removed by cannula and the trituration process repeated two more times. The solid was then triturated with diethyl ether using the same process. The bright yellow solid, in the centrifuge tube, was then dried under reduced pressure (0.5 torr, 1 hr). Yield: 0.43 1 g, 0.824 mmols (55%). MP: >200° C. $^1$H-NMR ($D_2O$ ppm): 5.405 (d, 1H, J=11.5 Hz), 5.929 (d, 2H, J=17.5 Hz), 5.934 (s, 2H), 5.981 (s, 2H), 6.832 (dd, 2H, J,=17.5 Hz, J2=1 I Hz), 7.523 (d, 2H, J=9 Hz), 7.562 (d, 2H, J=8 Hz), 7.626 (d, 2H, J=8 Hz), 7.8815 (d, 2H, J=8.5 Hz), 8.566 (dd, 4H, J,=3.6 Hz, J2=1.5 Hz), 9.1855 (dd, 4H, J,=6.5 Hz, J2=6 Hz). $^{11}$B-NMR ($CH_3OH$, ppm): 28 (s).

This compound was used to quench the fluorescence of the dye of Example 8 and to respond to glucose.

EXAMPLE 6

Synthesis of 4-N-(Benzyl-3-Boronic Acid)-4'-N'-(Benzyl-4-Ethenyl)-Dipyridinium Bromide Chloride (M-SBBV)

An oven-dried, 50-mL centrifuge tube was cooled under argon, fitted with a magnetic stirring bar, and charged with 4-(4-pyridyl)-N-(benzyl-4-ethenyl)-pyridinium chloride (0.463 g, 1.5 mmols). The tube was sealed with a septum and charged with acetonitrile (6 mL). The resulting pink/orange suspension was stirred at room temperature while freshly prepared dimethyl-(3-bromomethyl)-benzeneboronate (0.486 g, 2 mmols) was added via syringe. After stirring the suspension for 23 hours the reaction vessel was centrifuged (4 min at 3200 RPM) and the acetonitrile cannulated to a separate flask. The remaining yellow solid was triturated with acetone:water (25 mL, 24:1, V/V), stirred vigorously on a vortex mixer, and allowed to sit overnight. The acetone solution was removed by cannula and the solid then triturated with diethyl ether (3×25 mL); each time the triturant was removed via cannula. The remaining bright yellow solid, in the centrifuge tube, was then dried under reduced pressure (0.015 torr, 3 hr). Yield: 0.584 g, 1.12 mmols (74%). MP: decomposition greater than 150° C. $^1$H-NMR (D$_2$O ppm): 5.5165 (d, 1H, J=10.75 Hz), 6.0435 ppm (d, 1H, J=17.8 Hz), 6.095 (s, 2H), 6.049 (s, 2H), 6.9433 (dd, 1H, J$_1$=11.5 Hz, J$_2$=17.9 Hz), 7.626 (m, 4H), 7.724 (m, 2H), 7.979 (s, 1H), 7.994 (d, 1H, J=7.5 Hz), 8.648 (d, 4H), 9.280 (d, 4H). $^{11}$B-NMR (CH$_3$OH, ppm): 28 (s).

This compound was used to make the polymers of Examples 10, 11, 12, and 14.

EXAMPLE 7

Synthesis of 8-Acetoxypyrene-1,3,6-N,N',N"-Tris-(Methoxypolyethoxyethyl (N~125) Sulfonamide)

A 250-mL round bottom flask was equipped with a magnetic stirring bar and charged with 170 mL of dry tetrahydrofuran (THF). Methoxy-polyethyleneglycol (PEG)-amine (5.65 g, 5630 g/mol, 1 mmol) was added to the flask along with 0.5 grams of granular CaH$_2$. The mixture was heated to 30° C. for 24 hr with stirring. Diisopropylethylamine (0.6 mL, 129.24 MW, 0.742 g/mL, 3.4 mmol) was added to the flask and the mixture allowed to stir for an additional hour. The flask was cooled to room temperature and filtered through an air sensitive glass fritted filtration apparatus to remove excess CaH$_2$ and Ca(OH)$_2$. The THF solution was placed back into a 250 mL round bottom flask with magnetic stir bar and heated to 30° C. with stirring. 8-acetoxypyrene-1,3,6-trisulfonyl chloride (0.185 g, 624.8 g/mol, 0.3 mmol) was added to the warm THF solution. The solution immediately turned a deep blue color and faded to a red wine color over 15 min. The reaction was stirred at 30° C. for 24 hr. The solvent was removed by rotary evaporation and the residue was dissolved in 100 mL of 1 M HCl. The aqueous solution was extracted with methylene chloride (3×100 mL). The methylene chloride fractions were combined and the solvent was removed by reduced pressure evaporation to yield compound as a red solid. Yield: about 5.5 g (97%). FTIR (KBr pellet, cm$^{-1}$): 842, 963, 1060, 1114, 1150, 1242, 1280, 1343, 1360, 1468, 1732, 2525, 2665, 2891. 1. This product was then used in Examples 8 and 11, 16 and 17.

EXAMPLE 8

8-Hydroxypyrene-1,3,6-N,N',N"-Tris-(Methoxypolyethoxyethyl (N~125) Sulfonamide)

8-Acetoxypyrene-1,3,6-N,N',N-tris-(methoxypolyethoxyethyl (n~125) sulfonamide) (5.5 g, 0.32 mmols) was dissolved in 100 mL of 1 M NaOH and stirred for 2 hr. The aqueous solution was neutralized to pH 7 and extracted with methylene chloride (3×100 mL). The methylene chloride fractions were combined and reduced to approximately 10 mL by rotary evaporation. The concentrated methylene chloride solution was then added dropwise into 400 mL of vigorously stirred diethyl ether in an Erlenmeyer flask. The diethyl ether was filtered using a Buchner funnel. The product was isolated as an orange powder. Yield: 5.425 g, 0.31 mmol (94%). FTIR (KBr pellet, cm$^{-1}$): 842, 963, 1060, 1110, 1150, 1242, 1281, 1343, 1360, 1468, 2888. This compound was identified as the trisubstituted sulfonamide derivative by Fourier Transform Infrared (FTIR). The sulfonic acid IR stretch occurs at 1195.7 cm$^{-1}$. There is no 1195.7 cm$^{-1}$ stretch in the FTIR of this compound. Instead a stretch of 1110 cm$^{-1}$, assigned to the sulfonamide, is observed. When dissolved in pH 7.4 buffer, the fluorescence of this compound is quenched by methyl viologen with an apparent Stern-Volmer quenching constant of 319M$^{-1}$.

This was quenched by the products of Examples 1, 2 and 3 and used in Examples 11, 16, 17, 18 and 19.

EXAMPLE 9

8-Acetoxypyrene-1,3,6-N,N',N"-Tris(Methacrylamidopropylsulfonamide) (Acetoxy-HPTS-MA)

A 100-mL round bottom flask was charged with aminopropyl-3-methacrylamide-HCl salt (2.68 g, 15 mmol) and 50-mL of acetonitrile to give a white suspension. Water was added dropwise while stirring until all of the white suspension had disappeared producing two layers. Potassium carbonate was added and the suspension was stirred for 15 minutes. The supernatant was transferred to a 500-mL round bottom flask and the potassium carbonate was washed with 50-mL acetonitrile, which was then combined in the 500-mL round bottom flask. A yellow solution of acetoxy-HPTS-Cl (1.03 g, 1.8 mmol), 200-mL acetonitrile, and 20-mL dichloromethane was added under argon to the 500-mL round bottom flask containing the free amine in acetonitrile causing the solution to turn dark red with precipitate formation. The solution was stirred for 1 hr and the supernatant was transferred and concentrated under vacuum to give a dark residue. The residue was extracted with water (1000 mL) and a 50:50 acetonitrile/ethyl acetate solution (700 mL). The organic extract was washed with an additional 1000 mL water. The organic extract was dried over magnesium sulfate and concentrated on a rotary evaporator to give a red residue, which was dissolved in methanol. The methanol solution was concentrated and the resulting red residue was dried under high vacuum to give a red solid, which was the unprotected HPTS-MA. Yield: 420 mg, 0.5 mmol, 28%. $^1$H-NMR (500 MHz, D$^4$-methanol, ppm): 1.617 (p, J=6.5 Hz, 8H), 1.781 (s, 3H), 1.767 (s, 6H), 2.934 (p, J=6.5 Hz, 9H), 3.158 (mult. 8H), 5.211 (t, J=1.5 Hz), 5.229 (t, J=1.5 Hz), 5.488 (s, 1H), 5.510 (s, 2H), 8.290 (s, 1H), 8.837 (d, J=9.5 Hz, 1H), 8.913 (d, J=9.5 Hz, 1H), 8.988 (d, J=1.5 Hz 1H), 9.201 (d, J=9.5 Hz, 1l1), 9.222 (s, 1H). Unprotected HPTS-MA (100 mg, 0.1 mmol) was then suspended in 10 ml, acetic anhydride and a catalytic amount of sodium acetate was added and the suspension refluxed for 2 hr. Acetic anhydride and acetic acid were removed under vacuum and the resulting brown residue was extracted with 20 mL acetonitrile. The extract was dripped into 150 mL, diethyl ether causing the precipitation of a brown solid. Yield: 75 mg, 0.09 mmol (86%).

This monomer was used in Examples 13, 14 and 15.

EXAMPLE 10

Copolymerization of 4-N-(Benzyl-3-Boronic Acid)-4'-N'-(Benzyl-4 Ethenyl)-Dipyridinium Bromide Chloride into a Water-Soluble Polymer A 50-mL cone-shaped round bottom flask was charged with 2-hydroxyethyl methacrylate (1.50 g, 11.5 mmols), 4-N-(benzyl-3-boronic acid)-4'-N'-(benzyl-4-ethenyl)dipyridinium bromide chloride (0.1 g, 0.191 mmols), and 3-((methacryloylamino)propyl)) trimethyl ammonium chloride (0.50 g, 2.27 mmols). After the flask was sealed with a septum, the solution was vigorously stirred on a vortex mixer. The vessel was then charged with isopropyl alcohol:water (8 mL, 1:1, V/V) and deoxygenated with argon for one hr. Concurrently, in a separate 100-mL, side-armed round bottom flask, a solution of 2,2'azobisisobutyronitrile (AIBN, 100 mg, 0.609 mmols) in isopropyl alcohol:water (5 mL) was prepared. The flask was equipped with a magnetic stir bar and a condenser, and deoxygenated with argon for one hour. The entire manometric solution was taken-up by syringe and 1 mL was added, through the sidearm, to the AIBN solution. The AIBN reaction vessel was then placed in a 70° C. oil bath and the remaining manometric mixture added via syringe pump over 6 hrs (1.5 mL/hr). The resulting orange solution was cooled to room temperature under argon and the solvent carefully removed in vacuo. The amorphous solid was dissolved in $CH_3OH$ (20 mL) and quantitatively transferred to a centrifuge tube via cannula. After addition of diethyl ether (20 mL) and formation of a white precipitate, the product was isolated via centrifugation (4 min at 3200 RPM). It was washed with diethyl ether (30 mL), dried under reduced pressure (0.5 torr 3 hrs), and isolated under an inert atmosphere of argon. Yield: 1.345 g, (67 Wt %). The amount of viologen moiety incorporated into the polymer was determined, by UV absorbance, to be greater than 99% of the expected value.

This product was used in Example 19.

EXAMPLE 11

Semi-IPN: The Thin Film Copolymerization of 4-N-(Benzyl-3-Boronic Acid)-4'-N-(Benzyl-4-Ethenyl)-Dipyridinium Bromide Chloride Using HPTS-PEG A 10-mL volumetric flask was charged with 2-hydroxyethyl methacrylate (3.525 g, 27.08 mmols), 4-N-(benzyl-3-boronic acid)-4'-N'-(benzyl-4-ethenyl)-dipyridinium bromide chloride (0.039 g, 0.075 mmols), 3-((methacryloylamino)propyl) trimethyl ammonium chloride (0.3 g, 1.36 mmols), polyethylene glycol dimethacrylate (1.11 g, 1.11 mmols), 2,2'-azobis (2-(2-imidazolin-2-yl)propane)dihydrochloride (0.025 g, 0.077 mmols), and 8-hydroxypyrene-1,3,6-N,N',N''-tris-(methoxypolyethoxyethyl (n~125) sulfonamide) (0.013 g, $7.5 \times 10^{-4}$ mmols); it was filled to the 10-mL mark with isopropyl alcohol:water (1:1, V/V). After the solution was vigorously stirred on the vortex mixer it was transferred, via pipette, to a 50-mL, cone-shaped round bottom flask and deoxygenated with argon for one hour. The monomer solution was taken-up by syringe and the syringe attached to the polymerization chamber. The solution was then inserted into the cell, under argon, to fill the entire cavity of the cell. The chamber was sealed with Teflon plugs and wrapped in two ZIPLOC® freezer bags. The entire unit was submerged in a 40° C. waterbath and heated for 17 hrs. The polymerization chamber was removed from the bath and the bags, and subsequently disassembled to afford a thin green polymeric film. The polymeric film was leached and stored under pH 7.4 phosphate-buffer. This product was used in Example 12.

*The polymerization chamber was comprised of (1) An IR cell-holder: two stainless steel plates fashioned to contain the cell and the LUER LOC® ports; (2) A Cell: two glass plates containing a TEFLON® 0.02" spacer in between, with holes drilled through the top plate and spacer; and (3) A Gasket: a precision-cut rubber spacer used to the seal the cell to the cell-holder.

EXAMPLE 12

Fluorescence Spectroscopy Analysis of Semi-IPN Copolymer of 4-N-(Benzyl-3-Boronic Acid)-4'-N'-(Benzyl-4-Ethenyl)-Dipyridinium Bromide Chloride (M-SBBV) Using HPTS-PEG A 10-mm path length, 5-mL glass cuvet, which was open on both sides was equipped with two disposable polyethylene cuvet caps. Holes were drilled through the caps such that the threads of a 10/32 standard thread, 1/8" I.D. hose end adapter were screwed into place. A thin sheet of plastic was then cut into a 35×9 mm rectangle and a window 6×15 mm was cut out of the center. Two fittings were constructed from small septa to put pressure on the plastic mask to hold the polymer in place within the cuvet. The height of the septa was 9 mm. The flow-through-cell was then assembled such that the polymer film was in the center of the cuvet and the plastic mask directly over it, effectively framing the film with its window. The pressure fittings were then put in place using tweezers, one at the bottom of the cell and one at the top. The outside walls of the cuvet caps, which sits inside the cuvet, were coated with vacuum grease and inserted into the cuvet to seal the cell. The cell was placed into a Perkin-Elmer LS50B spectrophotometer equipped with a front surface adapter. The cell was oriented so that its side, touching the polymer, was facing the excitation beam of the instrument (face-first in the front surface adapter). 1/8" TYGON® PTFE tubing was connected to the hose adapters of the flow-through-cell. The orientation of the front surface adapter was optimized so that the emission detector was sensing only the surface of the polymer. A peristaltic pump was used to circulate pH 7.4 phosphate buffer (ionic strength 0.1) through the cell at a rate of 30 mL per minute. The time drive function of the Perkin-Elmer LS50B software was used to acquire fluorescence intensity readings every ten sec for an integration time of two sec. The excitation frequency was set at 475 nm and the emission slit width at 536 nm. The excitation and emission slit widths were set at 2.5 nm. A base line value of 358 (fluorescence intensity) was established with buffer solution. The peristaltic pump was stopped and the pumping solution was changed to 1800 mg/dl glucose in pH 7.4 phosphate buffer.

The fluorescence intensity increased 127 units to a value of 485, corresponding to a 35% signal increase (S/N ratio=72). After switching back to buffer the signal approached the expected baseline value of 358.

EXAMPLE 13

8-Hydroxypyrene-1,3,6-N,N',N''-Tris(Methacrylamidopropylsulfonamide) Hydrogel Polymer A 16-mm NMR tube modified with a female 14/20 ground glass joint was charged with a mixture of isopropyl alcohol/water (1:1, 1.5 mL), HEMA (750 mg), polyethylene glycoldimethacrylate (PEGDMA, n~25) (200 mg), 3-(methacrylamido) propyltrimethyl ammonium chloride (TMAC) (50 mg), 8-acetoxypyrene-1,3,6-N,N',N''-tris(methacrylamidopropylsulfonamide) (acetoxy-HPTS-MA) (1 mg, $1.2 \times 10^{-6}$ mols), and (2,2'-azobis-2(2-imidazolin-2-yl) propane) hydrochloride (VA-044 free radical initiator) (5 mg). All solids were dissolved with the aid of a vortex mixer. The NMR tube was then fitted with a male 14/20 ground glass joint TEFLON® stop cock to vacuum adapter. The mixture was then de-oxygenated via 4 freeze/pump/thaw cycles (−78° C., 1 torr, 5 min. and thawed under nitrogen. The NMR tube was then heated in a water bath at 40° C. (0.5° C. for 12 hr. The glass NMR tube was carefully broken to free the polymer plug. The polymer was dialyzed in 200 mL of de-ionized water with triethylamine (5 drops) (de-ionized water and amine solution was changed every 24 hr for 7 days) to remove the acetoxy protecting group on the acetoxy-HPTS-MA. The resulting polymer plug was cut into about 5-mm slices and analyzed by fluorescence spectroscopy.

Excitation and emission spectra of the gels are substantially identical to spectra obtained for the PEG adduct (Example 12). Samples of the polymer gel suspended in pH 7.4 buffer are visibly fluorescent when examined in daylight. The fluorescence is noticeably diminished when m-SBBV, o-SBBV, or p-SBBV was added to the aqueous phase. The fluorescence was recovered when glucose is added to the solution. Similar gels were prepared with dye concentrations of 0.05 to 5 mg/g polymer (dry weight). All were yellow-green to orange in color and were visibly fluorescent when examined in day (natural) light.

The fluorescence was quenched when the hydrogels were exposed to aqueous o-, m-, and p-BBV (benzyl boronic acid viologens).

EXAMPLE 14

IPN: Copolymerization of 4-N-(Benzyl-3-Boronic Acid)-4'-N'-(Benzyl-4-Ethenyl)-Dipyridinium Bromide Chloride (M-SBBV) Using HPTS-MA Polymer Manometric quenched solution: A 10-mL volumetric flask was charged with 2-hydroxy ethyl methacrylate (27.08 mmols, 3.525 g), 4-N-(benzyl-3-boronic acid)-4'-N'(benzyl-4-ethenyl)-dipyridinium bromide chloride (0.197 mmols, 0.103 g), 3((methacryloylamino)propyl) trimethyl ammonium chloride (1.36 mmols, 0.30 g), polyethylene glycol dimethacrylate (1.11 mmols, 1.11 g), and 2,2'-azobis (2-(2-imidazolin-2-yl)propane)dihydrochloride (0.077 mmols, 0.025 g); it was filled to the 10-mL mark with isopropyl alcohol:water (1:1, V/V). The solution was vigorously stirred on the vortex mixer until homogenous.

Polymeric Dye Powder: A 10-mL volumetric flask was charged with 2-hydroxy ethyl methacrylate (27.08 mmols, 3.525 g), 3-((methacryloylamino)propyl) trimethyl ammonium chloride (1.36 mmols, 0.3 g), polyethylene glycol dimethacrylate (1.11 mmols, 1.11 g), 2,2'-azobis (2-(2-imidazolin-2-yl)propane)dihydrochloride (0.077 mmols, 0.025 g), and 8-Acetoxypyrene-1,3,6-N,N',N"-tris(methacrylamidopropylsulfonamide) ($7.5 \times 10^{-4}$ mmols, $6.6 \times 10^{-4}$ g); it was filled to the 10-mL mark with isopropyl alcohol:water (1:1, V/V). After the solution was vigorously stirred on the vortex mixer it was transferred, via pipette, to a 50-mL round-bottom flask and the flask was sealed with a rubber septum. It was deoxygenated with argon for 30 minutes. The manometric solution was taken-up by syringe and the needle was capped with a rubber stopper. It was then transferred to an argon-filled glove box along with the polymerization chamber. The syringe was attached to the polymerization chamber and the solution was inserted into the cell, under argon, to fill the entire cavity. The chamber was sealed with TEFLON® plugs and wrapped in a ZIPLOC® freezer bag. The entire unit was transferred to an oven and heated to 40° C. for 14 hrs. The polymerization chamber was removed from the oven and the bags, and subsequently disassembled to afford a thin green polymeric film. The film was leached with 500 mL of distilled water (pH 5) for six hours; fresh water was replaced every two hours. The thin film was then dried under reduced pressure (40° C., 20 in Hg, 3 hours), brought to −196° C. and crushed into a fine powder using a mortar and pestle.

Interpenetrating network copolymer: A 50-mL round-bottom flask was charged with manometric quenched-solution (5.2 mL) and polymeric dye-powder (0.169 g). The mixture was vigorously stirred on the vortex mixer for 10 minutes to allow the liquid to be imbibed by the dye particles and then deoxygenated with argon for 15 minutes. The heterogeneous solution was taken-up by syringe and the needle was capped with a rubber stopper. It was then transferred to an argon-filled glove box along with the polymerization chamber* (*See Example 11). The syringe was attached to the polymerization chamber and the solution was inserted into the cell, under argon, to fill the entire cavity. The chamber was sealed with TEFLON® plugs and wrapped in a ZIPLOC® freezer bag. The entire unit was transferred to an oven and heated to 40° C. for 14 hrs. The polymerization chamber was removed from the oven and the bag, and subsequently disassembled to afford a thin, orange, gel-integrated polymeric film. The film was placed in a pH 8-NaOH solution for 12 hours, then leached and stored in pH 7.4 phosphate-buffer.

This product was used in Example 20.

EXAMPLE 15

Two Component System: The Thin Film Copolymerization of 4-N (Benzyl-3-Boronic Acid)-4'-N-(Benzyl-4-Ethenyl)-Dipyridinium Bromide Chloride (M-SBBV) Using HPTS-MA A 10-mL volumetric flask was charged with 2-hydroxyethyl methacrylate (3.525 g, 27.08 mmols), 4-N-(benzyl-3-boronic acid)-4'-N'-(benzyl-4-ethenyl)-dipyridinium bromide chloride (0.039 g, 0.075 mmols), 3-((methacryloylamino)propyl) trimethyl ammonium chloride (0.3 g, 1.36 mmols), polyethylene glycol dimethacrylate (1.11 g, 1.11 mmols), 2,2'azobis (2-(2-imidazolin-2-yl)propane)dihydrochloride (0.025 g, 0.077 mmols) and 8-acetoxy-pyrene-1,3,6-N,N',N"-tris(methacrylamidopropylsulfonamide) ($6.6 \times 10^{-4}$ g, $7.5 \times 10^{-4}$ nmols) it was filled to the 10-mL mark with isopropyl alcohol:water (1:1, V/V). After the solution was vigorously stirred on a vortex mixer it was transferred, via pipette, to a 50-mL, cone-shaped round bottom flask and the flask was sealed with a rubber septum; it was deoxygenated with argon for 30 minutes. The manometric solution was taken-up by syringe and the needle was capped with a rubber stopper. It was then transferred to an argon-filled glove box along with the polymerization chamber* (*See Example 11). The syringe was attached to the polymerization chamber and the solution was inserted into the cell, under argon, to fill the entire cavity. The chamber was sealed with TEFLON® plugs and wrapped in two ZIPLOC® freezer bags. The entire unit was submerged in a 40° C. water-bath and heated for 12 hrs. The polymerization chamber was removed from the bath and the bags, and subsequently disassembled to afford a thin green polymeric film. The polymeric film was placed in a pH 8 NaOH solution for 12 hours, then leached and stored in pH 7.4 phosphate buffer. This product was used in Example 21.

EXAMPLE 16

Fluorescence Spectroscopy Analysis of 4,4'-N,N'-Bis (Benzyl-2,3, or 4-Boronic Acid)-Bipyridinium Dibromide with 8-Hydroxypyrene-1,3,6-N,N',N"-Tris-(Methoxypolyethoxyethyl (N~125) Sulfonamide) HPTS-PEG A stock solution of HPTS-PEG (10 mL, $5 \times 10^{-5}$ M) was prepared in a 10-mL volumetric flask with pH 7.4 phosphate buffer (0.1 ionic strength). Similarly, a m-BBV solution (25 mL, 0.0025 M) was prepared. Seven different solutions containing HPTS-PEG and m-BBV were then prepared in pH 7.4 phosphate buffer as described below in Table 2.

TABLE 2

| Volume HPTS-PEG standard (M) | Volume standard (mL) | Volume buffer (mL) | Final HPTS-PEG (M) | Final BBV (m-BBV)(M) (mg/DL) |
|---|---|---|---|---|
| 1 | 0.00 | 4.00 | 1.00E−05 | 0.00E+00 |
| 1 | 0.20 | 3.80 | 1.00E−05 | 1.005-04 |
| 1 | 0.30 | 3.70 | 1.00E−05 | 1.505-04 |
| 1 | 0.50 | 3.50 | 1.00E−05 | 2.505-04 |
| 1 | 1.00 | 3.00 | 1.00E−05 | 5.005-04 |
| 1 | 1.50 | 2.50 | 1.00E−05 | 7.505-04 |
| 1 | 2.00 | 2.00 | 1.00E−05 | 1.005-03 |

Figure 7:
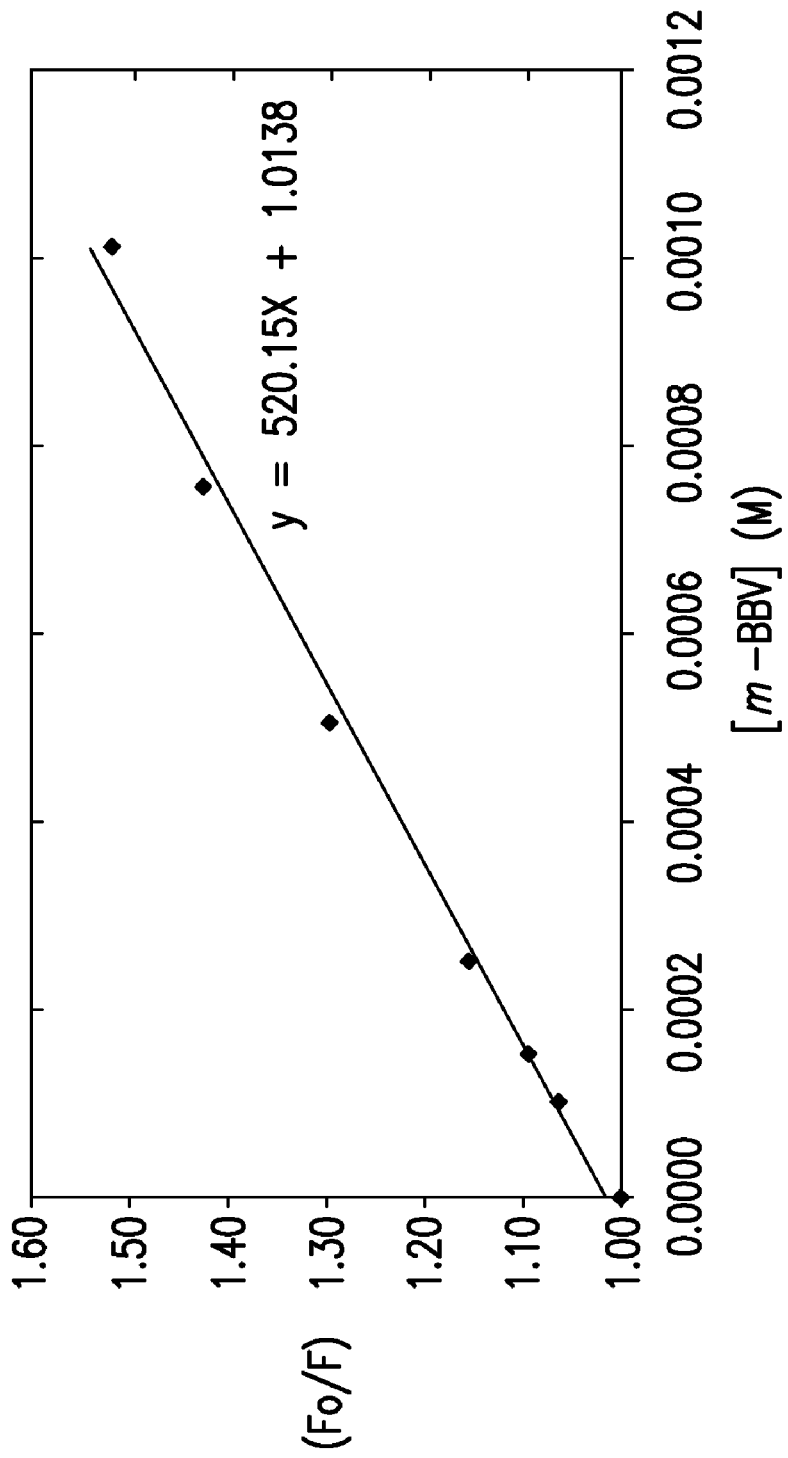
FIG. 7 is a Stem-Volmer plot of m-BBV quenching of HPTS-PEG in pH 7.4 phosphate buffer.

Each sample was then analyzed on the Perkin-Elmer LS50-B luminescence spectrometer. The instrumental settings were:
Excitation Wavelength—473 nm
Emission Wavelength Range—480-630 nm
Excitation Slit Width—0 nm (Instrumental dependent minimum)
Emission Slit Width—0 nm (Instrumental dependent minimum)
Optical filter—none
Scan Speed—100 nm/sec The instrumental settings (slit widths, scan speed, optical filters, excitation wavelength, emission wavelength range) were held constant throughout the series analysis. The emission fluorescence intensity was then quantified by integration (the trapezoidal rule approximation method) of the fluorescence intensity curve between 480 and 630 nm. The apparent Stern-Volmer quenching constant was determined to be 520 $M^{-1}$ (see FIG. 7).

EXAMPLE 17

Glucose Sensing Ability of 4,4'-N,N'-Bis(Benzyl-2,3 or 4-Boronic Acid)-Bipyridinium Dibromide with 8-Hydroxypyrene-1,3,6-N,N',N"-Tris-Methoxypoly-ethoxyethyl (N~125) Sulfonamide) (HPTS-PEG) Analyzed by Fluorescence Spectroscopy (a) A stock solution of HPTS-PEG (10 mL, $5 \times 10^{-5}$ M) was prepared in a 10-mL volumetric flask with pH 7.4 phosphate buffer (0.1 ionic strength). Similarly, a m-BBV solution (25 mL, 0.0025 M) and -D-Glucose (10 mL, 0.250 M) solution were prepared. Seven different solutions containing HPTS-PEG, M-BBV, and -D-Glucose were then prepared in pH 7.4 phosphate buffer as described below in Table 3:

TABLE 3

| Volume HPTS-PEG Stock (mL) | Volume m-BBV stock (mL) | Volume Glucose Stock (mL) | Volume buffer (mL) | Final (HPTS-PEG) (M) | Final (m-BBV) (M) | Final (Glucose) (mg/dL) |
|---|---|---|---|---|---|---|
| 1 | 2 | 0.00 | 2.00 | 1.00E−05 | 1.00E−03 | 0.00 |
| 1 | 2 | 0.02 | 1.98 | 1.00E−05 | 1.00E−03 | 18.02 |
| 1 | 2 | 0.04 | 1.96 | 1.00E−05 | 1.00E−03 | 36.03 |
| 1 | 2 | 0.20 | 1.80 | 1.00E−05 | 1.00E−03 | 180.16 |
| 1 | 2 | 0.40 | 1.60 | 1.00E−05 | 1.00E−03 | 360.32 |
| 1 | 2 | 1.00 | 1.00 | 1.00E−05 | 1.00E−03 | 900.80 |
| 1 | 2 | 2.00 | 0.00 | 1.00E−05 | 1.00E−03 | 1801.60 |

The pH of each sample was independently determined using a pH meter to assure that the pH was constant throughout the series to within 0.02 pH units.

Each sample was then analyzed on the Perkin-Elmer LS50-B luminescence spectrometer. The instrumental settings were the same as Example 16.

The relative integrated values, were then used to construct a calibration curve: plotting $F/F_0$ vs. glucose concentration (mg/dL), where $F_0$ is the integrated fluorescence intensity of the first sample in Table 3 containing 0 mg/dL glucose.

Figure 5:
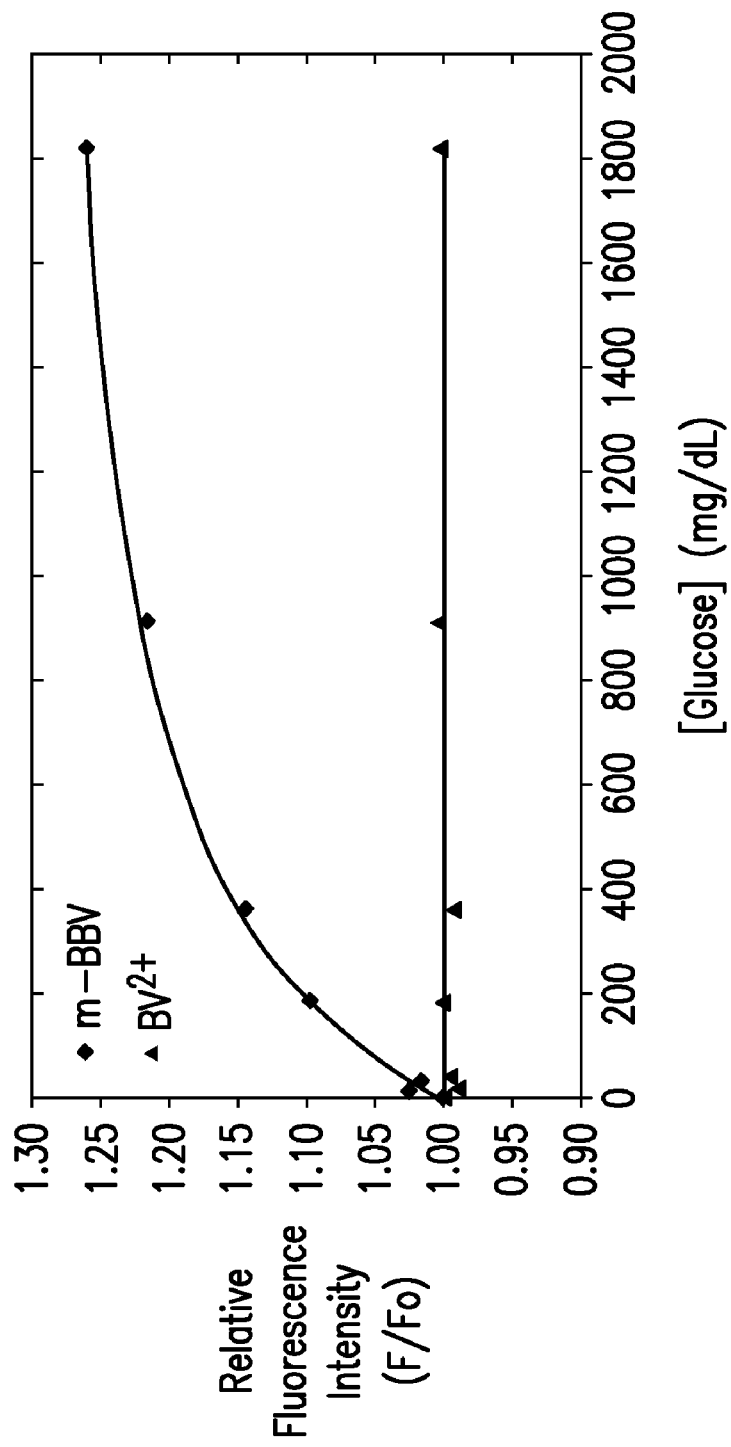
FIG. 5 is a graphic representation of the response of benzyl viologen (0.001M) and 4,4'-N,N'-bis-(benzyl-3-boronic acid)-dipyridinium dibromide (m-BBV) showing modulation of m-BBV quenching efficiency toward HPTS-PEG ($1 \times 10^{-5}$ M) as a function of glucose concentration.

(a) Evaluation of glucose sensitivity with HPTS-PEG. The glucose sensing ability of benzyl viologen was compared to that of 4,4'-N,N'-bis(benzyl-3-boronic acid)-bipyridinium dibromide in the presence of HPTS-PEG dye. The apparent Stern-Volmer quenching constant for benzyl viologen with HPTS-PEG was determined as described in Procedure A, and found to be 559$M^{-1}$. The glucose sensitivity of benzyl viologen in the presence of HPTS-PEG was determined in the same manner. The signal from the benzyl viologen/HPTS-PEG solution did not respond to changes in glucose concentration. The glucose sensitivity of 4,4'-N,N'-bis(benzyl-3-boronic acid)-bipyridinium dibromide is shown in FIG. 5 together with the glucose sensitivity of benzyl viologen.

(b) Similarly, (a) is repeated except that the 4,4'-N,N'-Bis(benzyl-3-boronic acid)bipyridinium dibromide is replaced with 4,4'-N,N'-bis-(benzyl-4-boronic acid) dipyridyl dibromide. The ortho and para isomers were analyzed in the same way. The results for glucose sensitivity are comparable. The results are plotted in FIG. 6.

EXAMPLE 18

Comparison of Glucose Sensitivity of Benzyl Viologen vs. 4,4'N,N'-Bis(Benzyl-3-Boronic Acid)-Bipyridinium Dibromide with HPTS-PEG The glucose sensing ability of benzyl viologen was compared to that of 4,4'-N,N'-bis(benzyl-3-boronic acid)-bipyridinium dibromide in the presence of HPTS-PEG dye. The apparent Stern-Volmer quenching constant for benzyl viologen with HPTS-PEG was determined as described in Procedure A, and found to be 559 $M^{-1}$. The glucose sensitivity of benzyl viologen in the presence of HPTS-PEG was determined as in example 17. The signal from the benzyl viologen/HPTS-PEG solution did not respond to changes in glucose concentration. The glucose sensitivity of 4,4'-N,N'-bis(benzyl-3-boronic acid)-bipyridinium dibromide, as found in Example 17, is shown in FIG. 5 together with the glucose sensitivity of benzyl viologen.

EXAMPLE 19

Fluorescence Spectroscopy Analysis of Water Soluble Copolymer of 4-N-(Benzyl-3-Boronic Acid)-4'-N'-(Benzyl-4 Ethynyl)-Dipyridinium Bromide Chloride (M-SBBV)

m-SBBV (50 mL, 2.5 mM) copolymer from Example 10 was prepared in pH 7.4 phosphate buffer and pH balanced (0.02 pH units) with NaOH solution. Six different solutions of poly m-SBBV (the analyte, 0, 0.10, 0.15, 0.25, 0.50, 0.75, 1.0 mM) containing HPTS-PEG (dye, $1 \times 10^{-5}$ M) were then prepared and analyzed on the spectrofluorimeter. The analyte/dye solutions were contained in a standard 10-mm path length, quartz cuvet, and the spectrofluorimeter was set to an excitation and emission frequency of 473 and 533, respectively. The excitation and emission slit widths were set to 0 nm. After the fluorescence spectra were obtained for the solutions mentioned above, additional spectra of the analyte/dye solutions were obtained in the presence and absence of glucose and fructose. The apparent differences in spectra were quantified as areas under the curve. The difference in areas was then determined to be representative of the polymer response to glucose or fructose, e.g., in the absence of glucose or fructose the representative area under the curve was determined to be 26479.45. Upon addition of different concentrations of glucose, the areas changed accordingly as indicated in Table 4.

TABLE 4

Change in Fluorescence Intensity of 1.0 mM poly m-SBBV/HPTS-PEG Solutions After Addition of Glucose; Represented as the Area Under the Curve

| (Glucose) (mg/dl) | Area Under Curve |
|---|---|
| 0 | 26479.45 |
| 18 | 26934.93 |
| 36 | 27163.92 |
| 180 | 27988.86 |
| 360 | 28221.08 |
| 900 | 28810.57 |
| 1800 | 29434.23 |

Thus, the fluorescence intensity increase by 11% upon addition of 1800 mg/dl of glucose and 14.6% upon addition of 1800 mg/dl of fructose.

EXAMPLE 20

Fluorescence Spectroscopy Analysis of IPN: Copolymer of 4-N (Benzyl-3-Boronic Acid)-4'-N'-Benzyl-4-Ethenyl)-Dipyridinium Bromide Chloride (M-SBBV) Using Dispersed HPTS-MA Hydrogel See Example 12 for procedures.

A peristaltic pump was used to circulate 7.4 phosphate buffer (ionic strength 0.1) through the cell at a rate of 30 mL per minute.

The time drive function of the Perkin-Elmer LS50B software was used to acquire fluorescence intensity readings every ten seconds with an integration time of two seconds. The excitation frequency was set at 475 nm and the emission frequency was set at 536 nm. The excitation and emission slit width were set at 15 nm and 20 nm, respectively. A base line value of 249 (fluorescence intensity) was established with buffer solution. The peristaltic pump was stopped and the pumping solution was changed to 1800 mg/dl glucose in pH 7.4 phosphate buffer.

The fluorescence intensity increased 25 units to a value of 274, corresponding to a 10% signal increase (S/N ratio=43). After switching back to buffer the signal approached the expected baseline value of 249.

EXAMPLE 21

Fluorescence Spectroscopy Analysis of Two Component System: Thin Film Copolymer Hydrogel of 4-N-(Benzyl-3-Boronic Acid)-4'-N'-(Benzyl-4-Ethenyl)-Dipyridinium Bromide Chloride (M-SBBV) Using Acetoxy-HPTS-MA See Example 12 for analysis procedures.

A peristaltic pump was used to circulate pH 7.4 phosphate buffer (ionic strength 0.1) through the cell at a rate of 30 mL per minute. The time drive function of the Perkin-Elmer LS50B software was used to acquire fluorescence intensity readings every ten sec with an integration time of two sec. The excitation frequency was set at 475 nm and the emission frequency was set at 536 nm. The excitation and emission slit widths were set at 7 nm. A base line value of 490 (fluorescence intensity) was established with buffer solution. The peristaltic pump was stopped and the pumping solution was changed to 400 mg/dl glucose in pH 7.4 phosphate buffer.

The fluorescence intensity increased nine units to a value of 499, corresponding to a 1.5% signal increase (S/N ratio=6.5). The process of switching solutions was repeated. The buffer gave an expected base line of 490. After changing to 1800 mg/dl glucose in pH 7.4-phosphate buffer the fluorescence intensity rose 35 units to a value of 525, corresponding to a 7.6% signal increase (S/N=15.0). Finally, the base line dropped to the expected value of 490 when buffer was pumped through the system.

EXAMPLE 22

Fluorescence Spectrophotometric Determination of Glucose Concentration in an Aqueous Sample with 4,4'-N,N'-Bis(Benzyl-3-Boronic Acid)-Bipyridinium Dibromide (M-BBV) and 8-Hydroxypyrene-1,3,6-N,N',N"-Tris-(Methoxypolyethoxyethyl (N~125) Sulfonamide) (HPTS-PEG)

A stock solution of HPTS-PEG (10 ml, $5 \times 10^{-5}$ M) is prepared in a 10-mL volumetric flask with pH 7.4 phosphate buffer (0.1 ionic strength). Similarly, a m-BBV solution (25 mL, 0.0025 M) and -D-Glucose (10 mL, 0.250 M) solution are prepared. Seven different solutions containing HPTS-PEG, m-BBV, and -D-Glucose are then prepared in pH 7.4 phosphate buffer as described below in Table 5.

TABLE 5

| Volume HPTS-PEG Stock (mL) | Volume m-BBV stock (mL) | Volume Glucose Stock (mL) | Volume buffer (mL) | Final (HPTS-PEG) (M) | Final (m-BBV) (M) | Final (Glucose) (mg/dL) |
|---|---|---|---|---|---|---|
| 1 | 2 | 0.00 | 2.00 | 1.00E−05 | 1.00E−03 | 0.00 |
| 1 | 2 | 0.02 | 1.98 | 1.00E−05 | 1.00E−03 | 18.02 |
| 1 | 2 | 0.04 | 1.96 | 1.00E−05 | 1.00E−03 | 36.03 |
| 1 | 2 | 0.20 | 1.80 | 1.00E−05 | 1.00E−03 | 180.16 |
| 1 | 2 | 0.40 | 1.60 | 1.00E−05 | 1.00E−03 | 360.32 |
| 1 | 2 | 1.00 | 1.00 | 1.00E−05 | 1.00E−03 | 900.80 |
| 1 | 2 | 2.00 | 0.00 | 1.00E−05 | 1.00E−03 | 1801.60 |

The pH of each sample is independently determined using a pH meter to assure that the pH is constant throughout the series to within ±0.02 pH units.

See Example 17 for the analysis procedures.

Two mL of an aqueous glucose solution of unknown concentration are placed in a 5-mL volumetric flask to which is added 1 mL of HPTS-PEG stock solution and 2 mL of m-BBV stock solution. The sample is mixed, placed into an appropriate cuvet and the fluorescence emission intensity of the sample is analyzed as previously described. The fluorescence emission intensity is then quantified by integration (using the trapezoidal rule approximation method) of the fluorescence emission intensity curve between 480 and 630 nm. The glucose concentration for the unknown can be determined by comparison of the quantified value for the fluorescence emission intensity of the sample of unknown glucose concentration to the calibration curve on the y-axis and reading the corresponding glucose concentration on the x-axis. The glucose concentration read off the calibration chart is then adjusted for the 5/2 dilution factor to determine the glucose concentration of the unknown sample.

EXAMPLE 23

Fluorescence Spectrophotometric Determination of Glucose Concentration in an Aqueous Sample with the Thin Film Copolymer of 4-N-(Benzyl-3-Boronic Acid)-4'-N'-(Benzyl-4 Ethenyl)-Dipyridinium Bromide Chloride Using HPTS-PEG (Semi-IPN Thin Film)

The thin film copolymer is prepared as described in Example 11 and mounted in the fluorescence spectrometer as described in Example 12. Seven 100 ml stock solutions of -D-Glucose (0, 18, 36, 180, 360, 900, and 1800 mL/dL) are then prepared in pH 7.4 phosphate buffer. The 7 solutions are sequentially circulated through the flow through cell and the fluorescence emission intensities analyzed as described in Example 13. In each case the fluorescence emission intensity is allowed to stabilize prior to changing solutions. A calibration curve is constructed plotting the stabilized fluorescence intensity values vs. the corresponding glucose concentrations. The pH value of an aqueous glucose sample of unknown concentration is determined with a pH meter and adjusted to pH 7.4±0.02 with concentrated acid or base. The unknown sample is circulated through the flow through cell and the fluorescence emission intensity observed until it stabilizes. The glucose concentration for the unknown sample is circulated through the flow through cell and the fluorescence emission intensity observed until it stabilizes. The glucose concentration for the unknown can be determined by comparison of its quantified value for the stable fluorescence emission intensity to the calibration curve on the y-axis and reading the corresponding glucose concentration on the x-axis. The final determined glucose concentration for the unknown sample is adjusted for any dilution factor caused by adjusting the pH of the sample.

EXAMPLE 24

Synthesis of 4-N-(Benzyl-3-Boronic Acid)-4,7-Phenanthrolinium Bromide (4,7-Phen-m-BV

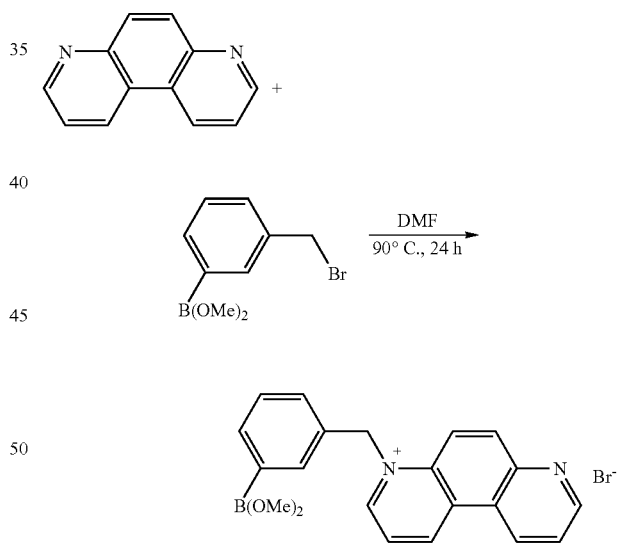

An oven-dried, 250-mL round bottom flask equipped with a magnetic stirring bar was cooled under argon, and charged with 4,7-phenanthroline (6.16 g, 34.2 mmols). The flask was equipped with a reflux condenser attached to an argon (g) line and charged with N,N-dimethylformamide (80 mL). The suspension was dissolved by heating and kept at 90° C. while freshly prepared dimethyl-(3-bromomethyl)-benzeneboronate (5.562 g, 22.8 mmols) was added via syringe. The reaction was monitored by TLC and after three hours showed the disappearance of the boronate ester. The reaction mixture was cooled to room temperature under argon (g) and the orange suspension transferred, via cannula, to a moisture sensitive fritted funnel. The salmon colored solid was collected, washed with acetone (4×50 mL) and dried under reduced pressure overnight. Yield: 3.652 g, 17.7 mmols (78%). $^1$H NMR (500 MHz, CD$_3$OD, ppm): 3.31 (s, 6H). 6.487 (s, 2H), 7.427 (mult., 2H), 8.002 (dd, 1H, J=10 Hz), 8.451 (dd, 1Hm J$_1$=6 Hz, J$_2$=8.5 Hz). $^{13}$C NMR (125 MHz, CD3OD): 61.48, 119.825, 123.258, 124.429, 124.493, 128.279, 128.472, 129.194, 132.161, 132.707, 133.990, 138.161, 139.107, 142.428, 146.358, 147.947, 153.080, 163.379. $^{11}$B NMR (80 MHz, MeOH, ppm): 27.4 (s, broad).

This compound was used in Example 31.

EXAMPLE 25

Synthesis of 4-N-(Benzyl-3-Boronic Acid)-N-7-(Benzyl-4-Ethenyl)-4,7-Phenanthrolinium Bromide Chloride (4,7-Phen-m-SBBV)

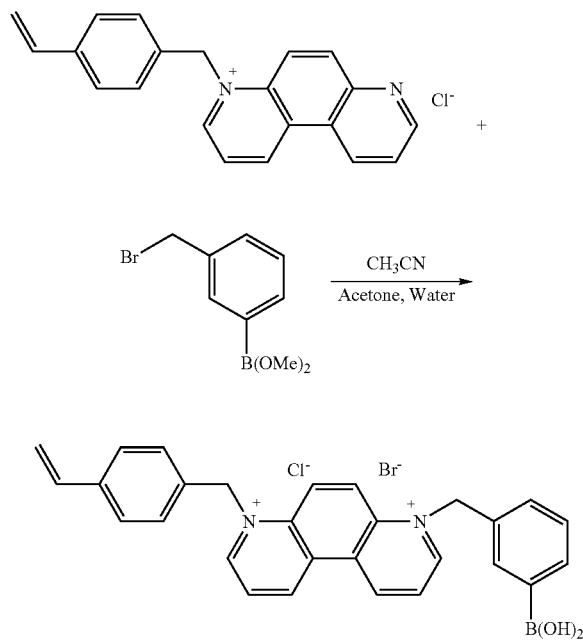

N-Benzyl-4-ethenyl-4,7-phenanthrolinium chloride (0.243 g, 0.730 mmols) was suspended in CH$_3$CN (2 mL) in a flame dried, sidearmed 25-mL round bottom flask, equipped with a magnetic stirring bar and reflux condenser. Dimethyl-(3-bromomethyl)-benzeneboronate (2.8 g, 11.5 mmols) was added via syringe through the side area and the suspension heated to reflux for 64 h under argon (g). The solution was cooled to room temperature and precipitated with diethyl ether (10 mL). The suspension was allowed to settle and the supernatant removed via cannula. The remaining residue along with 3 mL of solvent was cannulated into a centrifuge tube, triturated with acetone water (50/50, V/V, 20 mL), and centrifuged (process repeated four times). The beige/yellow solid was triturated with diethyl ether (3×20 mL) and dried under reduced pressure. Yield: 0.354 g, 0.615 mmols (84%). $^1$H NMR (250 MHz, D$_2$O, ppm): 5.223 (d, 1H, 11.25 Hz), 5.715 (d, 1H, J=17.75 Hz), 6.434 (d, 4H), 6.605 (dd, 1H, J$_1$=11.25 Hz, J$_2$=17.75 Hz), 7.446 (mult., 8H), 8.604 (mult., 1H), 8.92 (d, 2H, J=3.5 Hz), 9.698 (d, 2H, J=5.75 Hz), 10.214 (d, 2H, J=9 Hz). CH$_3$OH, ppm): 29.5 (s, broad). This compound was used in Example 26.

EXAMPLE 26

Two Component System: The Thin Film Copolymerization of 4-N-(Benzyl-3-Boronic Acid)-7-N'-(Benzyl-4-Ethenyl)-4,7-Phenanthrolinium Bromide Chloride (4,7-Phen-M-SBBV) and Acetoxy-HPTS-MA

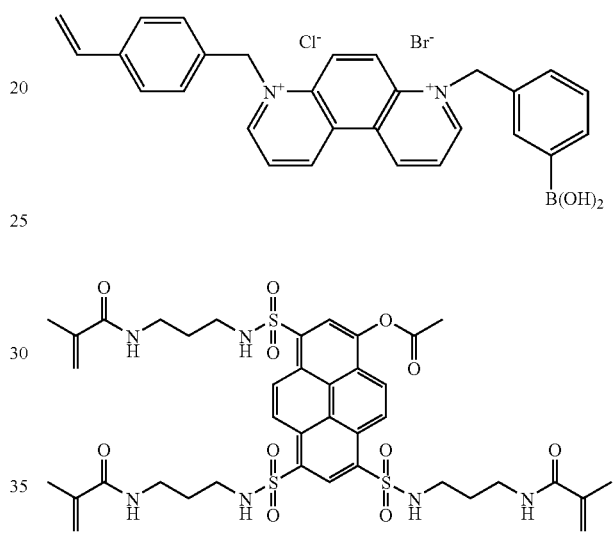

A 10-mL volumetric flask was charged with 2-hydroxy ethyl methacrylate (3.525 g, 27.08 mmols), 4,7-phenanthrolinium-(benzyl-3-boronic acid)-N'-(benzyl-4-ethenyl) bromide chloride (m-SBBV) (0.086 g, 0.15 mmols), 3-((methacryloylamino)propyl) trimethyl ammonium chloride (0.3 g, 1.36 mmols), polyethylene glycol dimethacrylate (1.11 g, 1.11 mmols), 2,2'-azobis (2-(2-imidazolin-2-yl)propane)dihydrochloride (0.025 g, 0.077 mmols) and 8-acetoxypyrene-1,3,6-N,N',N''-tris(methacrylamidopropylsulfonamide) (6.6×10$^{-4}$ g, 7.5×10$^{-4}$ mmols); it was filled to the 10-mL mark with isopropyl alcohol:water (1:1, V/V). After the solution was vigorously stirred on a vortex mixer it was transferred to an argon-filled glove box along with the polymerization chamber.* (*See Example 11.) The syringe was attached to the polymerization chamber and the solution was inserted into the cell, under argon, to fill the entire cavity. The chamber was sealed with LUER-LOC® plugs and wrapped in two ZIPLOC® Freezer bags. The entire unit was transferred to a 40° C. oven and heated for 18 hrs. The polymerization chamber was removed from the oven and allowed to reach room temperature. It was disassembled and the orange film was leached with a pH 8-NaOH solution for 7 hours effectively turning it green. The green film was stored in pH 7.4 phosphate-buffer for 14 hrs.

This polymer is characterized in Example 32.

EXAMPLE 27

Preparation of 8-Acetoxypyrene-1-Methacrylamido-propylsulfonamide-3,6-Biscarboxypropyl Disulfonamide (HPTS-CO$_2$MA) Disodium Salt

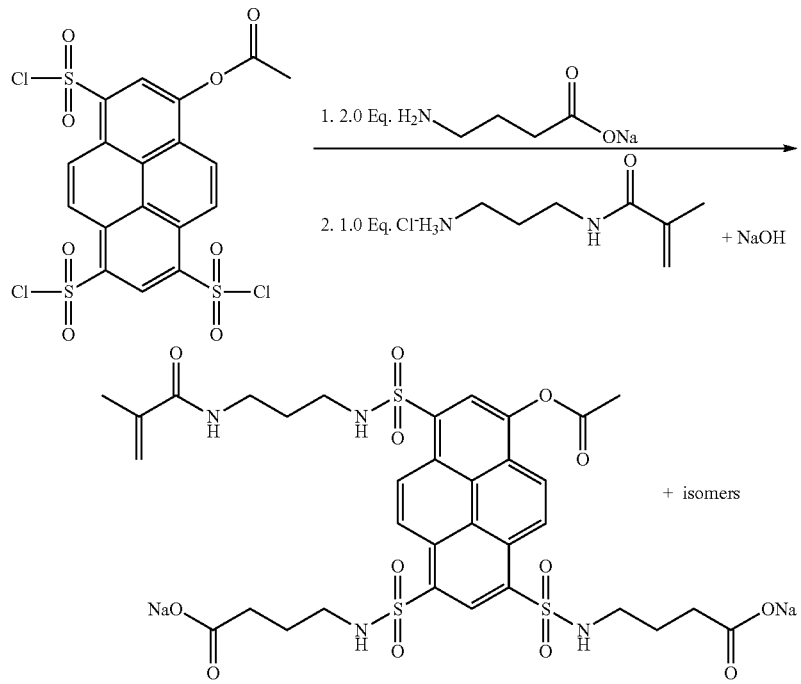

A 100-ml round bottom flask equipped with a stir) bar and rubber septum was charged with (1-acetoxy-3,6,8-pyrene trisulfonyl chloride) (0.5 mmols 272.91 mg) and 40 ml of THF. A sample of sodium 4-amino-butyrate (1 mmol, 125.10 mg) was placed into a small test tube with 2 ml of THF and 0.26 ml deionized water. The suspension was vortexed for a short period and taken up into a 3 ml plastic syringe. A sample of N-(3-aminopropyl)methacrylamide HCl was placed into a small test tube with 5 ml of THF and 0.55 ml of 1 M aqueous NaOH. The suspension was vortexed for a short period and taken up into a 10 ml plastic syringe. The solution in the 100 mL round bottom flask was stirred rapidly and charged with 5.2 ml deionized water, followed by dropwise addition of the sodium 4-amino-butyrate suspension to produce a bright red solution which faded to yellow after 10 min. of stirring. The flask was then charged with the N-(3-aminopropyl)methacrylamide. HCl suspension by dropwise addition again producing a red solution, which faded to yellow. The solution was stirred for 4 hr. After this period, the solvent was removed by rotoevaporation and then high vacuum. The solid in the flask was taken up into a minimum amount of methanol and precipitated with diethyl ether. The precipitate was collected by centrifugation and the precipitation repeated to produce the final product(s). $^1$H-NMR (500 MHz, CD$_3$OD ppm): 1.601 (M, J=8 Hz), 1.829 (Q, J=5 Hz), 2.392 (T, J=2.5 Hz), 2.584 (S), 2.890 (T, J=7.5 Hz), 2.933 (T, MHz), 5.519 (1), J=176.5 Hz), 8.306 (S), 8.526 (S), 8.616 (1), J=9.5 Hz), 9.062 (13, J=9.5 HZ), 9.130 (13, J=9.5 HZ), 9.225 (1), J=10 Hz), 9.305 (S), 9.317 (S), 9.338 (S), 9.358 (S), 9.440 (S). These are mixtures of specific isomers.

This product was used in Example 37.

EXAMPLE 28

Preparation of 8-Acetoxy-1,3,6-Pyrenetricarboxypropyl Sulfonamide (Acetoxy-HPTS-CO$_2$)

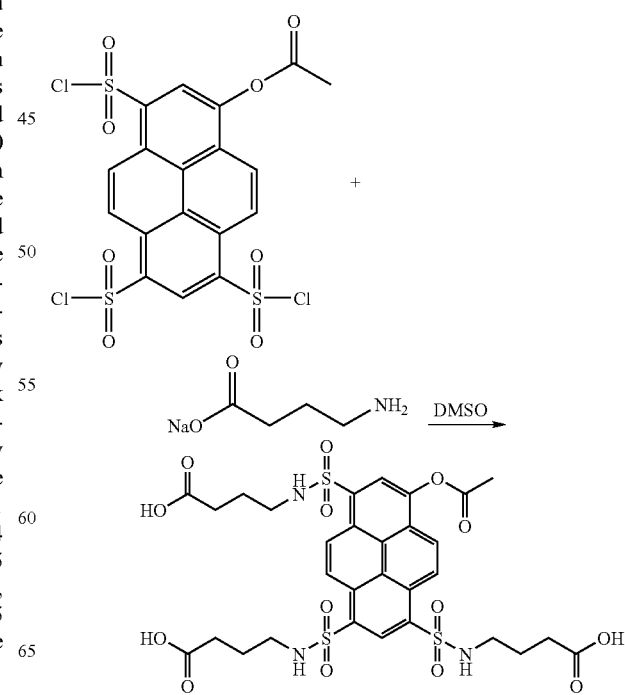

A round bottom flask was charged with 4-aminobutyric acid (5.156 g, 50 mmols). Methanol (50 mL) was added followed by sodium hydroxide (2 g, 50 mmols). The solution was stirred until it became homogeneous, at which point the methanol was removed on a rotary evaporator. The tan solid was further dried by coevaporations with acetonitrile to remove water.

Preparation of HPTS-$CO_2$:

An oven dried round bottom flask was cooled under argon, fitted with a magnetic stirring bar, charged with 8-acetoxy-1,3,6-pyrene trisulfonylchloride (460 mg, 0.83 mmols), and sealed with a septum. DMSO (20 mL) was added to give a homogenous yellow solution. A second oven dried round bottom flask was cooled under argon, fitted with a magnetic stirring bar, charged with the 4-aminosodiumbutyrate (415 mg, 3.32 mmols), and sealed with a septum. DMSO (20 mL) was added via double ended needle, and after a few minutes of stirring, the first solution containing 8-acetoxy-1,3,6-pyrene trisulfonylchloride in DMSO was cannulated in drop wise to give a deep red homogeneous solution. After six hours approximately one third of the solution was removed, and DMSO was distilled off under vacuum. The resulting brown material was washed with a small amount of acetonitrile, which was filtered through cotton and dripped into $Et_2O$ to precipitate a small amount (48 mg) of brown/red hygroscopic solid. $^1$H-NMR (250 MHz, $D_2O$, ppm): 2 (p, 6H), 2.4 (t, 6H), 2.61 (s, 3H), 3 (t, 6H), 8.2 (d, 1H), 8.4 (s, 1H), 8.6 (d, 1H), 9.2 (d, 1H), 9.4 (s, 1H).

The acetoxy protecting groups was removed by treatment with aqueous NaOH. The pKa value was then determined to be around 6.8.

The hydroxyl-material was then used in a Stern-Volmer quenching study with m-BBV and gave a Stern-Volmer quenching constant of 25419.

Following the Stern-Volmer study the HPTS-$CO_2$/m-BBV combination was used in a glucose response study. This combination showed sensitivity to small changes in glucose concentration, with a fairly linear response to glucose in the physiological range (0-400 mg/dL).

A glucose concentration study was performed using HPTS-$CO_2$ with 4,7-phen-BBV utilizing the Ocean Optics Inc. Model# SF 2000. Fiber Optics, 380 Main Street, Dunedin, Fla. 34698, spectrophotometer for fluorescence with a computer controller ADC 1000 Rev B and again it was observed that increasing glucose concentration gave increased fluorescence intensity.

EXAMPLE 29

Preparation of 2-(3,5-Bis-Bromomethyl-Phenyl)-(1,3,2)-Dioxaborinane

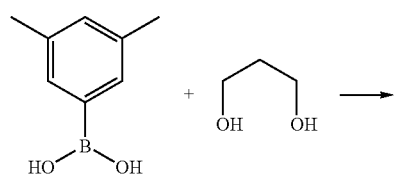

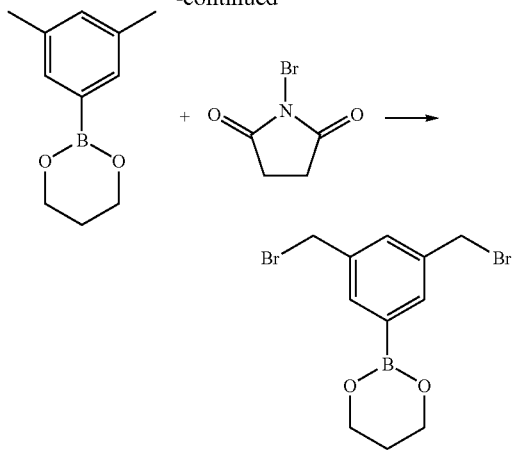

Preparation of the Boronic Ester:

An oven dried round bottom flask with side arm was cooled under nitrogen, fitted with a magnetic stir bar, and charged with 3,5-dimethylphenyl boronic acid, (5 g, 33 mmol) followed by pentane to produce a 0.5M heterogeneous solution. The flask was then fitted with an oven-dried reflux condenser, sealed with septum, and purged with nitrogen. The solution was stirred while 1,3-propanediol (14.5 mL) was added via double ended needle, then the solution was heated to reflux until it became homogenous (approximately 20 min.). The solution was cooled to room temperature under a nitrogen atmosphere. Magnesium sulfate and calcium chloride were quickly added, the apparatus was purged with nitrogen, and the solution was gently heated for 1 hr. The solution was then cooled to room temperature under nitrogen and stirring was stopped. The supernate was transferred to a separate oven dried round bottom flask, which had been cooled under nitrogen and sealed with a septum. The remaining solids were washed with pentane, and this was combined with the first pentane layer. The pentane was removed in vacuo on a rotary evaporator with an argon bleed to yield a yellow solid. MP: 58-60° C.

Dibromination:

An oven dried round bottom flask with side arm was cooled under nitrogen, fitted with a magnetic stir bar, charged with N-bromosuccinimide (13.4 g, 73.26 mmol) and AIBN (1.094 g, 6.66 mmol), fitted with a reflux condenser, sealed with a septum, and purged with nitrogen for several minutes. The boronic ester was dissolved in chloroform (250 mL, distilled over $CaH_2$) and cannulated into the round bottom containing N-bromosuccinimide and AIBN. The apparatus was vented through a nitrogen bubbler attached to an HBr trap consisting of aqueous sodium sulfite, and the solution was heated to a vigorous reflux while stirring. After 3.5 hr., the pale yellow solution was removed from heating and cooled to room temperature under nitrogen. The solution was concentrated in vacuo on a rotary evaporator with an argon bleed to give an orange solution from which succinimide byproduct was removed by filtration under argon. The filtrate was further concentrated on a rotary evaporator with an argon bleed to give a viscous, deep orange liquid. Pentane (~250 ml) was slowly added to this viscous liquid while stirring to precipitate the crude product. The pentane supernate was filtered and the solids were collected on a medium glass fritted filter under argon atmosphere. The solid was dried in vacuum to 60 millitorr. Yield: 71%. MP: 124-125° C. $^1$H-NMR (500 MHz, $CDCl_3$ 2.059-2.081 (quint, 2H, J=5.5 Hz), 4.163-4.185 (t, 4H, J=5.5 Hz), 4.5 (s, 4H), 7.479 (t, 1H), 7.721-7.725 (d, 2H, J=2 Hz). $^{13}$C-NMR (500 MHz, $CDCl_3$, ppm): 27.476, 33.262, 62.162, 131.845, 134.459, 137.694. $^{11}$B NMR (250 MHz, $CDCl_3$, ppm): 25.52.

This compound is used in Example 30 and 35.

EXAMPLE 30

Synthesis of 3-(3-Bromomethyl-5-(1,3,2)Dioxaborinan-2-Yl-Benzyloxy)-Propan-1-Ol

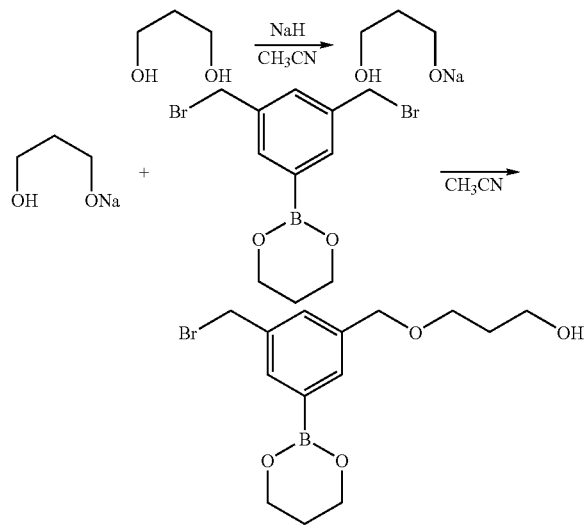

An oven-dried, 250-mL round bottom flask equipped with a magnetic stirring bar and reflux condenser was cooled under argon and charged with NaH (0.800 g of 60% in mineral oil, 20 mmols). The powder was washed with pentane (3×100 mL) and dried in vacuum. Acetonitrile (50 mL) was added by syringe and the mixture stirred at room temperature. 1,3-Propane diol (10 mL) was added dropwise over ten min. to form a white insoluble precipitate. The suspension was vigorously stirred for one hour at which time 20 mL was taken up by syringe and added dropwide to a 250-mL round bottom flask charged with 2-(3,5-Bis-bromomethyl-phenyl)-(1,3,2) dioxaborinane (2.865 g, 8.2 mmols) and acetonitrile (50 mL). The mixture was stirred for 12 hr at room temperature. A reflux condenser was attached along with a vacuum adapter and the reaction mixture was heated to reflux under argon for two hours. The acetonitrile was removed in vacuo and the residue purified by flash chromatography (EtOAc:hexane, 2:1). Removal of solvents gave a suspension of white solids in a yellow oil, which when analyzed by thin layer chromatography showed no starting material. The crude mixture containing 1,3-propane diol was used without further purification.

This compound was used in Example 31.

EXAMPLE 31

Synthesis of 4-N-(Benzyl-3-(Dimethyl)Boronate)-7-N-(Benzyl-3-(1,3,2))Dioxaborinan-2-Y-L)-5-Methylenoxy-Propanol-4,7-Phenanthrolinium Dibromide (4,7-Phen-M-BBVOH)

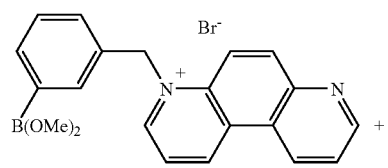

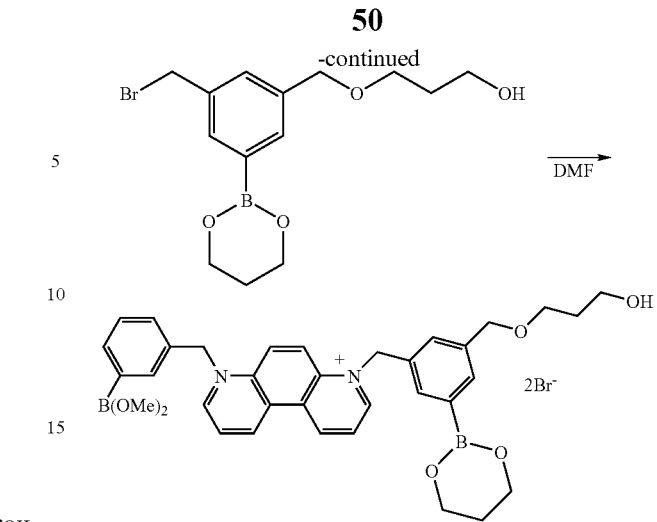

The material from Example 30 was retained in a 100-mL round bottom flask with a side arm, and the flask was equipped with a magnetic stirring bar and a reflux condenser. The flask was charged with 4-N-(benzyl-3-(dimethyl)boronate)-4,7-phenanthrolinium bromide (4,7-Phen-m-BV) (0.797, 1.88 mmols), DMF (4 mL), and CH$_3$OH (3 mL). The suspension was heated to 100° C. for 48 hrs and kept under a blanket of argon throughout the reaction. The reaction mixture was cooled to room temperature under argon and kept stirring. The suspension was cannulated into ice-cold diethyl ether (100 mL) and allowed to precipitate over one hr. The supernatant was cannulated to a separate vessel and the beige/red residue was triturated with THF (50 mL). The mixture was sonicated at 40° C. for 120 min and the resultant fine powder was washed with diethyl ether (3×50 mL). The solids were collected on a fritted funnel under argon and dried under reduced pressure (0.929 g, 49.4% yield).

This compound was used in Example 34.

EXAMPLE 32

Fluorescence Spectroscopy Analysis of Two Component System: Thin Film Copolymer Hydrogel of 4-N-(Benzyl-3-Boronic Acid)-7-N-(Benzyl-4-Ethenyl)-4,7-Phenanthrolinium Chloridebromide (4,7-Phen-M-SBBV) Using HPTS-MA

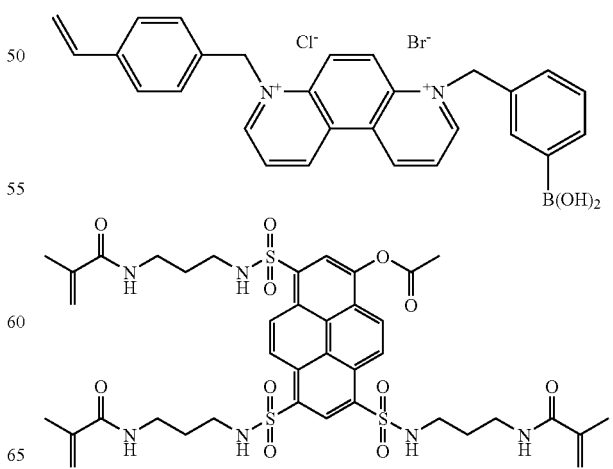

The fluorescence was measured according to the procedures of Example 17.

A base line value of 441 (fluorescence intensity) was established with buffer solution. The peristaltic pump was stopped and the pumping solution was changed to 400 mg/dl glucose in pH 7.4 phosphate buffer. The fluorescence intensity increased twelve units to a value of 453, corresponding to a 2.7% signal increase. The process of switching solutions was repeated. The solution was changed to 400 mg/dl fructose in pH 7.4 phosphate buffer. The buffer gave a base line of 443. The fluorescence intensity increased fourteen units to a value of 457, corresponding to a 3.2% signal increase. Finally, pH 7.4 phosphate buffer was pumped through the system to achieve a baseline of 446.

Figure 11:
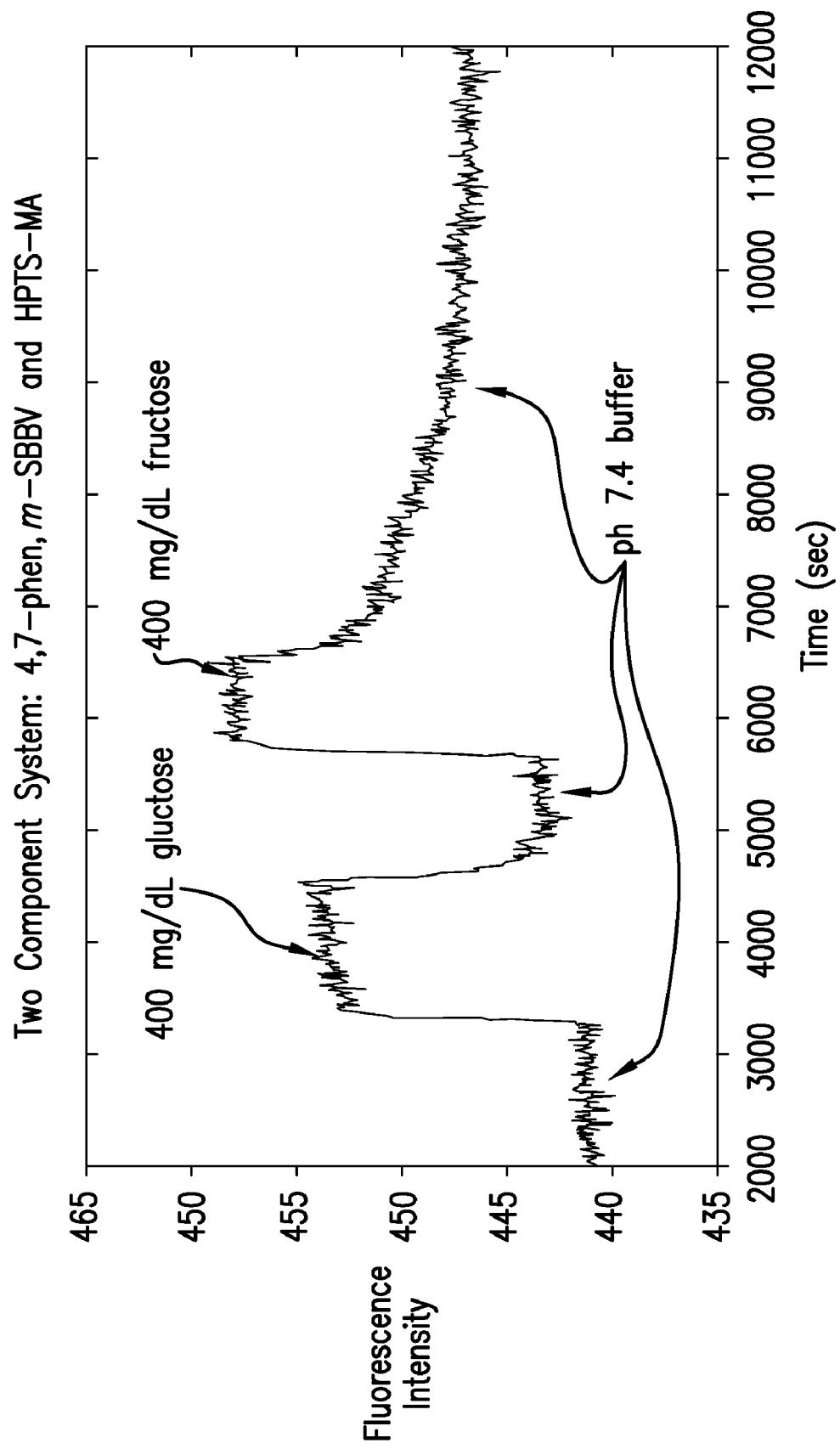
FIG. 11 is a graphic representation of the two component system of 4,7-phen m-SBBV and HPTS-MA, plotting fluorescence intensity versus time in seconds in a pH 7.4 buffer.
Figure 12A:
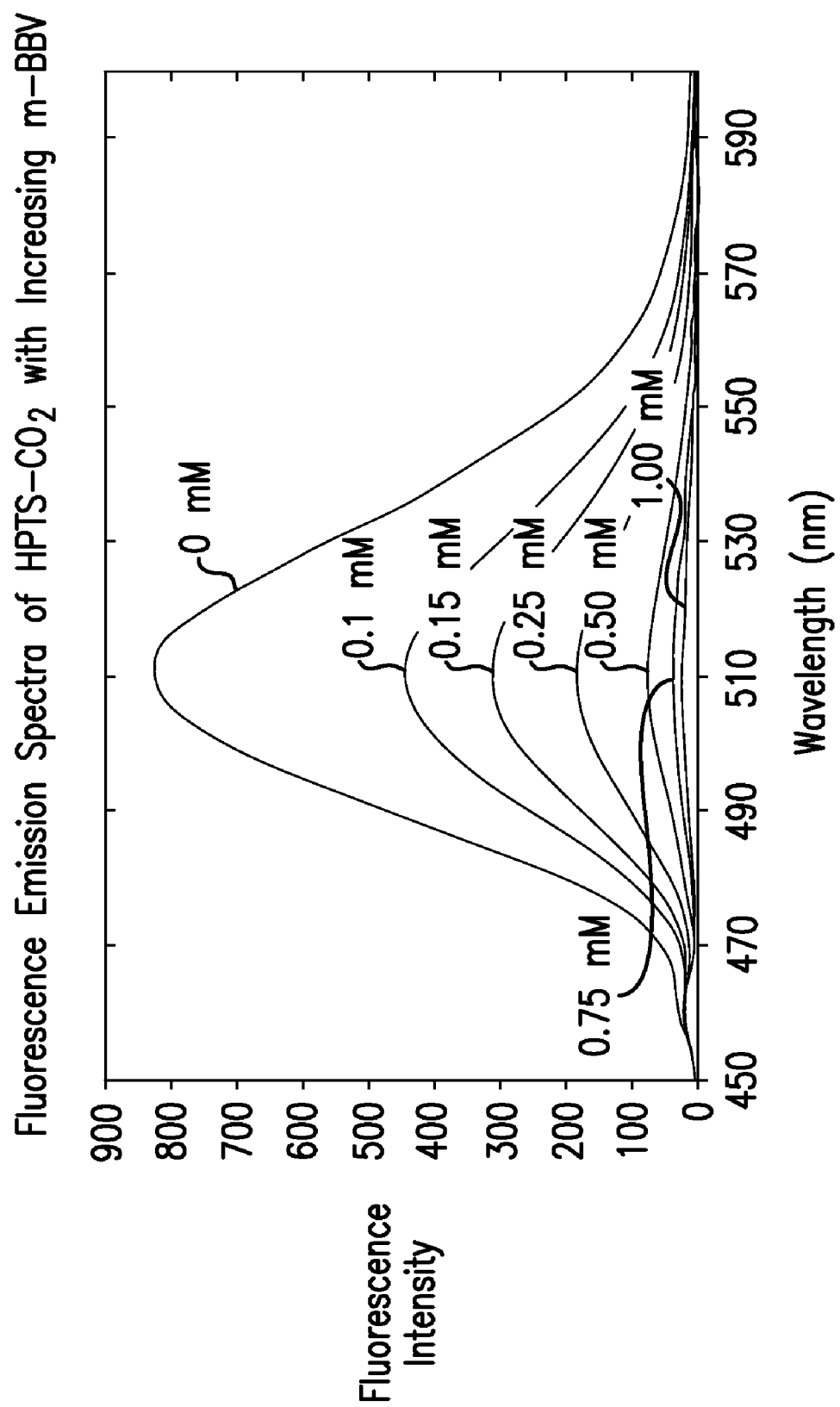
FIG. 12A is a graphic representation of the fluorescence emission spectra of 8-hydroxypyrene-1,3,6-N,N',N''-(carboxypropyl sulfonamide) (HPTS-$CO_2$) with increasing m-BBV. It plots fluorescence intensity versus wavelength (nm) from 0 to 1 mM.
Figure 12B:
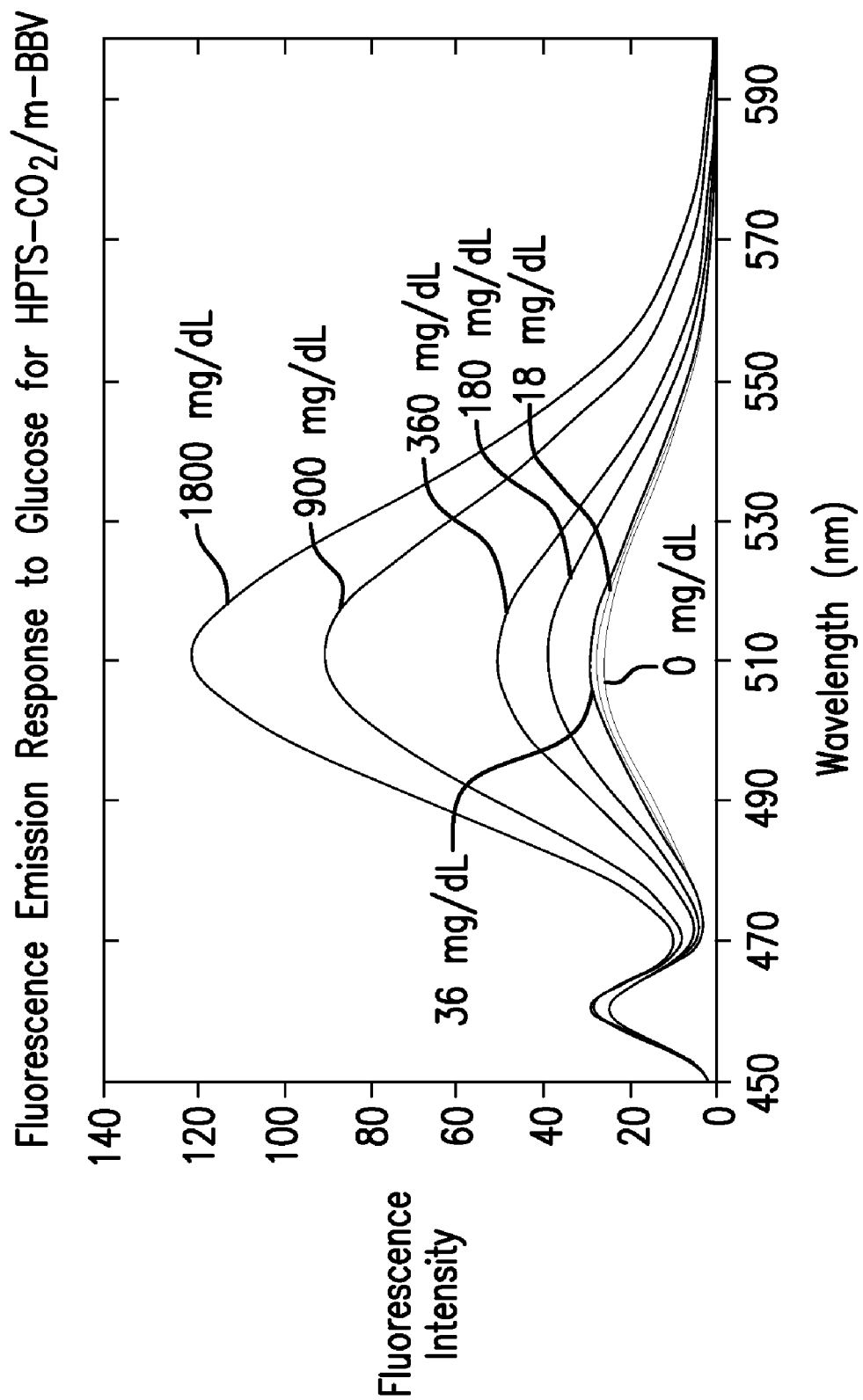
FIG. 12B is a graphic representation of the fluorescence emission response to glucose of 8-hydroxypyrene-1,3,6-N,N',N''-(carboxypropyl sulfonamide) (HPTS-$CO_2$)/m-BBV. It plots fluorescence intensity versus wavelength (nm) for 0 to 1800 mg/dL.
Figure 13:
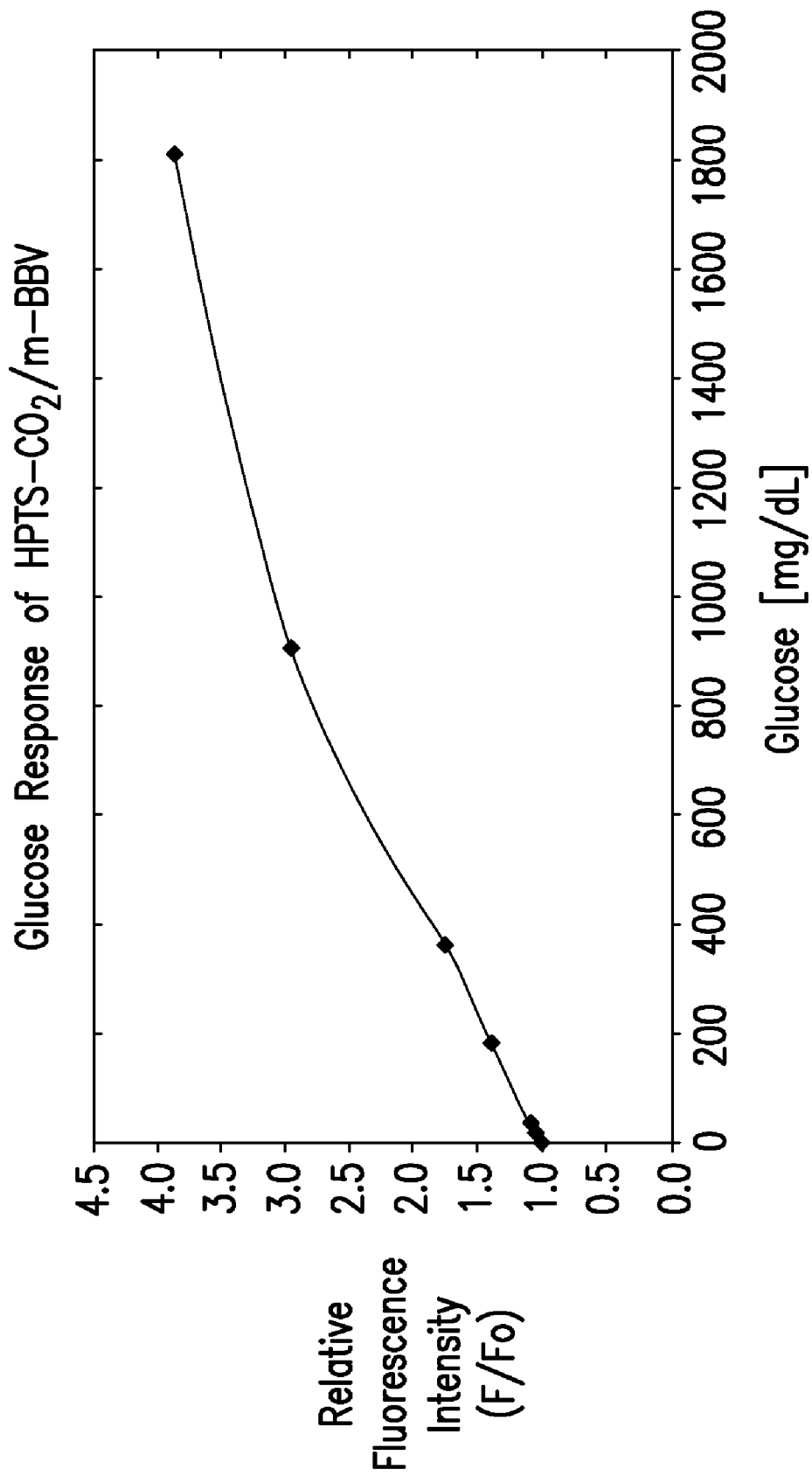
FIG. 13 is a graphic representation of the glucose response of 8-hydroxypyrene-1,3,6-N,N',N''-(carboxypropyl sulfonamide) (HPTS-$CO_2$) with m-BBV. It plots $F/F_o$ versus glucose (mg/dL).

These results are found in FIG. 11.

EXAMPLE 33

Synthesis of 4,7-N,N-Bis(Benzyl-3-Boronic Acid)-4-7-Phenanthrolinium Dibromide (4,7-Phen-M-BBV)

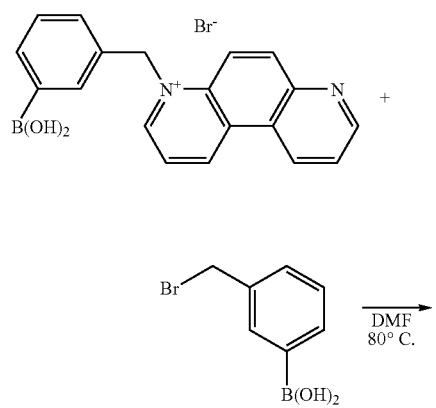

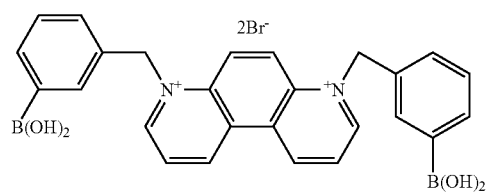

An oven-dried, 100-mL round bottom flask equipped with a magnetic stirring bar and reflex condenser was cooled under argon, and charged with 4,7-phen-m-BV (0.814 g, 1.92 mmols) and 3-bromomethylphenylboronic acid (1.77 g, 8.24 mmols). The system was purged with argon and charged with dry DMF (35 mL). The suspension was heated to 80° C. for 48 hours under a blanket of argon. The mixture was cooled to room temperature under argon and dripped into ice-cold diethyl ether:acetone (1:1, 500 mL) containing 1 M HCl (10 drops). The precipitate was filtered and washed multiple times with cold acetone and subsequently dried under reduced pressure. Yield: 0.913 g, 1.50 mmols (78%). $^1$H NMR (250 MHz, CD$_3$OD, ppm): 6.526 (s, 4H), 7.668 (m, 4H), 7.426 (m, 4H), 8.660 (q, 2H, J=4.5 Hz), 9.833 (d, 2H, J$_1$=6 Hz), 9.117 (s, 2H), 10.387 (d, 2H, J=9 Hz).

$^{11}$B NMR (80 MHz, CD$_3$OD, ppm): 30 (s, broad). This compound quenched the dye of Example 28 and responded to glucose.

This compound was evaluated according to the procedures of Example 17. The Stern-Volmer quenching constant was 2598M$^{-1}$.

The glucose response was measured using 180 mg/dL, the fluorescence intensity changed from 257 to 291.

EXAMPLE 34

Synthesis of 4-N-(Benzyl-3-(Boronic Acid)-7-N-[Benzyl-3-(Methylene-(1-Oxy-3-(Oxybenzylvinyl)-Propane))-5-Boro-Nic Acid]-4,7-Phenanthrolinium Dibromide

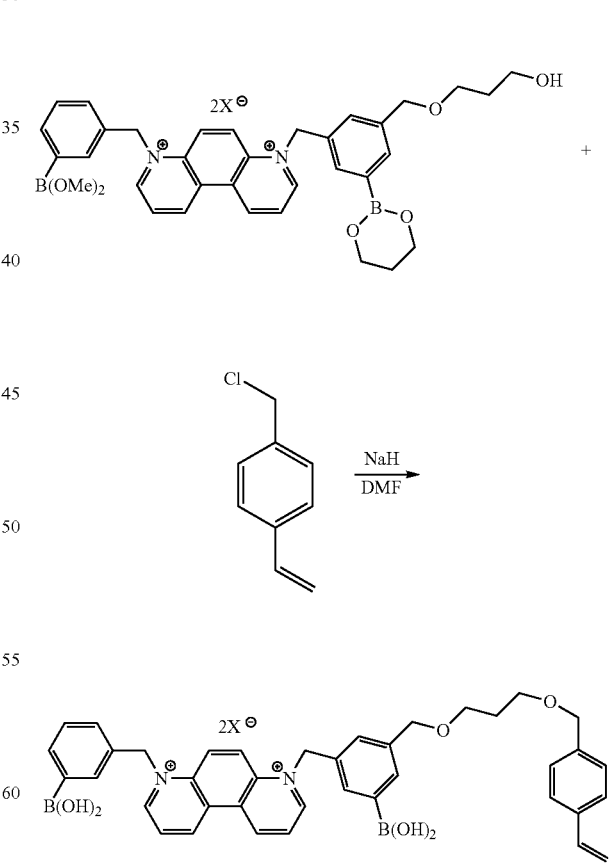

An oven-dried, 100-mL round bottom flask equipped with a magnetic stirring bar was charged with 4,7-phen m-BBVOH (0.491 g, 0.641 mmols) and 4-vinylbenzylchloride (0.137 g, 0.9 mmols). Freshly activated NaH (0.048 g, 2 mmols) was suspended in DMF (10 mL) and cannulated into the 100-mL flask. The mixture was stirred at room temperature for 46 hr then quenched with acetone (30 mL) and 1 M HCl (10 drops), and allowed to stir overnight (20 hr). The suspension was dripped into cold diethyl ether (200 mL) and the precipitate allowed to settle. The supernatant was removed after centrifugation and the residue dissolved in the minimum amount of methanol. Acetone:diethyl ether (1:1, 20 mL) was added and the precipitate was kept at 4° C. overnight. The suspension was filtered and washed with diethyl ether multiple times and dried under reduced pressure. Yield: 0.201 g, 0.247 mmols, 38.5%). $^1$H-NMR (500 MHz, D$_2$O, ppm): 1.73 (d, 2H), 3.581 (d, 2H), 3.707 (d, 2H), 4.7 (s, 4H), 5.565 (d, 1H), 6.090 (d, 1H), 6.554 (m, 8H), 6.980 (dd, 1H), 7.66 (m, 7H), 8.150 (d, 1H), 8.737 (d, 1H), 8.804 (d, 1H), 9.261 (d, 1H), 9.515 (d, 1H), 9.605 (d, 1H), 10.024 (d, 1H), $^{11}$B NMR (80 MHz, CD$_3$OD, ppm): 30 (s, broad). This compound quenched the dye of Example 28 and showed a response to glucose.

EXAMPLE 35

Preparation of 4,4'-N,N-Bis-[Benzyl-(3-Bromomethyl)-5-(Boronic Acid)]-Dipyridinium Dibromide (M-BBVBBR)

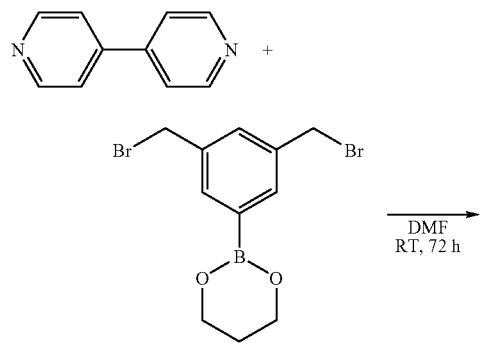

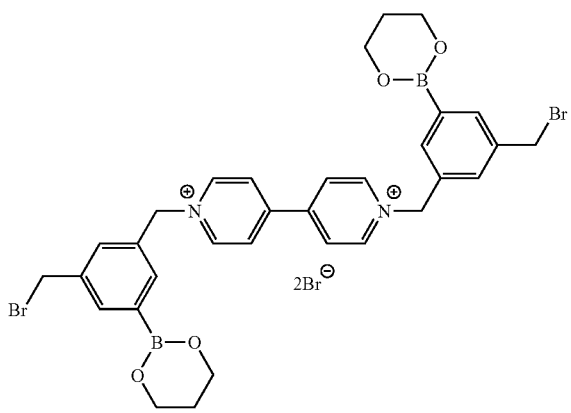

An oven-dried, 100-mL round bottom flask equipped with a magnetic stirring bar was cooled under argon, and charged with 4,4'-dipyridyl (0.394 g, 2.52 mmols) and 2-(3,5-bis-bromomethyl-phenyl)-[1,3,2]dioxaborinane (2.63 g, 7.56 mmols) and sealed with a septum. The flask was purged with argon and charged with N,N-dimethylformamide (10 mL). The solution was stirred at room temperature for 72 hr and the resultant suspension cannulated, via a plastic cannula, to an acetone:diethyl ether:solution (1:1, 300 mL). The precipitate was filtered through an air sensitive fritted funnel and washed multiple times with diethyl ether under a blanket of argon. The bright yellow solids were dried under reduced pressure and isolated under argon. Yield: 1.632 g, 1.92 mmols, 76%.

The compound was used in Example 36.

EXAMPLE 36

Synthesis of 4,4'-N,N-Bis-[Benzyl-(3-Methylene-4-Vinyl-Pyridinium Bromide)-5-(Boronic Acid)]-Dipyridinium Dibromide) (M-BBVBP)

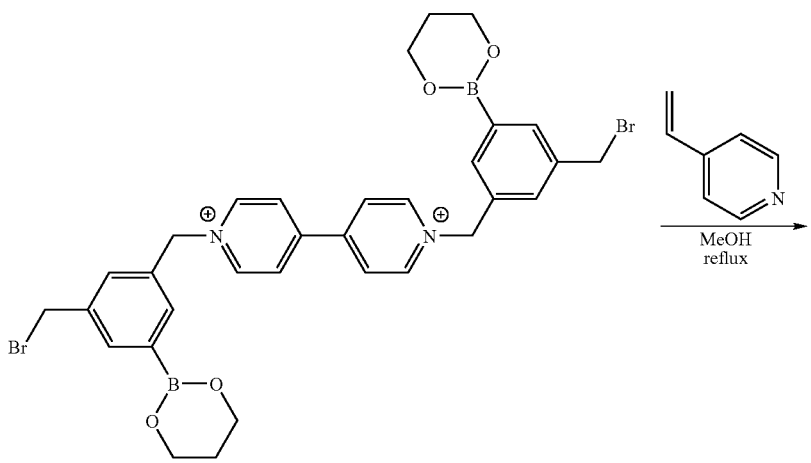

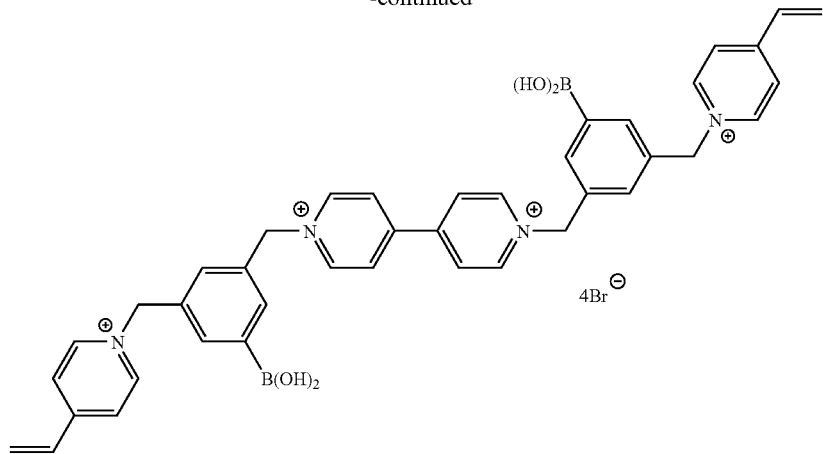

An oven-dried, side-armed 50-mL round bottom flask equipped with a magnetic stirring bar and reflux condenser was cooled under argon, and charged with m-BBVBBr (500 mg, 0.587 mmols). The solid was dissolved in the minimum amount of anhydrous $CH_3OH$ (6 mL) and 4-vinylpyridine (63 mg, 0.60 mmols) was added through the side arm. The solution was stirred at room temperature for 15 h and then heated to reflux for six hr. Additional 4-vinylpyridine (63 mg, 0.60 mmols) was added and the mixture refluxed for 4 days. The dark green solution was cooled to room temperature under argon and the $CH_3OH$ removed in vacuum. The crude oil was vigorously stirred with acetone:water (40:1) along with 1M HCl (5 drops) 4×30 mL for ten min and the supernatant decanted. The residue was recrystallized from boiling methanol:ethanol (1:1, 50 mL) to yield dark green crystals. The solids were collected onto a fritted funnel and washed with ice-cold ethanol (95% in water) and diethyl ether. Subsequent drying under reduced pressure gave a pea-green powder. Yield: 0.446 g, 0.506 mmols, 86%. $^1$H NMR (500 MHz, $D_2O$, ppm): 5.87 (m, 2H), 6.055 (m, 8H), 6.400 (m, 2H), 7.44 (d, 2H), 7.899 (m, 6H), 8.612 (d, 8H), 9.225 (d, 8H). $^{11}$B NMR (80 MHz, $CD_3OD$, ppm): 30 ppm (s, broad).

The compound was used in Examples 37 and 40.

EXAMPLE 37

Two Component System: The Thin Hydrogel Copolymerization of M-BBVBP with HPTS-$CO_2$ MA Hydrogel

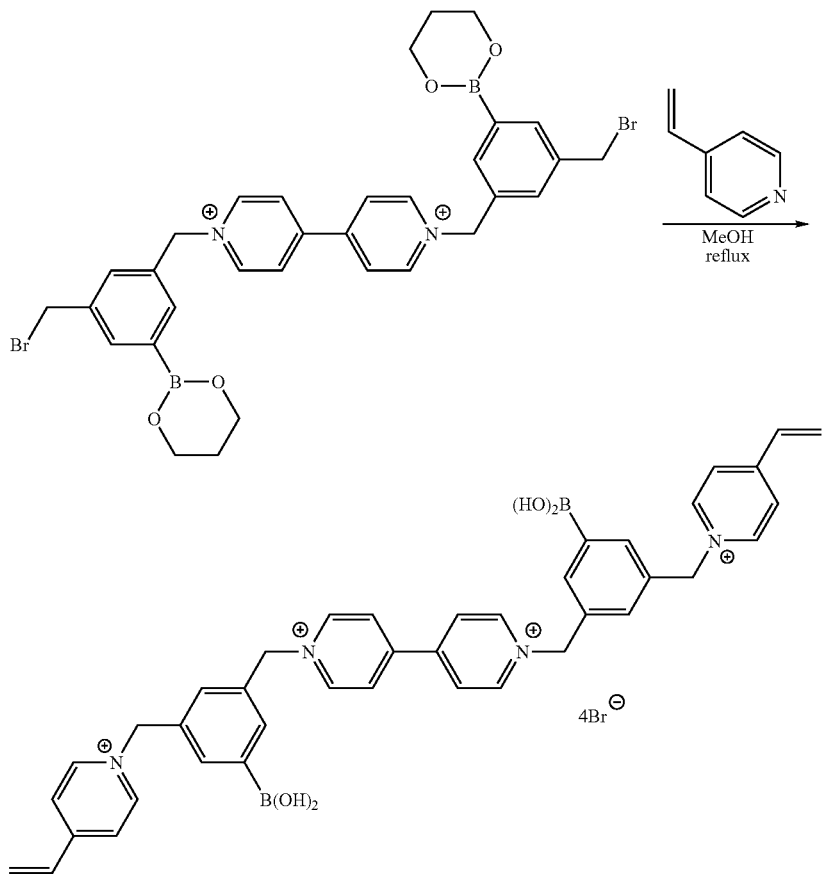

A 10-mL volumetric flask was charged with 2-hydroxyethyl methacrylate (3.525 g, 27.08 mmols), m-BBVBP (0.617 mg, $7.5 \times 10^{-4}$ mmols), polyethylene glycol dimethacrylate (1.11 g, 1.11 mmols), 2,2'-azobis[2-(2-imidazolin-2-yl)propane]dihydrochloride (0.025 g, 0.077 mmols) and HPTS $CO_2$ MA (1.26 mg, $1.5 \times 10^{-3}$ mmols); it was filled to the 10-mL mark with methanol:water (1:1, V/V). After the solution was vigorously stirred on a vortex mixer, it was transferred to a 50-mL round bottom flask and the flask was sealed with a rubber septum. It was deoxygenated with argon for 20 minutes. The monomeric solution was taken-up by syringe and the needle was capped with a rubber stopper. It was then transferred to an argon-filled glove box along with the polymerization chamber described in Example 16. The syringe was attached to the polymerization chamber and the solution was inserted into the cell, under argon, to fill the entire cavity. The chamber was sealed with LUER-LOC® plugs and wrapped in two ZIPLOC® Freezer bags. The entire unit was transferred to a 40° C. oven and heated for 18 hrs. The polymerization chamber was removed from the oven and allowed to reach room temperature. It was disassembled and the orange film was leached with a pH 8-NaOH solution for 7 hours effectively turning it green. The green film was stored in pH 7.4 phosphate-buffer for 14 hrs.

The green film was stored in pH 7.4 phosphate buffer until used in Example 38.

EXAMPLE 38

Fluorescence Spectroscopy Analysis of Two Component System: Thin Film Copolymer Hydrogel of 4,4'-N,N-Bis-(Benzyl-(3-(Methylene-4-Vinylpyridinium-bromide)-5-(Boronic Acid))]-Dipyridinium Dibromide Using HPTS-$CO_2$ MA

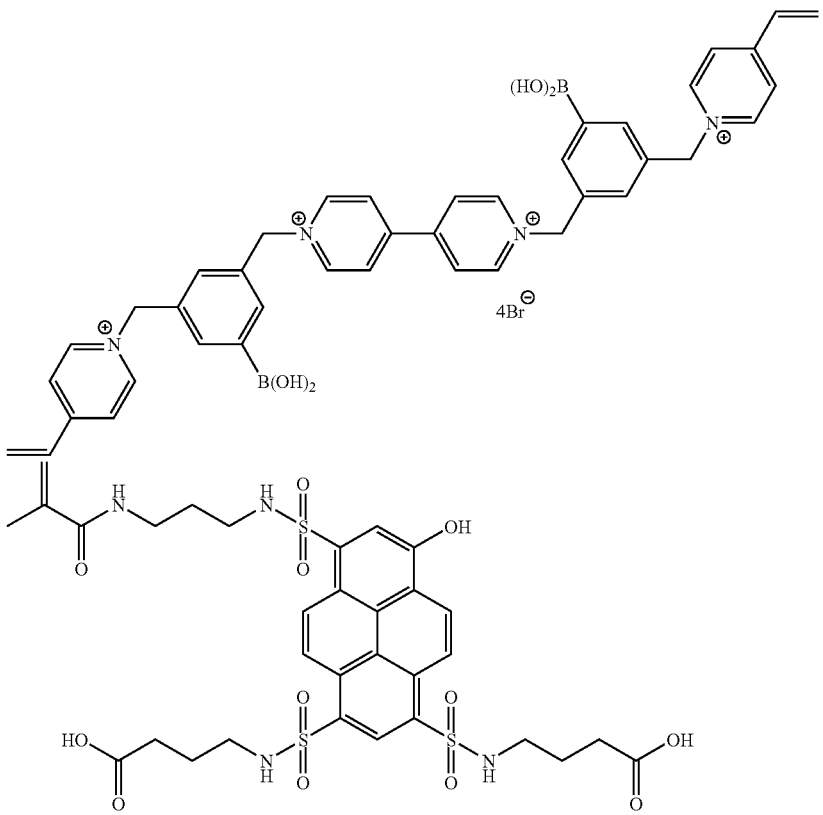

The fluorescence was measured according to the procedures of Example 12.

The time drive function of the Perkin-Elmer LS50B software was used to acquire fluorescence intensity readings every ten seconds with an integration time of two seconds. The excitation frequency was set at 463 nm and the emission frequency was set at 518 nm. The excitation slit width was set at 15 nm and the emission at 4.3 nm. A base line value of 451 (fluorescence intensity) was established with buffer solution. The peristaltic pump was stopped and the pumping solution was changed to 360 mg/dl glucose in pH 7.4 phosphate buffer. The fluorescence intensity increased 29 units to a value of 458, corresponding to a 1.6% signal increase. The process of switching solutions was repeated. The buffer gave an expected base line of 451.

EXAMPLE 39
A Single Component Viologen Sensor HPTS-BV
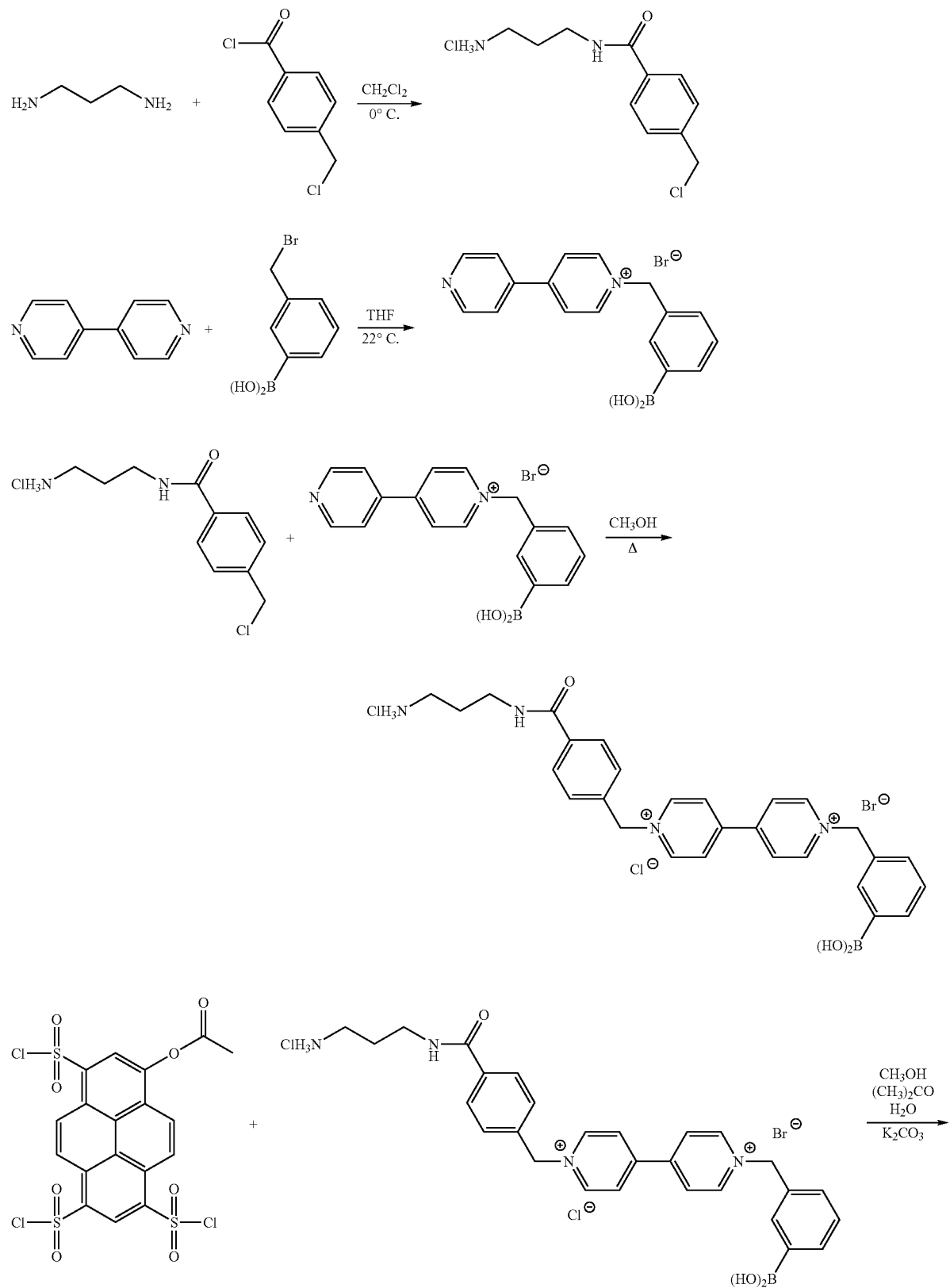

-continued

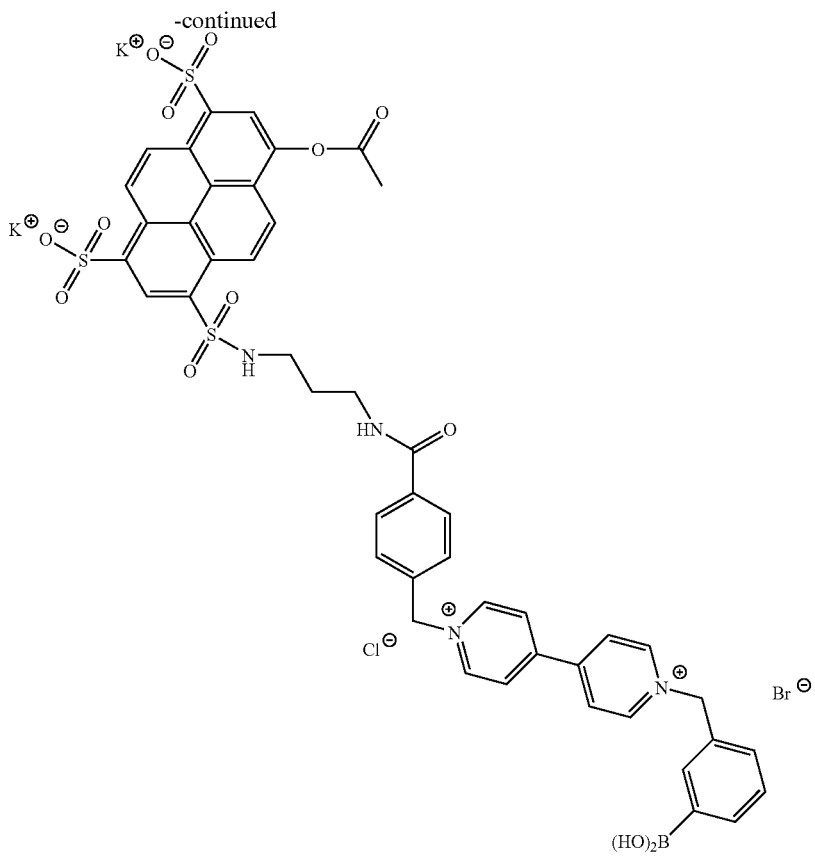

(a)—An oven dried round bottom flask was cooled under argon, fitted with a magnetic stirring bar, charged with 4-chloromethylbenzoylchloride (1.89 g, 10 mmols), and sealed with a rubber septum. Dichloromethane (25 mL) was added and the solution was stirred and cooled on an ice water bath. 1,3-Propanediamine (0.89 g, 12 mmol) was added drop wise causing an immediate white precipitate. The white solid was collected under argon on a medium fritted glass filter and washed with cold dichloromethane. The white solid was dried under vacuum (100 mtorr, 3 h) to give 2.61 grams (99% yield) of 4-chloromethylbenzoyl-(1-amidopropyl-3-ammonium chloride). $^1$H NMR (500 MHz, D$_2$O, ppm): 1.7-1.8 (m), 2.5, 2.8 (t), 3.3 (q), 4.8 (s), 7.5 (d), 7.8 (d), 8.6 (t).

(b) (m-BV)—An oven dried round bottom flask was cooled under argon, fitted with a magnetic stirring bar, charged with 3-bromomethylphenylboronic acid (0.64 g, 3 mmols), and sealed with a rubber septum. THF (50 mL) was added to give a slightly cloudy yellow solution. A second oven dried round bottom flask was cooled under argon, fit with a magnetic stir bar, charged with 4,4'-bipyridine (1.87 g, 12 mmols), and sealed with a rubber septum. THF (5 mL) was added via double ended needle, and after a few minutes of stirring, the solution containing 4,4'-bipyridine in THF was added drop wise to the 3-bromomethylphenylboronic acid solution. After 30 minutes some yellow precipitate begins to form, the solution was stirred at room temperature overnight and a large amount of precipitate formed. The solution was then centrifuged and the supernatant transferred via double ended needle. The yellow solid was washed with THF (3×10 mL) and dried under vacuum (100 mtorr, 3 h) to give 0.88 grams (79% yield) mBV. $^1$H NMR (500 MHz, CD$_3$OD, ppm): 5.9 (s), 7.46 (m), 7.6 (m), 8.0 (m), 8.5, 8.7, 9.2; $^{11}$B NMR (250 MHz, CD$_3$OD, ppm): 30.8

(c) m-ABBV—An oven dried round bottom flask was cooled under argon, fitted with a magnetic stirring bar, charged with 4-chloromethylbenzoyl-(1-amidopropyl-3-ammonium chloride) (263 mg, 1 mmol) and sealed with a rubber septum. Methanol (30 mL) was added and the solution stirred. mBV (371 mg, 1 mmol) was dissolved in methanol (10 mL) and added drop wise to the solution containing 4-chloromethylbenzoyl-(1-amidopropyl-3-ammonium chloride). The solution was heated to reflux. After 48 hours the solution was cooled to room temperature under argon. 10 mL of the solution was removed with a syringe and precipitated in acetone (100 mL). The supernatant was decanted off and the white solid collected and dried under vacuum to give 44 mg of m-ABBV. $^1$H NMR (500 MHz, D$_2$O, ppm): 2.1, 2.2, 3.45, 4.9, 6.0, 7.6, 8.6, 9.2; $^{11}$B NMR (250 MHz, CD$_3$OD, ppm): 31.7.

(d) AIO—An oven dried round bottom flask was cooled under argon, fitted with a magnetic stirring bar, charged with m-ABBV (44 mg, 0.075 mmol) and sealed with a rubber septum. Methanol (10 mL) was added followed by water (2 mL). K$_2$CO$_3$ was added and the solution stirred. 1-Acetoxy-3,6-8-trisulfonylchloride (acetoxy-HPTS-Cl) (38 mg, 0.068 mmol) was dissolved in methanol (15 mL) to give a yellow suspension, acetone (5 mL) was added to give a homogeneous solution. The acetoxy-HPTS-Cl solution was added to the m-ABBV dropwise via syringe. The solution immediately became red and after a few minutes of stirring a precipitate began to form. The solution was stirred at room temperature overnight, then transferred to a centrifuge tube. After centrifugation the supernatant was transferred to a round bottom flask and concentrated on a rotary evaporator. Residual water was removed by co-evaporation with acetonitrile, and the resulting black solid was dried under vacuum to give 55 mg (70% yield) of 8-acetoxy-1-m-ABBV-pyrene-3,6-bissulfonic acid (AIO). $^1$H NMR (500 MHz, D$_2$O, ppm): 2.01-2.08, 2.14, 2.8, 3.1, 3.4, 5.7, 5.88, 7.45, 7.55, 7.7, 7.8, 7.99, 8.07, 8.17, 8.6, 8.7, 8.8, 8.9, 9.05.

(e) The final isolated material was then used in a glucose study as described in Example 17. First a 5×10$^{-4}$ M stock solution of AIO was prepared in a 25 mL volumetric flask, but before diluting completely with pH 7.4 (0.1 ionic strength) phosphate buffer the solution was made basic (pH 10) to ensure all the acetoxy protecting group was removed. The solution was then adjusted back to pH 7.4 and diluted to 25 mL. Next a 5×10$^{-5}$ M stock solution was then used to prepare seven 5 ml samples with varying amounts of glucose. The analysis was done on a Perkin-Elmer LS50-B luminescence spectrometer with the following instrument settings:

TABLE 6

| | |
|---|---|
| Excitation Wavelength | 463 nm |
| Emission Wavelength Range | 450-650 nm |
| Excitation Slit Width | 15 nm |
| Emission Slit Width | 15 nm |
| Emission Filter | 1% T attenuator |
| Scan Speed | 100 nm/sec |

This compound was highly responsive to glucose. Addition of 18 mg/dL resulted in a signal increase from 827 to 908. See FIG. 14. Addition of more concentrated glucose solutions did not cause any additional increase in fluorescence intensity due to the material being saturated with small amounts of glucose.

EXAMPLE 40

Two Component System

The Thin Film Copolymerization of M-BBVBP with HPTS MA

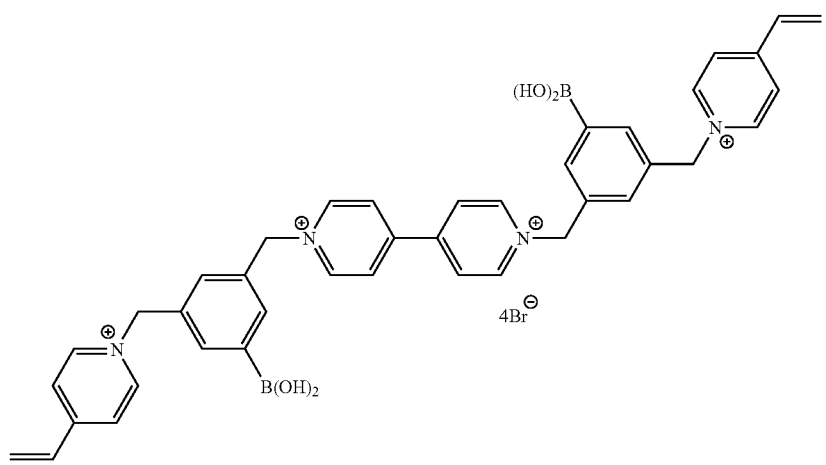

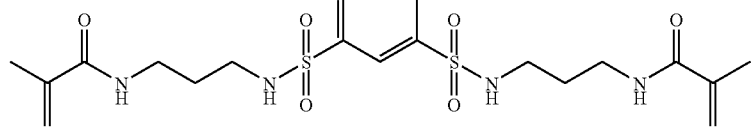

A 10-mL volumetric flask was charged with 2-hydroxy ethyl methacrylate (3.525 g, 27.08 mmols), m-BBVBP (12.3 mg, 0.015 mmols), polyethylene glycol dimethacrylate (1.11 g, 1.11 mmols), 2,2"-azobis[2-(2-imidazolin-2-yl)propane] dihydrochloride (0.025 g, 0.077 mmols) and HPTS MA (1.32 mg, $1.5 \times 10^{-3}$ mmols). It was filled to the 10-mL mark with methanol:water (1:1, V/V). After the solution was vigorously stirred on a vortex mixer it was transferred to a 50-mL round bottom flask and the flask was sealed with a rubber septum; it was deoxygenated with argon for 20 minutes. The manometric solution was taken-up by syringe and the needle was capped with a rubber stopper. It was then transferred to an argon-filled glove box along with the polymerization chamber.* (*See Ex. 11) The syringe was attached to the polymerization chamber and the solution was inserted into the cell, under argon, to fill the entire cavity. The chamber was sealed with LUER-LOCK® plugs and wrapped in a ZIPLOC® freezer bag. The entire unit was transferred to a 40° oven and heated for 10 hrs. The polymerization chamber was removed from the oven and allowed to reach room temperature. It was disassembled and the film was leached with a pH 8 NaOH solution for four hours. The film was stored in pH 7.4 phosphate buffer until analyzed in Example 41.

EXAMPLE 41

Fluorescence Spectroscopy Analysis of Two Component System: Thin Film Copolymer Hydrogel of 4,4'-N,N-Bis-[Benzyl-(3-Methylene-4-Vinylpyridinium-bromide)-5-(Boronic Acid)]-Dipyridinium Dibromide (M-BBVBP) Using HPTS-MA See Example 12 for analysis procedure.

A peristaltic pump was used to circulate pH 7.4 phosphate buffer (ionic strength 0.1) through the cell at a rate of 30 mL per minute. The time drive function of the Perkin-Elmer LS50B software was used to acquire fluorescence intensity readings. The sample was irradiated using the pulse function (every two seconds) and readings captured every ten seconds with an integration time of two sec. The excitation frequency was set at 475 nm and the emission frequency was set at 525 nm. The excitation slit width was set at 15 nm and the emission at 4 nm. A base line value of 464 (fluorescence intensity) was established with buffer solution. The peristaltic pump was stopped and the pumping solution was changed to 360 mg/dl glucose in pH 7.4 phosphate buffer. The fluorescence intensity increased 29 units to a value of 493, corresponding to a 6.3% signal increase. The process of switching solutions was repeated. The buffer gave an expected base line of 464. After changing to 100 mg/dl glucose in pH 7.4 phosphate buffer the fluorescence intensity rose 20 units to a value of 484, corresponding to a 4.3% signal increase. Finally, the base line dropped to the expected value of 464 when buffer was pumped through the system.

Figure 14:
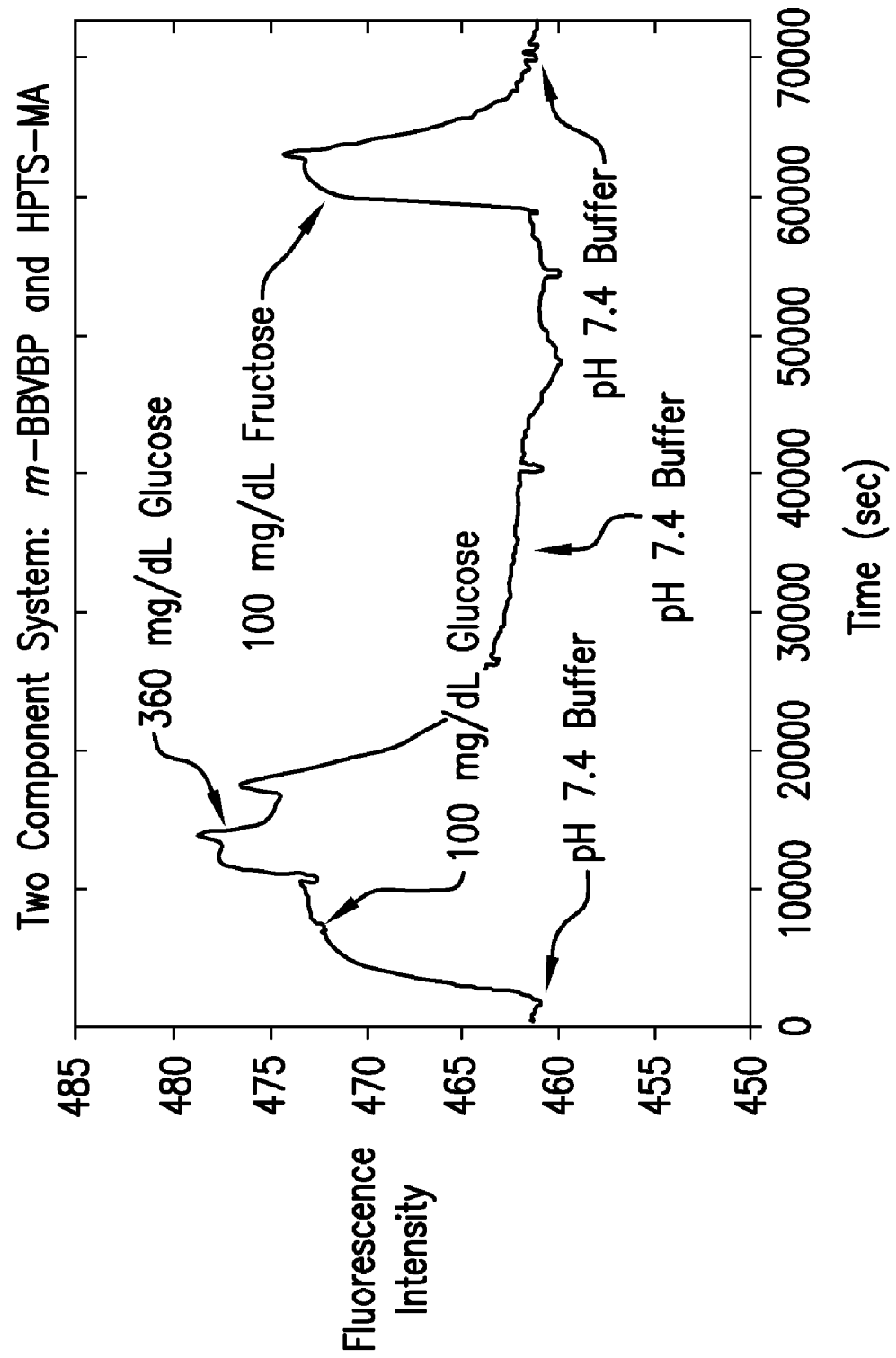
FIG. 14 is a graphic representation of fluorescence intensity versus time (sec) for a two component system of m-BBVBP and HPTS-MA.

The results are found in FIG. 14.

EXAMPLE 42

Preparation of PMMA

A 1 mm thick piece of PMMA is cut to the size of a polymerization chamber with a dremel tool. The PMMA is then cleaned with hexanes on a kimwipes, followed by isopropanol on a kimwipes, and subsequently placed in and

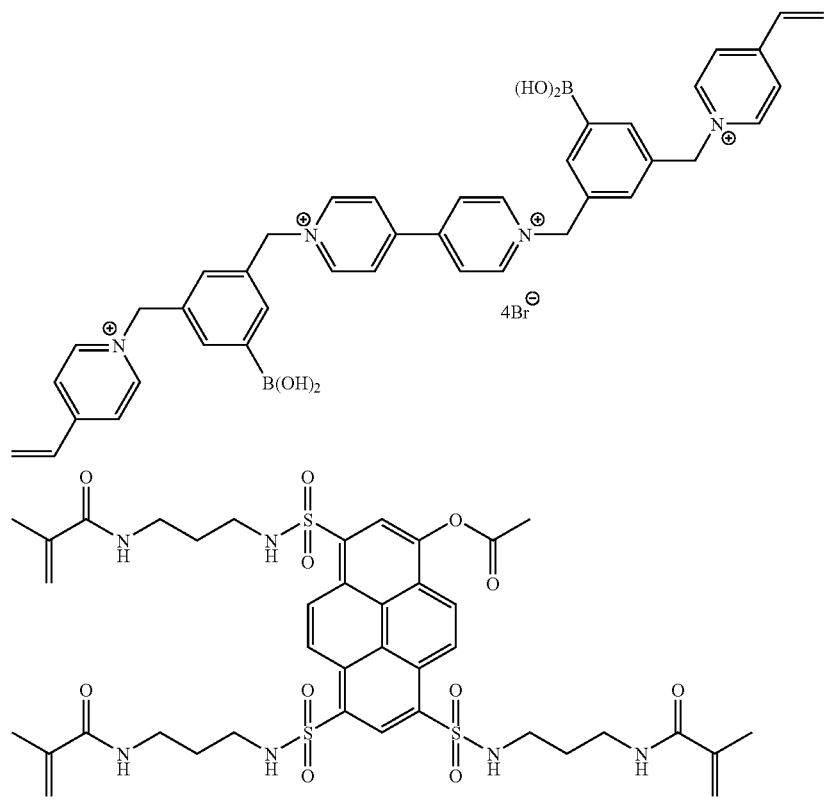

soaked in isopropanol for two hours. The PMMA article is then dried for one hour at 40° C. in a vacuum oven under nitrogen.

EXAMPLE 43

Preparation of Amide Solution

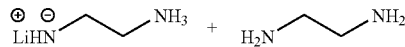

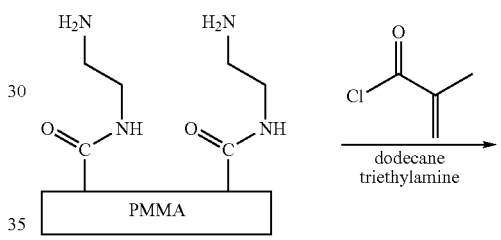

A dry 50 mL round bottom flask is fitted with a magnetic stir bar and rubber septum, cooled under argon, and charged with 1,2-ethanediamine. The flask is then purged with argon for 20 min. Butyllithium ("BuLi 2.0 M in cyclohexane) is added drop wise at room temperature via syringe over 30 minutes. Following the addition of "BuLi, the solution is stirred for 3 hours.

EXAMPLE 44

Amine Functionalization of PMMA Surface

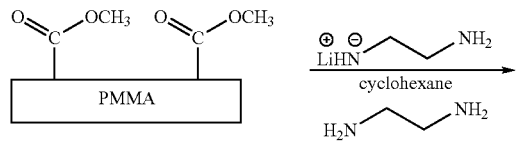

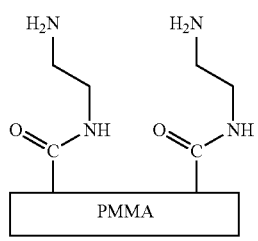

Dry PMMA and the lithium amide solution are transferred to a dry box, which is then flushed with argon. The PMMA surface is then exposed to the lithium amide solution by dripping the amide solution onto PMMA with a Pasteur pipet. The amide solution is left in contact with PMMA for two min and the amide is then quenched with milli-Q water. Amide treated PMMA is then placed into the vacuum oven and dried at 40° C. for one hour.

EXAMPLE 45

Methacrylate Functionalization of PMMA Surface

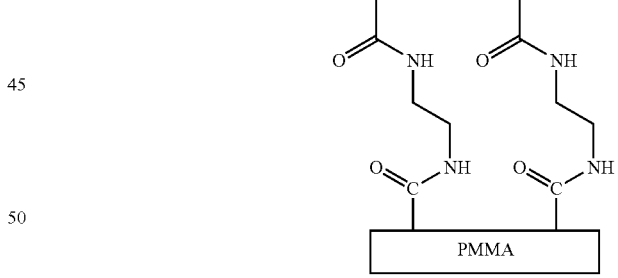

Amine functionalized PMMA is then transferred to the dry box. Dodecane, methacryloylchloride, and triethylamine are placed into dry box, and the dry box is flushed with argon. 5 mL dodecane (25 mmole), 5 mL methacryloylchloride (51 mmole), and 0.5 mL triethylamine (3.5 mmole) are mixed, and this heterogeneous solution is dripped onto the amine functionalized PMMA surface. The solution is left in contact with PMMA for 15 min, then rinsed with isopropanol.

EXAMPLE 46

Covalent Attachment of Sensing Hydrogel Polymer to PMMA Surface

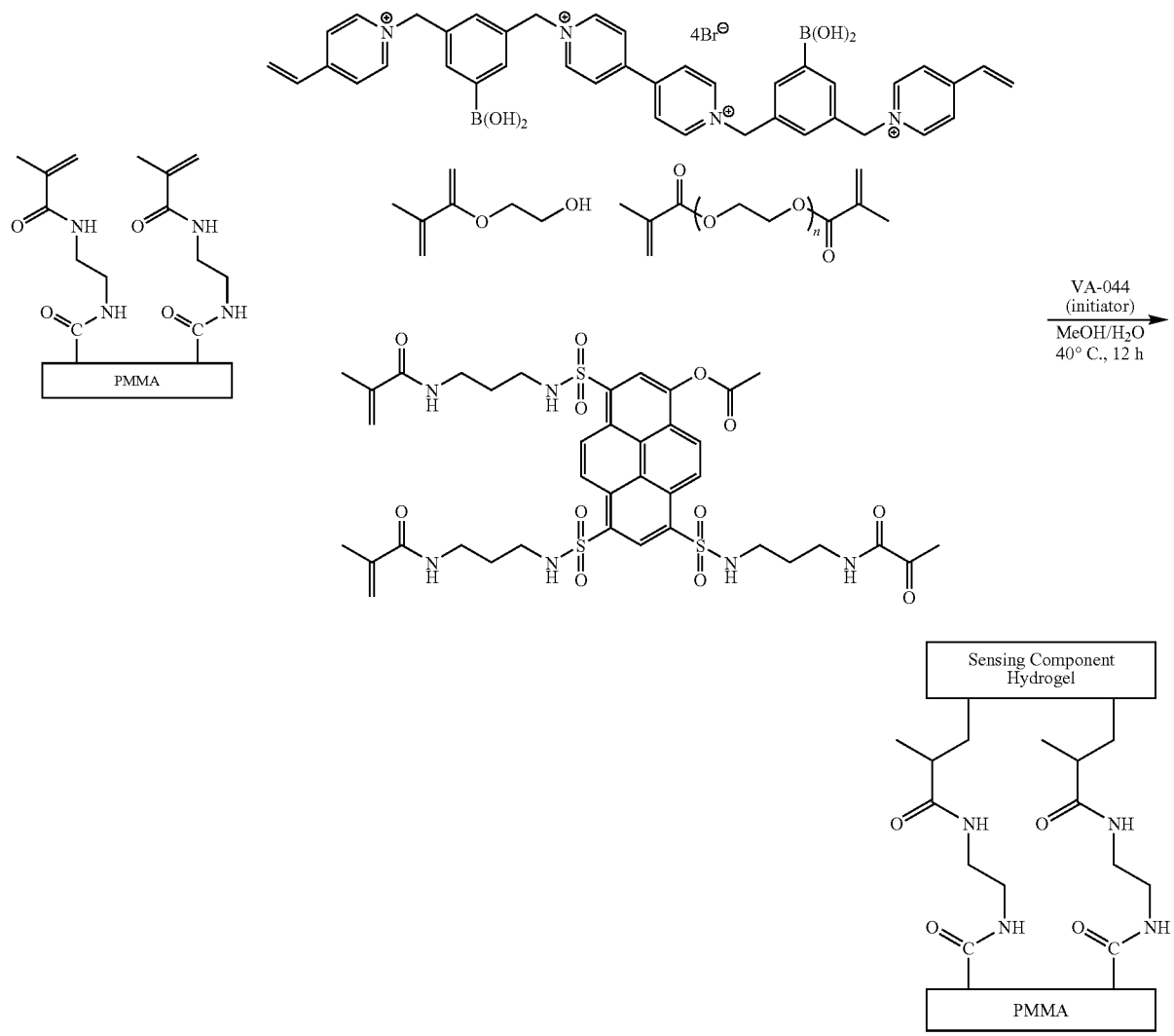

The polymerization chamber is assembled in the usual manner, surface modified PMMA is placed into the chamber as the back plate with the methacrylate functionality on the inside of the polymerization chamber. The top glass plate is treated with dimethylsilane (1% in toluene) and thoroughly rinsed with hexanes before assembling. A monomer mix is then prepared in the usual manner using a 1:20 dye/quencher ratio, the polymerization chamber is filled in the dry box, transferred to the vacuum oven, and maintained at 40° C. for 18 hr. The polymerization chamber is then removed and disassembled. The sandwiched film is placed into a water bath, which is brought to pH 10, and left stirring for 12 hr. The PMMA with covalently attached sensing hydrogel is then placed into pH 7.4 buffer and placed into the refrigerator.

The PMMA bound sensing hydrogel is then cut to fit into the flowthrough cuvette. This film is examined in flowthrough experiments using the Perkin Elmer LS50B spectrophotometer, and also using the Ocean Optics SF2000 spectrophotometer using a glass optical fibers. In both spectrometers, a measurable change in fluorescence is observed with variance in glucose concentration.

EXAMPLE 47

Synthesis of HPTS(LYS-MA)$_3$

A 500 mL round-bottomed flask with magnetic stir bar was charged with 3.0 g of Boc-protected lysine and 10 mL of milliQ water and stirring was commenced. 0.80 G of NaOH were added and allowed to dissolve followed by addition of 85 mL of acetonitrile. 0.600 g of AcOHPTSCl dissolved in 10 mL of tetrahydrofuran were then added dropwise to the stirring solution to produce a red-orange color. The flask was sealed with a septum and allowed to continue overnight. After 22 hr the reaction was stopped and the mixture settled into two phases: a deep red lower aqueous layer and a clear green upper organic layer. The lower aqueous layer was removed with a Pasteur pipet and was added dropwise to a 50 mL centrifuge tube filled with 30 mL of 3M HCl to produce a yellow precipitate. The precipitate was concentrated by centrifugation and the acidic supernatant was decanted. The process was repeated 5 times until all of the red aqueous material had been precipitated. The yield and purity of this crude material were not determined. The combined solids were dissolved in 30 mL of a 50% MeOH/50% pH 7.4 buffer solution.

This material was next separated on a C18 reverse phase Biotage chromatography column having a UV-vis detector in three injections using water/methanol eluent. The combined fractions of interest were evaporated to dryness on the rotary evaporator. This red material was redissolved in 8 mL MeOH and filtered with a 1.0 um syringe filter, dried again on the rotary evaporator and dried completely on the high vacuum overnight. The mass of the dried orange colored material (HPTS(Lys-Box)$_3$ was determined to be 0.815 g. $^1$H NMR analysis reveled that the Boc protecting group remained largely in place.

The product was next redissolved in 20 mL of trifluoroacetic acid and allowed to stir overnight in order to remove the Boc protecting group. After deprotection, the excess acid was neutralized by addition of triethylamine and pH 7.4 buffer solution to give a total volume of 30 mL. A portion of this material was injected on C18 reverse phase Biotage chromatography column using water/methanol eluent. The fractions of interest were combined and dried on rotary evaporator and high vacuum to give 66 mg of highly pure material (HPTS (Lys)$_3$.

This purified dye was placed in a 100 mL round bottomed flask with a magnetic stir bar and dissolved in 1 mL of milliQ water and 0.3 mL of 3M NaOH and the bright green solution was stirred. 10 mL of tetrahydrofuran were added and the flask was sealed with a septum. 0.2 mL of methacryloyl chloride were added via a syringe causing a color change from green to deep red-brown. The reaction was allowed to continue overnight and was stopped after 24 hr. 3M NaOH 1.2 mL were added to bring the pH to 10 in order to form the sodium salt of the product. The stir bar was then removed and the product was dried under vacuum overnight. After additional C18 column chromatography, the final product was isolated as the pink-colored sodium salt. Mass=87 mg. The product was characterized using $^1$H NMR and the spectrum showed clean product with appropriate signals and integration.

EXAMPLE 48

Synthesis of HPTS (LYS-MA)$_3$):BP 0.02" Hydrogel (a) Preparation of Monomer Mixture (1:20 Dye:Quencher Ratio):

A 20 mL scintillation vial was charged with 0.560 g of PEG-DMA, 1.767 g of HEMA, 12 mg of VA-044 (a polymerization initiator), 2 mg of HPTS(Lys-MA)$_3$ dissolved in 1 mL water, and 100 mg of BP (a quencher) dissolved in 1 mL of water. The mixture was placed on a vortex mixer until all the materials had dissolved, then the total volume was brought to 5 mL by addition of milliQ water. The solution was then transferred to a 25 mL round bottom flask that was sealed with a septum before the flask was placed in an ice bath. A syringe needle attached to a nitrogen line was inserted into the flask and the solution was degassed for 15 minutes. 3 mL of the degassed solution was withdrawn using a syringe, corked and placed in the drybox for addition to the polymerization chamber.

(b) Polymerization of the Monomer Mixture:

At the same time, the polymerization chamber was prepared in the conventional manner, degassed, and placed in the drybox. The monomer mixture was added to the polymerization chamber under argon in the drybox. The chamber was sealed and placed in a vacuum oven at 40° C. overnight. After heating for 16 hr, the temperature was raised to 70° C. for one hr, then the chamber was removed from the oven and allowed to cool at ambient. After cooling, the chamber was disassembled and the glass plate to which the then film was attached was placed in a pH 10 water bath. After one day in the water bath, the thin film was cut into cuvette-sized pieces and stored in pH 7.4 buffer and refrigerated.

(c) Performance for the Thin Film:

A single piece of the thin film was mounted inside a flow-through cuvette with lines attached that allow for different solutions to be run through the cuvette while the fluorescence intensity is being measured. After running pH 7.4 buffer over the thin film for several hours a steady baseline was established. The solution was then switched to 90 mg/dL glucose solution in pH 7.4 buffer resulting in an increase of 10% in fluorescence intensity. Changing the solution from 90 mg/dL to a 180 mg/dL glucose solution caused a further 3% increase in fluorescence intensity. A change from 180 mg/dL to a 360 mg/dL caused an additional 2% increase in fluorescence intensity. Finally, when the solution was returned to pH 7.4, the fluorescence intensity dropped by 10%.

EXAMPLE 49

Optical Fiber with Sensing Hydrogel

Assembly of PMMA Optical Fiber

A 1 mm diameter PMMA optical fiber (South Coast Fiber Optics) is assembled by first filling an SMA-905 (Thor Labs part # 11040A) connector with Epotec two part epoxy resin, then pushing the optical fiber through the connector so that about 5 mm of optical fiber protrudes through the back side of the SMA connector. The fiber/connector is then placed into a vacuum oven at 40° C. for 14 hr. A small glass capillary is filled with Epotec two part epoxy resin, and the distal end of the optical fiber is inserted through so that about 5 mm of the optical fiber protrudes through the glass capillary, the fiber is then placed into the vacuum oven at 40° C. for 14 hr. The fiber is removed from the vacuum oven. The proximal end of the fiber is cut with a razor blade almost flush with the SMA connector, polished with 5 micron Aluminum Oxide Fiber polishing film until flush with SMA connector, then polished with 1 micron Aluminum Oxide Fiber polishing film to buff. The distal end is cut with a razor blade almost flush with the glass capillary, polished with 5 micron Aluminum Oxide Fiber polishing film until flush with glass capillary, then polished with 1 micron Aluminum Oxide Fiber polishing film to buff. Both the distal end and the proximal end of the fiber are cleaned with isopropanol, and finally blown clean and dry with canned air.

Hydrogel Preparation

A 0.001 inch sensing hydrogel was prepared as described above mBBVBP/HPTS(lysMA)$_3$ (50:1).

Attachment of Hydrogel to PMMA

A small amount of VetBond™ (3M) was applied to the edges of the distal end of the PMMA optical fiber. The distal end of the PMMA optical fiber was then contacted with the sensing hydrogel piece lying on a metal spatula. After about 60 sec the fiber was lifted off the spatula with the sensing hydrogel affixed. The sensing hydrogel was then trimmed with a razor blade to be approximately the same diameter as the PMMA optical fiber. See FIGS. 15 and 16.

The glass flow through cell was used. The inlet had a small diameter TYGON tubing pushed through a rubber septum wrapped with parafilm. The outlet had a large diameter tygon tubing placed directly over the glass arm. The fiber with sensing hydrogel affixed was pushed through a rubber gasket in a plastic cap, which fit onto the glass flow through cell. The volume of the glass cell and tubing was 120 mL. Aquarium sealant was used to seal up the top where the fiber went through the cap. The solution is circulated using a Masterflex peristaltic pump at a rate of 14 mL/min.

Glucose Response Fluorescent Time Study

Figure 15:
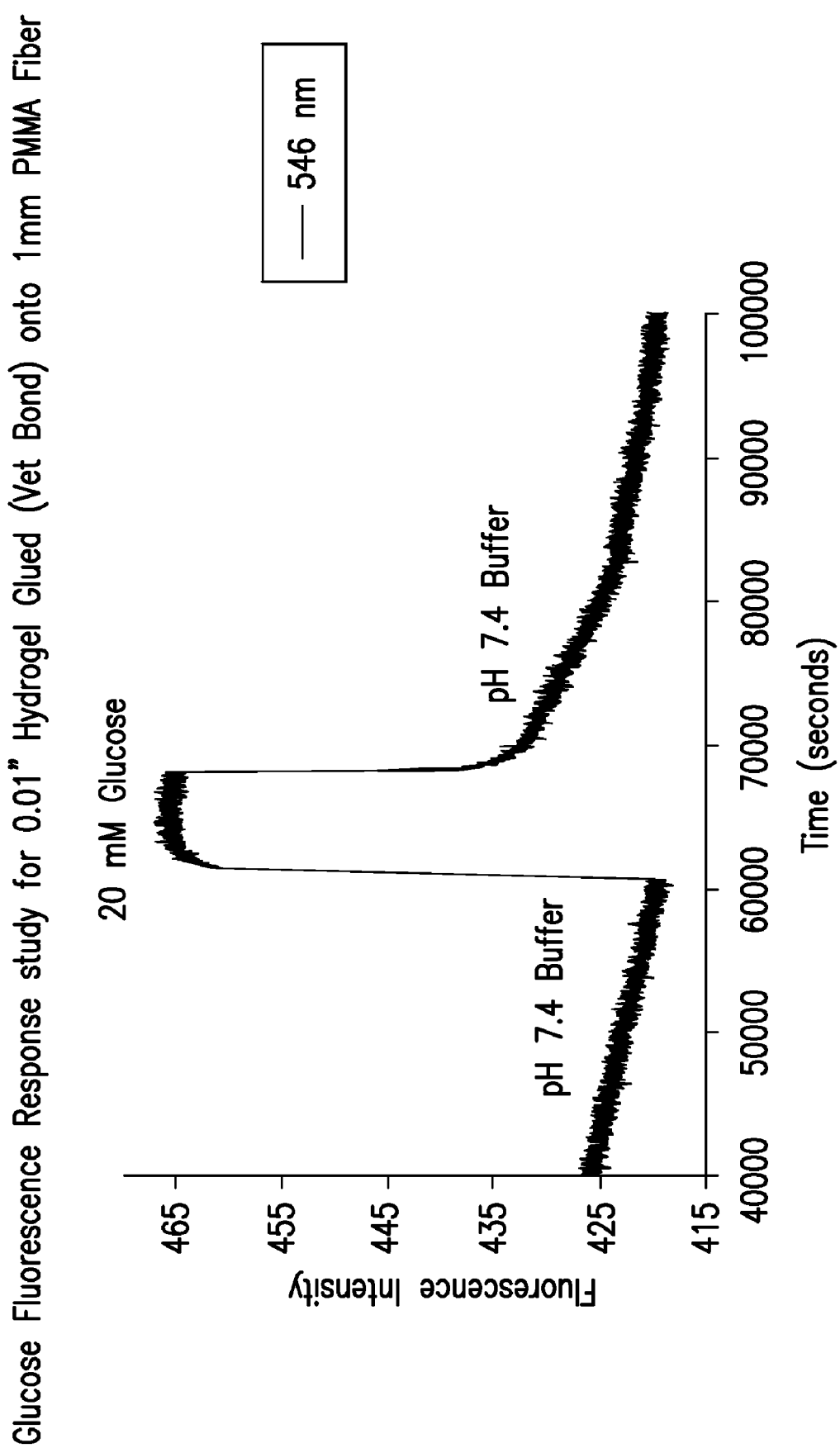
FIG. 15 is a graphic representation of glucose response in fluorescence intensity for hydrogel glued (VetBond) to 1 mm PMMA fiber versus time in seconds.
Figure 16:
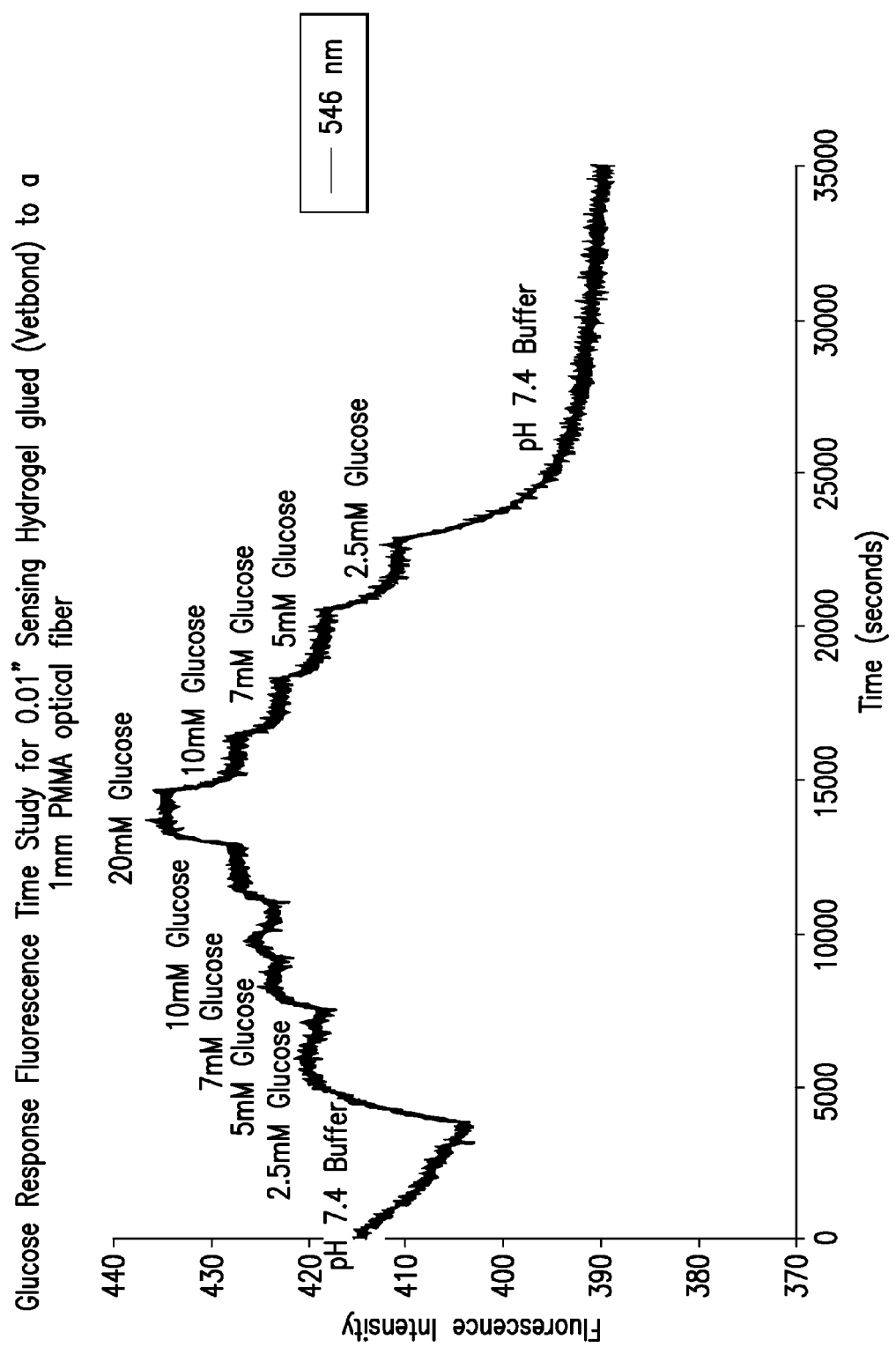
FIG. 16 is similar to FIG. 15 and is the response at different glucose concentrations versus time in seconds.
Figure 17:
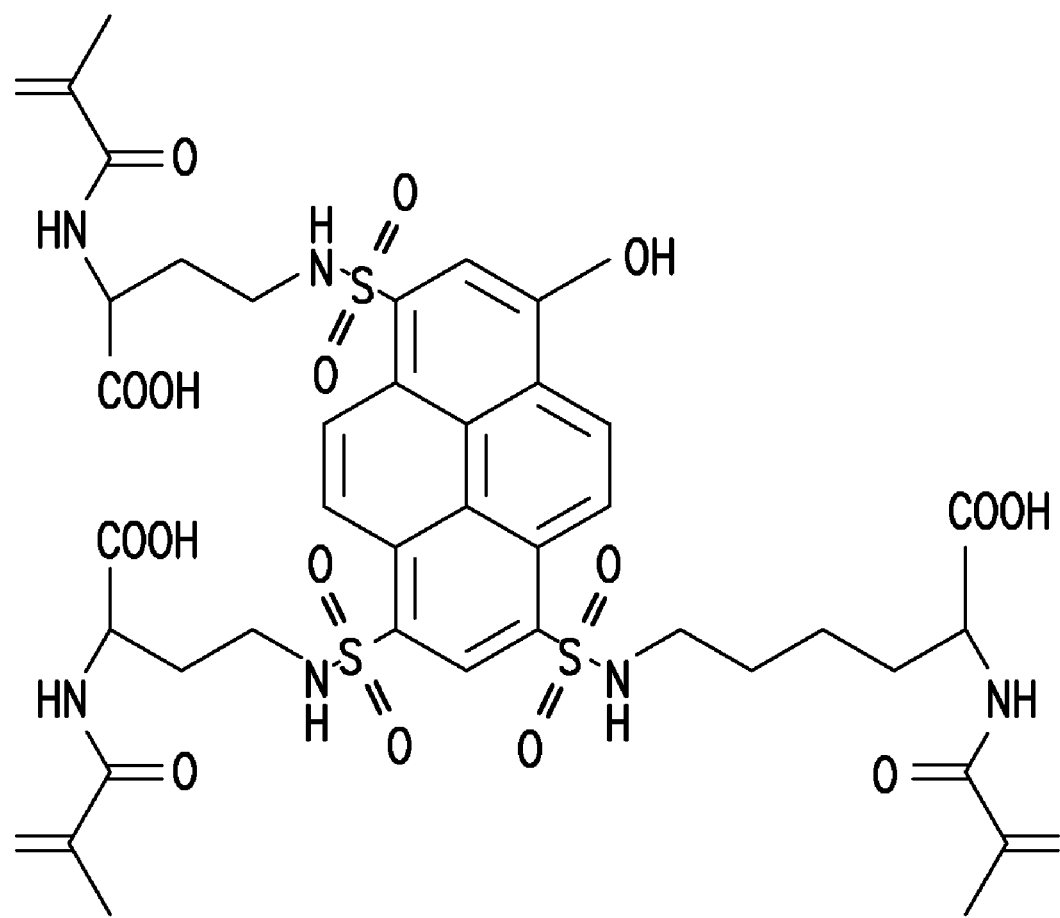
FIG. 17 is the structure of HPTS(Lys-MA)$_3$ as prepared in Example 47.

The excitation source was a blue LED housed in the Ocean Optics SF2000 device. The detector was also house in the Ocean Optics SF2000 device. The ocean optics sf2000 is connected to a lap top computer via the USB 2000. A piece of calamet (unit of .lamda.) filter was placed inside the SMA connector leading into the detector. A glass bifuricated cable is then attached to the Ocean Optics device. The proximal end of the PMMA optical fiber is then attached to the distill end of the glass optical fiber. The ocean optics device is set as follows for emission acquisitions: Integration time=1000 msec.; Average=5; Boxcar=25; Flash Delay=1msec; strobe lamp/enable is checked; correct for electrical dark is checked; emission monitored at 546 nm. First pH 7.4 phosphate buffer is calculated. At 60487 seconds 20 mM glucose (in pH 7.4 phosphate buffer) solution is pumped through (140 mL) then recirculated resulting in an 11% increase in Fluorescence Signal. At 67585 seconds pH 7.4 phosphate buffer is pumped through (140 mL) then recirculated resulting in an 11% decrease in fluorescent signal as shown in FIG. 15. FIG. 16 is similar to FIG. 15 and shows the glucose response for different sample concentrations of glucose versus time in seconds.

EXAMPLE 50

[3,3']Bipydridinyl-5-Carbontrile

To a 50-mL oven-dried round bottomed flask with a side-arm and condenser, was added 5-bromo-3-cyanopyridine (2.2 g, 12 mmol), 3-pyridineboronic acid (1.23 g, 10 mmol), and anhydrous 1A-dioxane (10 mL) under argon. A degassed aqueous solution of $Na_2CO_3$ (2 M, 10 mL) was then added via syringe to the vigorously stirred reaction mixture, followed by the addition of Pd(OAc$_2$ (0.11 g, 0.5 mmol) and PPh$_3$ (0.52 g, 2 mmol). The reaction flask was then degassed using 5 argon/vacuum back-fill cycles, then stirred for 2 h at 95° C. After cooling to ambient temperature, water was added (40 mL), and the reaction was extracted with ethyl acetate (3×100 mL). The combined organics were washed with brine (2×75 mL), dried with magnesium sulfate, and evaporated under reduced pressure. The residue was chromatographed on silica gel (pretreated with 10% triethylamine) using 20% ethyl acetate in dichloromethane to give 0.6 g (34% yield) of white solid. $^1$H NMR (CDCh, 500 MHz). 7.47 (dd, J=8.5, 5.0 Hz, 1H), 7.89 (dt, J=8.5, 2.0 Hz, 1H), 8.15 (t, J=2.5 Hz, 1H), 8.72 (dd, J=5.0, 1.5 Hz, 1H), 8.85 (d, J=2.0 Hz, 1H), 8.91 (d, J=2.0 Hz, 1H), 9.03 (d, J=2.5 Hz, 1H); $^{13}$C NMR (CDCl$_3$, 125 MHz) 110.42, 116.20, 124.7, 131.33, 133.95, 134.54, 137.37, 148.09, 150.46, 151.36, 151.53; MS (ES!) mJz calcd for $C_{11}H_8N_3$ (M+H)$^+$: 182.06. found 182.1.

EXAMPLE 51

C-[3,3']Bipydridinyl-5-Yl-Methylamine

To a solution of $CoCl_2$ (0.86 g, 6.6 mml) in methanol (20 mL), was added $NaBH_4$ (1.25 g, 33 mmol) portionwize, resulting in an exothermic reaction with Hz evolution. The reaction was stirred for 10 min., and the black precipitate that formed was filtered, washed with methanol and air-dried. The black solid was added to a suspension of [3,3']bipyridinyl-5carbonitrile (0.6 g, 3.3 mmol) in methanol (40 mL). After cooling to 0° C., $NaBH_4$ (1 g) was added, and the reaction was stirred at ambient temperature for 12 h. Then, 3 M HCl (200 mL) was added, the methanol was removed under reduced pressure, and the acidic aqueous layer was washed with ether (100 mL), then basified with conc. NaOH, extracted with ethyl acetate, dried with $Na_2SO_4$, and evaporated to a yellow oil (0.15 g).

EXAMPLE 52

N-[3,3']Bipyridinyl-5-Ylmethyl-2Methyl-Acrylamide

To a cooled solution of C-[3,3']Bipyridinyl-5-yl-methylamine (1.16 g, 6.2 mmol) in dichloromethane (100 mL) was added methacryloyl chloride dropwise. After stirring for 7 h at ambient temperature, the reaction was quenched with 1 M NaOH, and extracted with dichloromethane (2×100 mL). The combined organics were washed with sat. NaHCO$_3$, brine, dried with Na$_2$SO$_4$, and evaporated to a yellow oil (1.65 g) which was chromatographed en silica gel (pretreated with 10% triethylamine) using a methanol gradient (0-3%) in dichloromethane to give 0.76 g of clear oil.

EXAMPLE 53

Synthesis of P3,3'-OBBV

To a solution of N-[3,3']-Bipyridinyl-5-ylmethyl-2methyl-acrylamide (0.15 g, 0.59) in DMF (25 mL), was added o-bromomethylphenylboronic acid (0.29 g, 1.36 mml), and the reaction was stirred at 55° C. for 48 h. After cooling to ambient temperature, acetone (100 mL) was added to the yellow solution to induce precipitation. The white precipitate was collected by centrifugation, washed with acetone, and dried under a stream of argon to yield 0.1 g (25% yield) of product.

EXAMPLE 54

Hydrogel Containing P3,3'-OBBV and APTS-LYS-E-MA

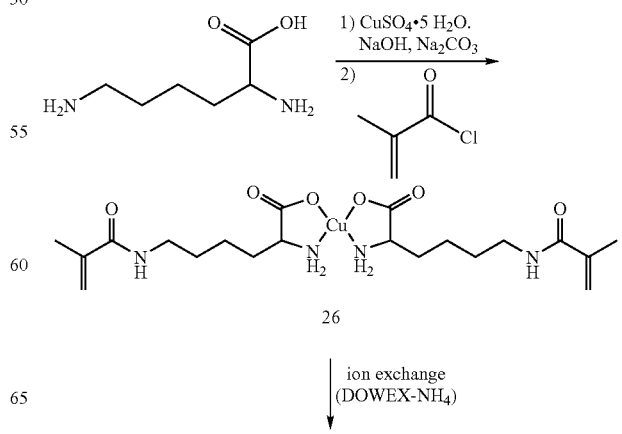

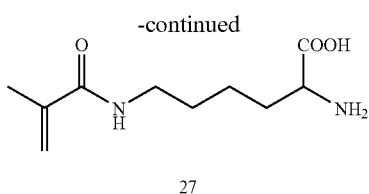

27

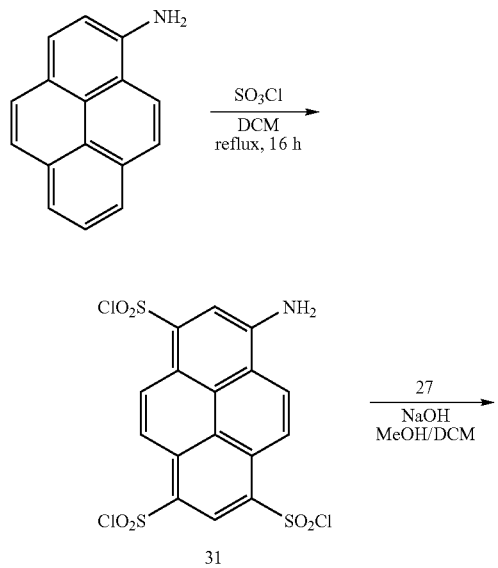

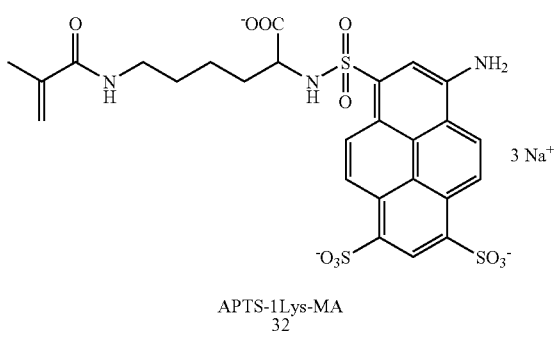

APTS-1Lys-MA
32

$N^\epsilon$-Methacryloyl-(S)-lysine (27). Methacryloyl chloride (4.8 mL, 50 mmol) was slowly added, via syringe, to a cooled (0° C.) solution of lysine monohydrochloride (8.0 g, 43.6 mmol), $CuSO_4 \cdot 5H_2O$ (5.46 g, 21.8 mmol), NaOH (3.6 g, 90 mmol), and $Na_2CO_3$ (4.6 g, 43.6 mmol) in $H_2O$ (80 mL). The reaction was stirred at RT for 2 h. The resulting blue precipitate was filtered and washed with $H_2O$, acetone, ether, then $H_2O$ again. After air-drying, the violet-blue solid (26) was purified by ion exchange: ca. 40 mL of DOWEX® 50WX8-400 resin was treated with 1 M $NH_4OH$ (100 mL), and the suspension was poured into a column and washed with conc. $NH_4OH$. The copper complex (26) was dissolved in conc. $NH_4OH$ (2 mL), loaded onto the column, and eluted with ca. 500 mL of conc. $NH_4OH$. The solution was evaporated in vacuo, and dried under high vac. to yield pure 27 as a white solid (5.5 g, 60%). $^1H$ NMR (250 MHz, $D_2O$) δ: 1.53 (m, 2H), 1.67 (m, 2H), 1.98 (m, 2H), 2.02 (s, 3H), 3.37 (t, J=6.5, 2H), 3.83, (t, J=6.0, 1H), 5.53, (s, 1H), 5.77 (s, 1H); $^{13}C$ NMR (69.3 MHz, $D_2O$) δ: 17.75, 21.85, 28.12, 30.14, 39.14, 54.71, 120.82, 139.22, 171.93, 174.79. See *Makromol. Chem.* 1980, 181, 2183-2197.

APTS-Cl (31). A dry 50-mL round-bottom flask with a side-arm and condenser, was charged with 1-aminopyrene (0.50 g, 2.3 mmol) and $CH_2Cl_2$ (10 mL) under argon. To this clear brown solution was added chlorosulfonic acid (2 mL, 30 mmol) dropwise, via syringe, and the reaction was refluxed for 16 h. After cooling to RT, the reaction mixture was poured into a beaker of crushed ice. The red-colored water (containing some solid) was extracted with $CH_2Cl_2$ several times. All $CH_2Cl_2$ portions (amber-colored) were combined, dried with $Na_2SO_4$, filtered and evaporated to give 31 as a dark red solid (0.47 g, 40%). $^1H$ NMR (250 MHz, $CDCl_3$) δ: 8.35 (s, 1H), 8.59 (d, J=9.5, 1H), 9.14 (d, J=9.75, 1H), 9.23 (d, J=9.5, 1H), 9.48 (d, J=9.75, 1H), 9.49, (s, 1H).

APTS-Lys-e-MA (32). To a solution of 31 (0.47 g, 0.92 mmol) in $CH_2Cl_2$ (100 mL) was added a solution of $N^\epsilon$-Methacryloyl-(S)-lysine (0.63 g, 2.9 mmol) and NaOH (0.23 g, 5.5 mmol) in $CH_3OH$ (20 mL). The clear, amber-colored solution became greenish, and orange precipitate formed when the basic lysine was added. The heterogeneous reaction mixture was stirred for 16 h, then filtered and washed several times with $CH_2Cl_2$. After drying under reduced pressure, 32 was obtained as an orange solid (0.63 g, 95%).

Observations with P3,3'-oBBV

A solution of P3,3-oBBV in water remained colorless when exposed to UV light (254 nm or 365 nm) for extended periods of time (several hours). A 4,4'-oBBV derivative, however, was observed to turn pink colored under these same conditions.

A hydrogel composed of P3,3-oBBV and a polymerizable dye (SG5-34, Feb. 27, 2005) did not change color when exposed to the same aforementioned conditions. It also did not change colors when exposed to continuous illumination at 467 nm (argon laser).

EXAMPLE 55

Synthesis of APTS-BUMA

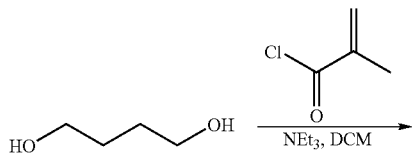

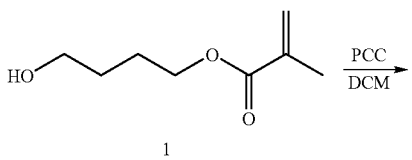

1

-continued

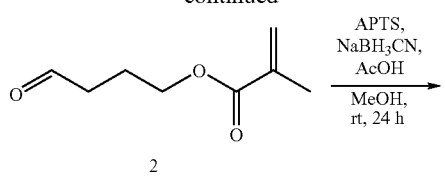

2

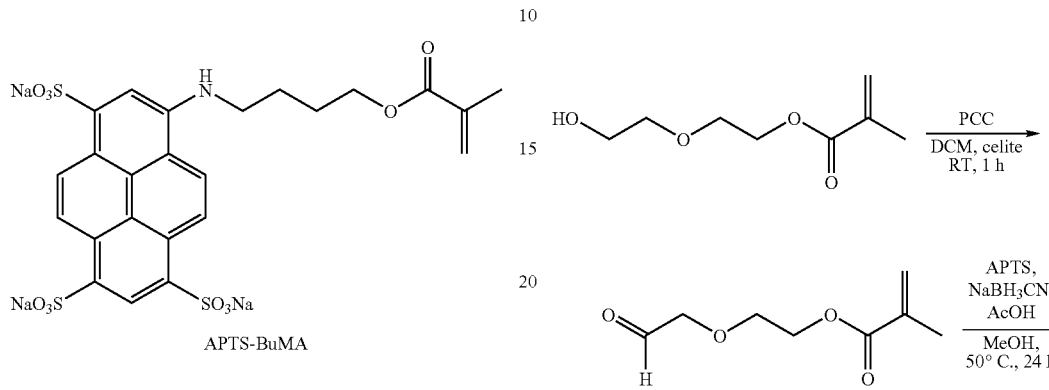

APTS-BuMA

A. Synthesis of Compound 1

Methacryloyl chloride (5.86 mL, 60 mmol) was added dropwise to a cooled solution (0° C.) of 1,4-butanediol (5.33 mL, 60 mmol) and pyridine (30 mL) in dichloromethane (30 mL). The reaction was stirred at room temperature for 2 h., quenched with 1M HCl (50 mL), and extracted with dichloromethane (3×100 mL). The combine DCM layers were washed with 3M HCl (DCM-3×100 mL), dried with magnesium sulfate, and evaporated to a pink oil which was chromatographed on silica gel using hexanes/ethylacetate (6:4) to give 3.7 g (40% yield) of clear oil.

B. Synthesis of Compound 2

A solution of Compound 1 (3.7 g, 23 mmol) in dichloromethane (10 mL) was added to a suspension of pyridinium chlorochromate (7.4 g, 34.5 mmol) and celite (5 g) in dichloromethane (30 mL). The reaction was stirred at room temperature for 4 h. Diethylether (200 mL) was added and the reaction was filtered through celite. The dark brown filtrate was evaporated to a black oil which was then chromatographed on silica gel using 100% dichloromethane to yield 2 g (56% yield) of clear oil.

C. Synthesis of APTS-BuMA

To a solution of 8-aminopyrenetrisulfonic acid trisodium salt (APTS) (0.6 g, 1.15 mmol) in dry methanol (20 mL) was added Compound 2 (0.18 g, 1.15 mmol) and glacial acetic acid (1 mL, 17 mmol). A solution of sodium cyanoborohydride (0.3 g, 4.7 mmol) in dry methanol (10 mL) was then added, and the reaction was allowed to stir at ambient temperature overnight. The starting material and product (.apprxeq. 50:50) were observed by TLC, so the reaction was heated at 55° C. for 4 h. The reaction mixture was evaporated, and the resulting residue was redissolved in a minimal amount of water and purified by flash column chromatography on silica gel (isopropanol/ammonium hydroxide 9:1 to 3:1 gradient). Isolated 0.15 g (20% yield) of orange powder. Reference for various APTS derivatives include PCT Int. Pub. No. WO2004/027388.

EXAMPLE 56

Synthesis of APTS-DEGMA

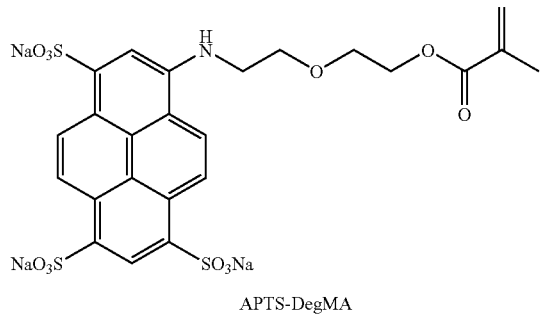

3

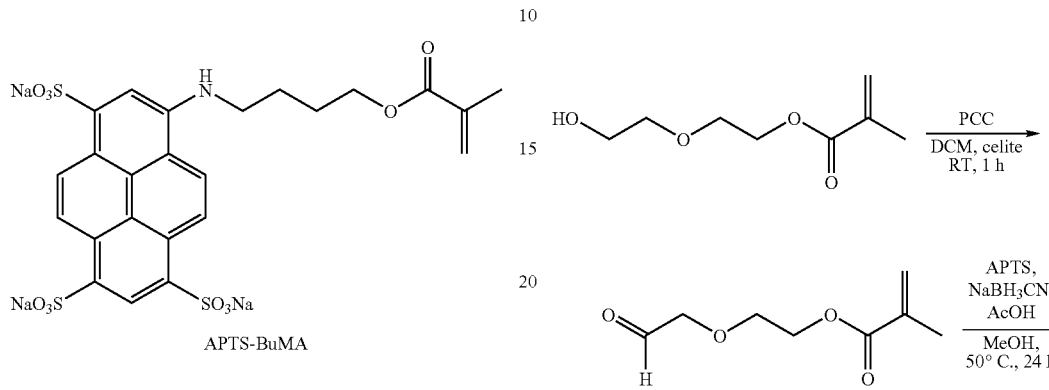

APTS-DegMA

A. Synthesis of Compound 3

A solution of diethylene glycol monomethacrylate (4 g, 23 mmol) in dichloromethane (10 mL) was added to a suspension of pyridinium chlorochromate (7.4 g, 34.5 mmol) and celite (8 g) in dichloromethane (40 mL). The reaction was stirred at ambient temperature for 1 h. Diethylether (200 mL) was added and the reaction was filtered through celite. The dark brown filtrate was evaporated to a black oil, which was then chromatographed on silica gel using 0% to 5% ethyl acetate in dichloromethane to yield 1.4 g (36% yield) of light green oil.

B. Synthesis of APTS-DegMA

To a solution of 8-aminopyrenetrisulfonic acid trisodium salt (APTS) (0.23 g, 0.44 mmol) in dry methanol (10 mL) was added Compound 3 (0.3 g, 1.77 mmol) and glacial acetic acid (0.4 mL, 6.6 mmol). A solution of sodium cyanoborohydride (0.12 g, 1.77 mmol) in dry methanol (10 mL) was then added, and the reaction was let stir at 50° C. for 2 h. The reaction mixture was evaporated, and the resulting residue was redissolved in a minimal amount of methanol and purified by flash column chromatography on silica gel (isopropanol/ammonium hydroxide 7:1 to 4:1 gradient). Isolated 0.145 g (48% yield) of orange powder.

EXAMPLE 57

Synthesis of 1MA-BP A

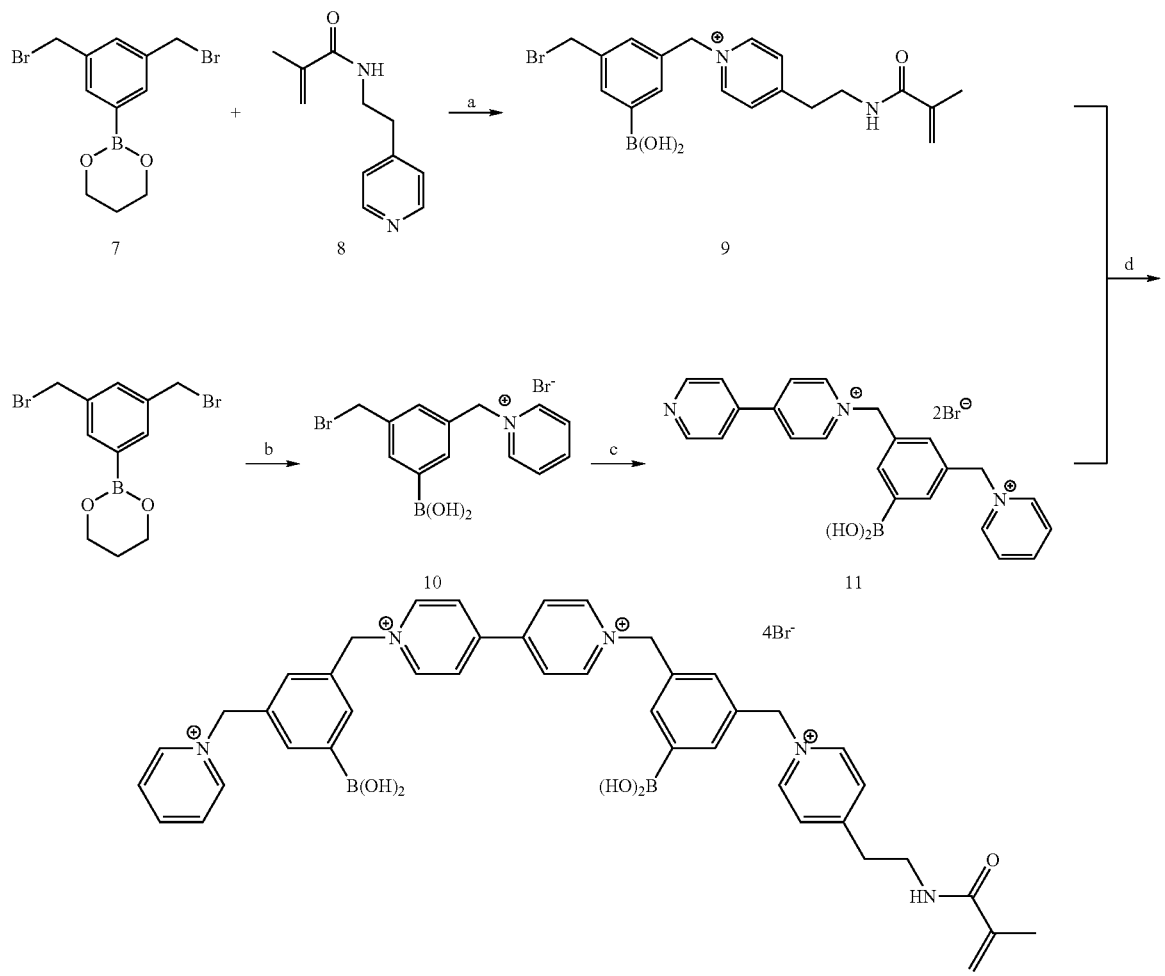

1MABP a) CH₂Cl₂/CH₃OH (3:1), 40° C., 22 h, 48% (9), 52% (11); b) 4,4'-dipyridyl, DMF, 60° C., 48 h, 58%; c) 1. 4,4'-dipyridyl, DMF, 80° C., 5 min; 2. acetone, 74%; d) DMF, 60° C., 48 h, 56%.

Synthesis of Compound 7

To a 500 mL round-bottom flask fitted with a condenser and a sidearm was added 3,5-dimethylphenylboronic acid (10.5 g, 70 mmol), calcium hydride (5.9 g, 140 mmol), and dichloroethane (300 mL). After 10 minutes of stirring under argon, 1,3-propanediol (5.6 mL, 77 mmol) was added via syringe. The reaction was refluxed for 1.5 h, cooled to ambient temperature, and filtered. The clear filtrate was mixed with N-bromosuccinimide (27.4 g, 154 mmol) and 2,2'-azobisisobutryonitrile (2.3 g, 14 mmol) and refluxed for 3 h. The orange solution was cooled overnight (.apprxeq. 16 h), and the succinate crystals that formed were filtered off. The filtrate was evaporated to dryness, leaving an off-white chunky solid, which was recrystallized from methanol (ca. 300 mL) to give 11.0 g (46%) of pure Compound 7: $^1$H NMR (CDCl$_3$, 500 MHz) δ 2.07 (q, J=5.5 Hz, 2H), 4.17 (t, J=5.5 Hz, 4H), 4.49 (s, 4H), 7.48 (s, 1H), 7.74 (s, 2H); $^{13}$C NMR (CDCl$_3$, 125 MHz) δ 27.51, 33.39, 62.22, 131.92, 134.52, 137.73; $^{11}$B NMR (80 MHz, CDCl$_3$) δ 28.5. Anal. Calcd for C$_{11}$H$_{13}$BBrO$_2$: C, 37.98; H, 3.77; Br, 45.94. Found: C, 38.08; H, 3.68; Br, 46.12.

B. Synthesis of Compound 8

Methacryloyl chloride (6.7 mL, 69.6 mmol) was added dropwise to a cooled (−10° C.) solution of 4-(2-aminoethyl)pyridine (7.0 mL, 58 mmol) in CH$_2$Cl$_2$ (200 mL), and the reaction was stirred at ambient temperature for 16 h. Saturated Na$_2$CO$_3$ (200 mL) was added, and the organic layer was separated. The aqueous layer was extracted with CH$_2$Cl$_2$ (100 mL), and the organic layers were combined, washed with 1M NaOH (2×100 mL), dried with Na$_2$SO$_4$, filtered, and evaporated to give the product as an orange oil (7.0 g, 63% yield). Purification by flash column chromatography using EtOAc/Hexanes (9:1) gave a clear oil.

$^1$H NMR (CDCl$_3$, 500 MHz) δ 1.54 (s, 3H), 2.49 (t, J=7.0 Hz, 2H), 3.17 (q, J=6.5 Hz, 2H), 4.90 (s, 1H), 5.32 (s, 1H), 6.74 (d, J=5.5 Hz, 2H), 7.57 (t, J=5.5, NH), 7.98 (d, J=4.5 Hz, 2H); $^{13}$C NMR (CDCl$_3$, 125 MHz) δ 18.5, 34.7, 39.8, 119.2, 124.2, 139.9, 148.5, 149.2, 168.9.

C. Synthesis of Compound 9

Compound 8 (1.3 g, 6.8 mmol) was added to a solution of Compound 7 (9.5 g, 27.3 mmol) in $CH_2Cl_2$ (370 mL) and $CH_3OH$ (180 mL), and the reaction was stirred at 40° C. for 20 h. The $CH_2Cl_2$ was removed in vacuo, and the excess Compound 7 which precipitated out of methanol was filtered off and washed with ice-cold methanol. The filtrate was concentrated down to ca. 20 mL, then acetone (ca. 300 mL) was added, followed by the addition of ether until turbidity occurred. Storage at −4° C. for 24 h resulted in the formation of a white precipitate which was collected by centrifugation, washed several times with acetone, and dried under argon to yield 0.91 g of pure Compound 9 (33% yield). $^1$H NMR ($CD_3OD$, 500 MHz) δ 1.83 (s, 3H), 3.16 (t, J=6.5 Hz, 2H), 3.61 (t, J=6.5 Hz, 2H), 4.57 (s, 2H), 5.32 (s, 1H), 5.59 (s, 1H), 5.79 (s, 2H), 7.50-7.79 (m, 3H), 7.98 (d, J=6.5 Hz, 2H), 8.92 (d, J=6.5 Hz, 2H); $^{13}$C NMR ($CD_3OD$, 125 MHz) δ 17.3, 31.8, 35.2, 38.6, 119.4, 128.6, 130.7, 133.1, 133.6, 135.5, 139.0, 139.5, 143.6, 143.8, 169.8; $^{11}$B NMR (80 MHz, $CD_3OD$) δ 28.1.

D. Synthesis of Compound 10

Pyridine (0.56 mL, 7 mmol) was added via syringe to a solution of Compound 7 (9.73 g, 28 mmol) in $CH_2C_2$ (370 mL) and $CH_3OH$ (180 mL), and the reaction was stirred at 40° C. for 22 h. The $CH_2Cl_2$ was removed in vacuo, and the excess Compound 7 which precipitated out of methanol was filtered off and washed with ice-cold methanol. The filtrate was concentrated down to ca. 20 mL, and then acetone (ca. 300 mL) was added, followed by the addition of ether until turbidity occurred. Storage at −4° C. for 24 h resulted in the formation of white needle-shaped crystals. The solid was collected by centrifugation, washed several times with acetone, and dried under argon to yield 1.3 g of pure Compound 10 (48% yield): $^1$H NMR ($CD_3OD$, 500 MHz) δ 4.57 (s, 2H), 5.88 (s, 2H), 7.64 (s, 1H), 7.75-7.90 (m, 2H), 8.13 (dd, J=7.0, 7.5 Hz, 2H), 8.61 (tt, J=8.0, 1.5 Hz, 1H), 9.10 (d, J=5.5 Hz, 2H); $^{13}$C NMR ($CD_3OD$, 125 MHz) δ 31.9, 64.1, 128.4, 130.9, 133.0, 133.8, 135.6, 139.1, 144.6, 146.1; $^{11}$B NMR (80 MHz, $CD_3OD$) δ 28.3.

E. Synthesis of Compound 11

To a solution of Compound 10 (0.4 g, 1.03 mmol) in DMF (20 mL), was added 4,4'-dipyridyl (0.8 g, 5.2 mmol), and the reaction was heated in an oil bath. Once the temperature reached 80° C. (ca. 5 min), a small amount of yellow precipitate began to form. The reaction was filtered hot, and acetone (ca. 50 mL) was added to the clear yellow filtrate until a fluffy white precipitate formed. The precipitate was collected by centrifugation, washed with acetone several times, and dried under a stream of argon to yield pure Compound 11 as an off-white solid (0.41 g, 74% yield): $^1$H NMR ($CD_3OD$, 500 MHz) δ 5.94 (s, 2H), 5.98 (s, 2H), 7.89 (br s, 1H), 7.93 (br s, 1H), 7.96 (br s, 1H) 7.99 (dd, J=4.5, 1.5 Hz, 2H), 8.14 (t, J=7.0 Hz, 2H), 8.54 (d, J=7.0 Hz, 2H), 8.61 (tt, J=7.5, 1.5 Hz, 1H), 8.80 (dd, J=5.0, 1.5 Hz, 2H), 9.17 (d, J=6.0 Hz, 2H), 9.25 (d, J=7.0 Hz, 2H); $^{13}$C NMR ($CD_3OD$, 125 MHz) δ 63.4, 63.7, 122.2, 126.1, 128.4, 133.7, 133.8, 135.2, 135.3, 142.1, 144.7, 145.3, 146.0, 149.5, 150.3, 154.0; $^{11}$B NMR (80 MHz, $CD_3OD$) δ 27.1.

F. Synthesis of 1MA-BP

Compound 11 (0.88 g, 1.6 mmol) was sonicated in DMF (100 mL), and the insolubles were filtered off. Compound 9 (0.8 g, 2.0 mmol) was added to the clear yellow filtrate, and the reaction was stirred at 70° C. for 72 h. The resulting dark orange precipitate was collected by centrifugation, washed with DMF, then acetone, and dried under a stream of argon to yield pure 1MA-BP (0.65 g, 44% yield).). $^1$H NMR ($CD_3OD$, 500 MHz) δ 1.83 (s, 6H), 3.16 (t, J=6.5 Hz, 2H), 3.61 (t, J=6.5 Hz, 2H), 5.31 (s, 1H), 5.60 (s, 1H), 5.85 (s, 2H), 5.92 (s, 2H), 6.01 (s, 4H), 7.84 (br s, 6H), 7.99 (d, J=6.5 Hz, 2H), 8.13 (t, J=7.25 Hz, 2H), 8.60 (t, J=7.75 Hz, 1H), 8.69 (d, J=6.5 Hz, 4H), 8.99 (d, J=6.5 Hz, 2H), 9.16 (d, J=5.5 Hz, 2H), 9.37 (d, J=6.5 Hz, 4H); $^{13}$C NMR ($D_2O$, 125 MHz) δ 18.98, 36.39, 40.06, 64.79, 65.45, 65.7, 122.3, 123.9, 127.7, 128.7, 129.9, 130.2, 132.5, 134.2, 135.1, 136.6, 140.1, 144.9, 145.7, 146.9, 147.5, 151.7, 172.9; $^{11}$B NMR (80 MHz, $D_2O$) δ 23.9.

EXAMPLE 58

Synthesis of P2-3,3-OBBV

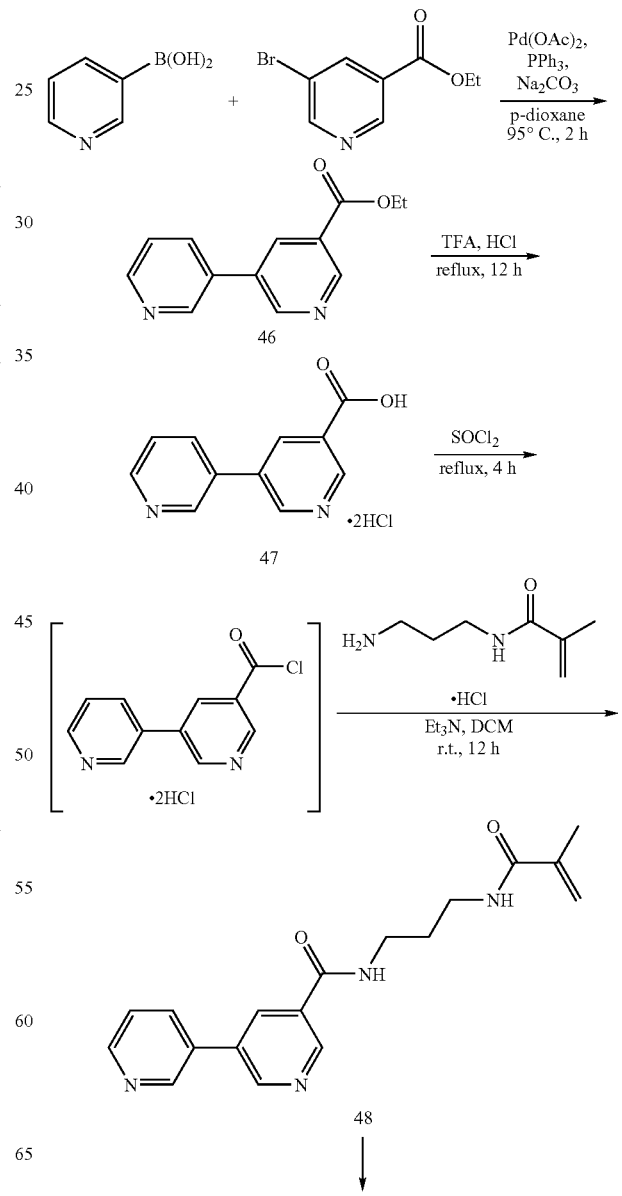

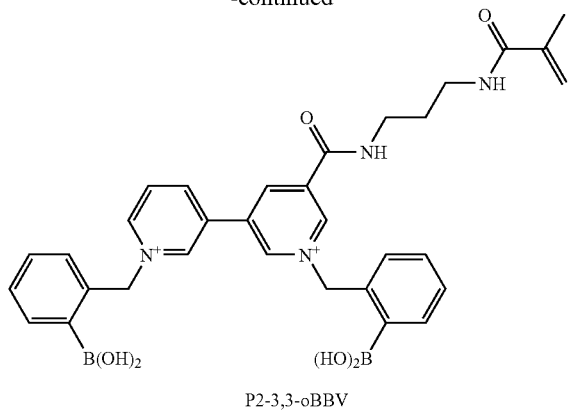

P2-3,3-oBBV

A. [3,3'] Bipyridinyl-5-carboxylic Acid Ethyl Ester Compound (46)

To a 50 mL oven-dried round-bottomed flask with a side-arm and condenser, was added ethyl-5-bromonicotinate (2.76 g, 12 mmol), 3-pyridineboronic acid (1.23 g, 10 mmol), and anhydrous 1,4-dioxane (25 mL) under argon. A degassed aqueous solution of $Na_2CO_3$ (2 M, 10 mL) was then added via syringe to the vigorously stirred reaction mixture, followed by the addition of $Pd(OAc)_2$ (0.11 g, 0.5 mmol) and $PPh_3$ (0.65 g, 2.5 mmol). The reaction flask was then degassed using 5 argon/vacuum back-fill cycles, then stirred for 3 h at 95° C. After cooling to ambient temperature, water was added (50 mL), and the reaction was extracted with ethyl acetate (3×100 mL). The combined organics were washed with brine (2×100 mL), dried with $Na_2SO_4$, and evaporated under reduced pressure. The residue was chromatographed on silica gel (pretreated with 10% triethylamine) using 10% ethyl acetate in dichloromethane to give 1.0 g (44% yield) of white solid. $^1$H NMR ($CDCl_3$, 250 MHz) δ 1.39 (t, J=7.0 Hz, 3H), 4.41 (q, J=7.25 Hz, 2H), 7.40 (dd, J=8.0, 4.75 Hz, 1H), 7.88 (dt, J=7.75, 1.5 Hz, 1H), 8.44 (t, J=2.0 Hz, 1H), 8.64 (dd, J=4.75, 1.5 Hz, 1H), 8.84 (d, J=2.25 Hz, 1H), 8.95 (d, J=2.5 Hz, 1H), 9.20 (d, J=1.75 Hz, 1H); $^{13}$C NMR ($CDCl_3$, 125 MHz) δ 14.20, 61.63, 123.77, 126.41, 131.88, 133.23, 134.42, 135.19, 148.09, 149.69, 150.07, 151.42, 164.85.

B. [3,3'] Bipyridinyl-5-carboxylic Acid Compound (47)

The dipyridyl ethyl ester compound (46) (0.75 g, 3.3 mmol) was dissolved in a mixture of trifluoroacetic acid (5 mL) and HCl (7.5 M, 5 mL), and refluxed for 16 h. The reaction was evaporated to a yellow solid, then sonicated in acetone and filtered to give the HCl salt of the title compound as a white solid 0.84 g (94% yield). $^1$H NMR (DMSO-$d_6$, 250 MHz) δ 8.19 (dd, J=8.0, 6.0 Hz, 1H), 8.83 (t, J=2.0 Hz, 1H), 8.99 (d, J=5.75 Hz, 1H), 9.05 (d, J=8.5 Hz, 1H), 9.20 (d, J=1.75 Hz, 1H), 9.36 (d, J=2.0 Hz, 1H), 9.46 (d, J=1.0 Hz, 1H); $^{13}$C NMR (DMSO-$d_6$, 62.5 MHz) δ 127.25, 127.40, 130.45, 134.80, 137.06, 140.80, 141.42, 143.93, 149.56, 150.73, 165.39.

C. 3,3'-Dipyridyl Diamide Compound (48)

The dipyridyl carboxylic acid compound (47) (0.83 g, 3 mmol) was suspended in thionyl chloride (20 mL) and refluxed for 4 h. The reaction mixture was evaporated to dryness, resuspended in dichloromethane (20 mL), and cooled to 0° C. A solution of N-(3-aminopropyl)methacrylamide hydrochloride (0.54 g, 3 mmol) and triethylamine (3 mL, 30 mmol) in DCM (20 mL) was then added dropwise. After stirring at ambient temperature for 16 h, KOH (3 M, 10 mL) was added. The mixture was diluted with more DCM and water, and the aqueous layer was extracted with DCM (2×100 mL). The combined organics were washed with brine (2×100 mL), dried with $Na_2SO_4$, and evaporated to a yellow oil which was then chromatographed on silica gel (pretreated with 10% triethylamine) using a 0-4% methanol gradient in dichloromethane to give 0.56 g (58% yield) of a white foam. $^1$H NMR ($CDCl_3$, 500 MHz) δ 1.79 (p, J=5.5 Hz, 2H), 1.97 (s, 3H), 3.43 (q, J=6.0 Hz, 2H), 3.51 (q, J=6.0 Hz, 2H), 5.35 (s, 1H), 5.77 (s, 1H), 6.78 (br s, NH), 7.41 (dd, J=7.5, 5.0 Hz, 1H), 7.95 (d, J=7.5 Hz, 1H), 8.26 (br s, NH), 8.46 (s, 1H), 8.64 (d, J=4.0 Hz, 1H), 8.88 (s, 1H), 8.91 (s, 1H), 9.14 (s, 1H); $^{13}$C NMR ($CDCl_3$, 125 MHz) δ 18.73, 29.67, 36.36, 36.40, 120.40, 123.99, 130.43, 132.86, 133.37, 133.67, 134.71, 139.62, 147.93, 148.19, 149.67, 150.22, 165.60, 169.64.

D. P2-3,3'-oBBV

To a solution of compound (2.0 g, 6 mmols) 48 in DMF (25 mL), was added o-monomethylphenylboronic acid (0.29 g, 1.36 mmol), and the reaction was stirred at 55° C. for 72 h. After cooling to ambient temperature, acetone (500 mL) was added to the yellow solution to induce precipitation. The white precipitate was collected by centrifugation, washed with acetone, and dried under a stream of argon to yield 3 g (67% yield) of product.

EXAMPLE 59

Hydrogel Synthesis and Glucose Response

A. Hydrogel Containing 1MABP and APTS-BuMA

In a 1 mL volumetric flask was added HEMA (354 mg, 2.45 mmol), PEG-DMA (mw=1000, 111 mg, 0.111 mmol), SPM (28 mg, 0.114), APTS-BuMA (0.2 mL of a 0.01M solution, 0.002 mmol), 1MABP (0.021 g, 0.02 mmol), VA-044 (2.4 mg, 0.0074 mmol). The mixture was polymerized at 40° C. for 24 hours using a mold and procedures similar to that described in Example 40. The glucose response of the hydrogel film thus obtained was measured as described in Example 4.

B. Hydrogel Containing P2-3,3-oBBV and APTS-DegMA

Figure 21A:
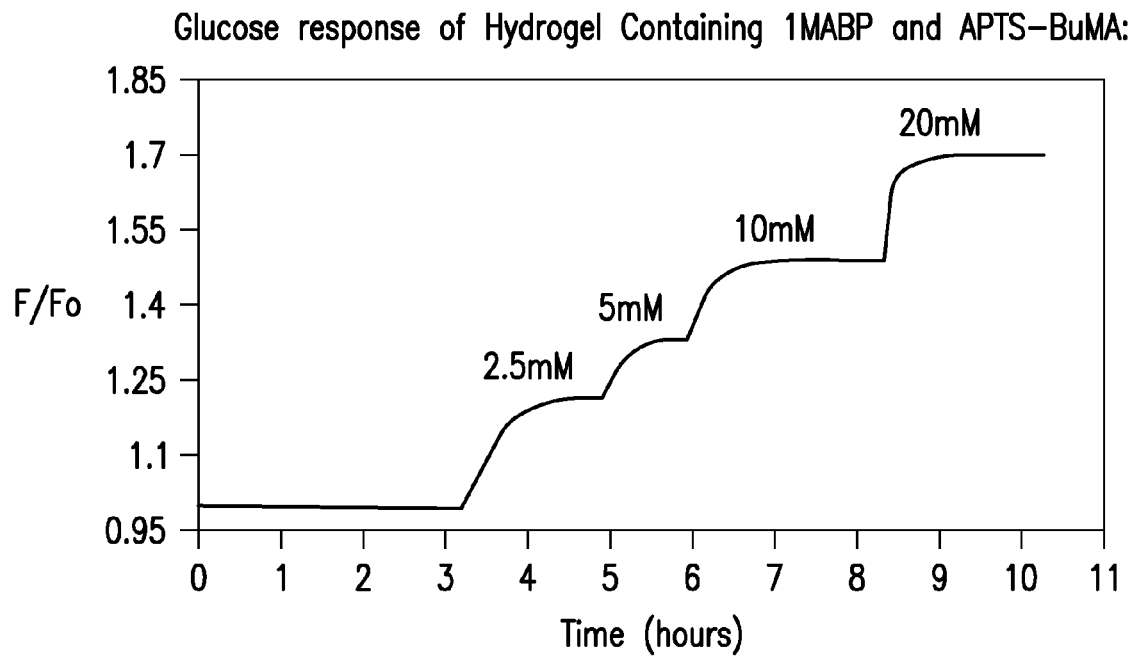
FIG. 21A is a graphic representation of glucose response of the hydrogel containing 1 MABP and APTS-BuMA with F/F° plotted against time in hours.
Figure 21B:
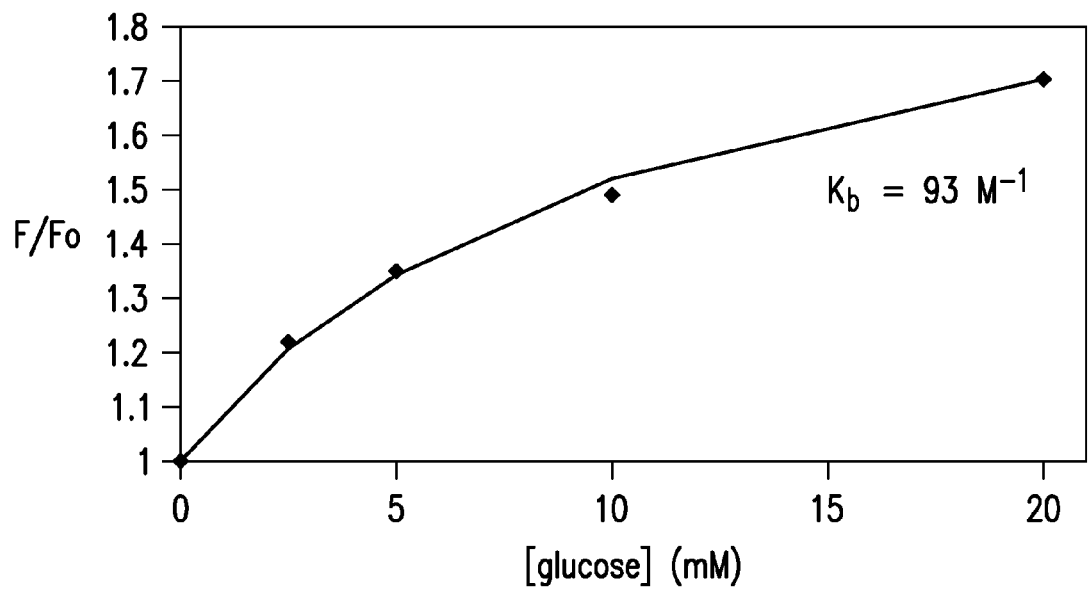
FIG. 21B is a graphic representation of glucose response of the hydrogel containing 1 MA BP and APTS-BuMA with F/F° plotted against glucose level in mM.
Figure 22A:
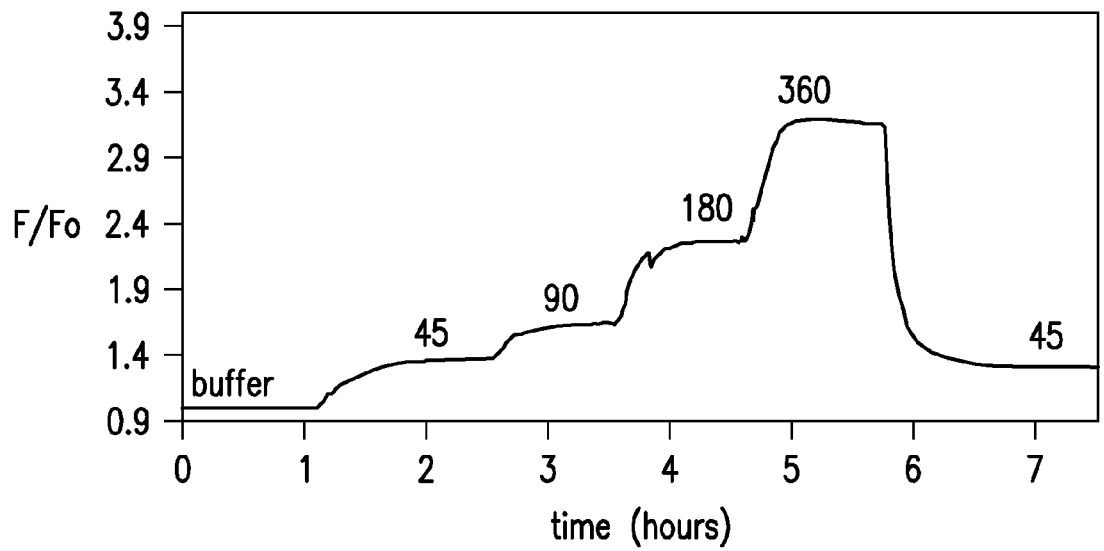
FIG. 22A is a graphic representation of glucose response of the hydrogel containing P2-33'-oBBV and APTS-DegMA with F/F° plotted against time in hours.
Figure 22B:
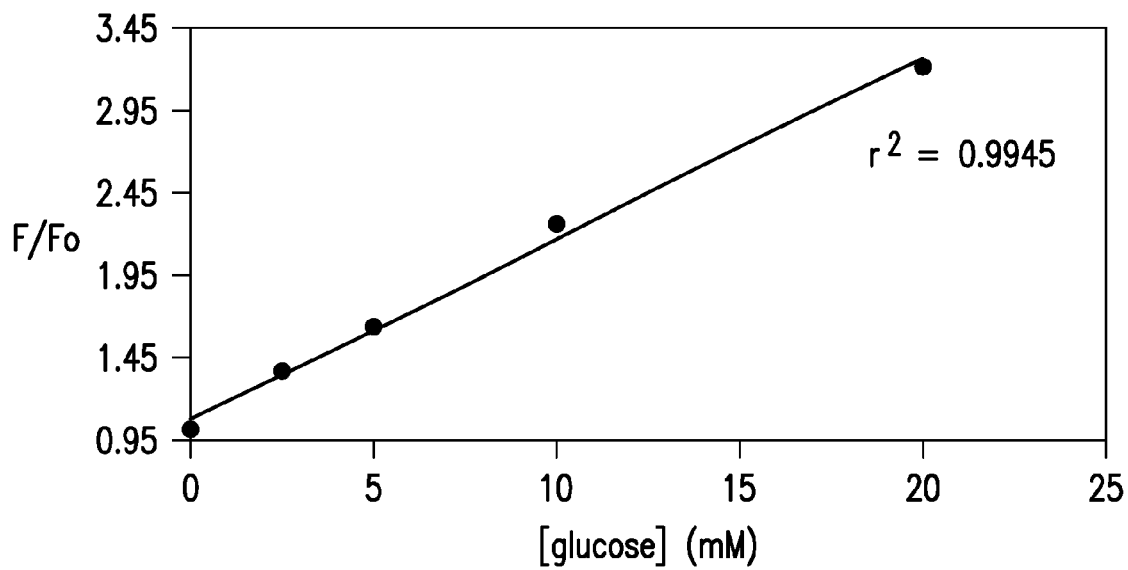
FIG. 22B is a graphic representation of glucose response of the hydrogel containing P2-3,3'-oBBV and APTS-DegMA with F/F° plotted against glucose level in mM.

In a 1 mL volumetric flask was added HEMA (354 mg, 2.45 mmol), PEG-DMA (mw=1000, 111 mg, 0.111 mmol), SPM (28 mg, 0.114), APTS-DegMA (0.2 mL of a 0.01M solution, 0.002 mmol), P2-3,3-oBBV (0.030 g, 0.04 mmol), VA-044 (2.4 mg, 0.0074 mmol). The mixture was polymerized at 40° C. for 24 hours using a mold and procedures similar to that described in Example 40. The glucose response of the hydrogel film thus obtained was measured as described in Example 4. The results are shown in FIGS. 21A and 21B. The glucose response is shown in FIGS. 22A and 22B.

EXAMPLE 60

Quantum Dot-Based Glucose Sensor

A sensing hydrogel is prepared in a manner similar to that described in Example 14 above, except the polymeric dye powder is replaced by an effective amount of carboxylated quantum dots ("Fort Orange" CdSe core shell QDs—from Evidenttech of Troy, N.Y. and the quencher monomer is replaced by an equivalent amount of P3,3'-oBBV [see Example 53]. The sensing hydrogel thus prepared shows an increase in fluorescence emission monitored at 604 nm when contacted with a solution of 100 mg/dL glucose at pH=7.4 and excited at 462 nm.

While only a few embodiments of the invention have been shown and described herein, it will become apparent to those skilled in the art that various modifications and changes can be made in a glucose sensor and its components including the fluorophore dye, quencher and optimal polymer matrix for monitoring polyhydroxyl-containing organic analytes, primarily for in vitro or in vivo glucose monitoring, without departing from the spirit and scope of the present invention. All such modifications and changes coming within the scope of the appended claims are intended to be carried out thereby.

What is claimed is:

1. A device for optically determining an analyte concentration, which device comprises:
   an analyte permeable component;
   a fluorophore confined by, immobilized in, or covalently attached to the analyte permeable component, which fluorophore absorbs light at a first wavelength and emits light at a second wavelength, wherein the fluorophore comprises a substituted pyrene sulfonate;
   a quencher confined by, immobilized in, or covalently attached to the analyte permeable component, which quencher modifies the light emitted by the fluorophore by an amount related to the analyte concentration;
   a light source; and
   a detector.

2. The device of claim 1, wherein the analyte permeable component comprises a polymer matrix.

3. The device of claim 1 wherein the analyte permeable component comprises a polymer, wherein the polymer is made from a monomer independently selected from the group consisting of 2-hydroxyethylmethacrylate (HEMA), polyethylene glycol methacrylate (PEGMA), methacrylic acid, hydroxyethyl acrylate, N-vinyl pyrrolidone, acrylamide, N,N'-dimethyl acrylamide, methacryloylaminopropyl trimethylammonium chloride, diallyl dimethyl ammonium. chloride, vinyl benzyl trimethyl ammonium chloride, sodium sulfopropyl methacrylate, and combinations thereof.

4. The device of claim 3, wherein the polymer is further made with crosslinkers selected from the group consisting of ethylene dimethacrylate, polyethylene glycol dimethacrylate (PEGDMA), methylene bis acrylamide, trimethylolpropane triacrylate, and combinations thereof.

5. The device of claim 2, wherein the polymer matrix is insoluble in water and the water-insoluble polymer matrix is prepared from monomers selected from the group consisting of HPTS(Lys-MA)$_3$, HPTS-MA, HPTS-CO$_2$-MA, APTS-BuMA, and APTS-DegMA.

6. The device of claim 5 wherein the water-insoluble polymer matrix comprises copolymers 2-hydroxyethylmethacrylate (HEMA) and polyethylene glycol dimethacrylate or N,N'-dimethylacrylamide and methylene-bis-acrylamide.

7. The device of claim 1, wherein the analyte permeable component comprises a membrane, which confines the fluorophore and the quencher.

8. The device of claim 2, wherein the polymer matrix comprises copolymers of 8-hydroxypyrene-1-N-(methacrylamidopropylsulfonamido)-N',N"-3,6-bis(carboxypropylsulfonamide) HPTS-CO$_2$-MA with HEMA or PEGMA.

9. The device of claim 1, wherein the analyte permeable component comprises a biocompatible coating.

10. The device of claim 2, wherein the fluorophore is bonded to the polymer matrix.

11. The device of claim 1, wherein the substituted pyrene sulfonate is a pyranine derivative selected from the structure:

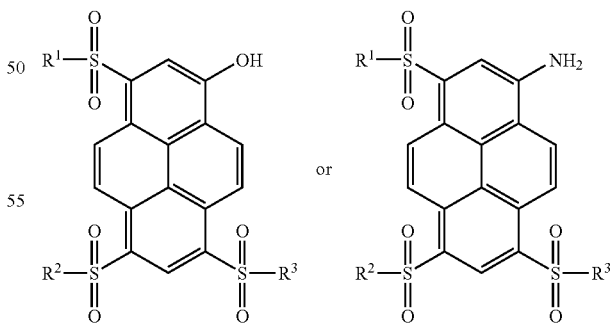

wherein $R^1$, $R^2$, and $R^3$ are each —NHR$^4$, $R^4$ is —CH$_2$—CH$_2$(—O—CH$_2$—CH$_2$)$_n$—X$^1$;
wherein X$^1$ is —OH, OCH$_3$—CO$_2$H, —CONH$_2$, —SO$_3$H, or —NH$_2$; and
n is between about 70 and 10,000.

12. The device of claim 1, wherein the fluorophore is
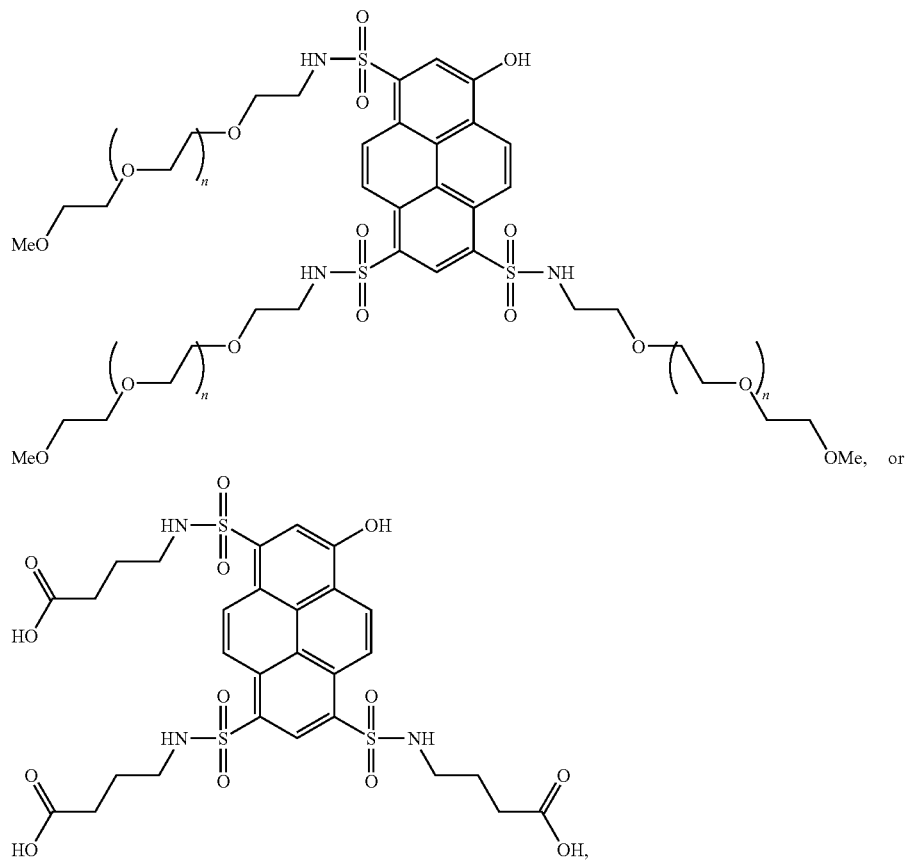
wherein n is about 125.
13. The device of claim 1, wherein the quencher is a boronic acid substituted viologen.
14. The device of claim 1, wherein the analyte is a polyhydroxyl-substituted organic molecule.
15. The device of claim 1, wherein the light source is a blue light emitting diode (LED).
* * * * *